(12) United States Patent
Usdin et al.

(10) Patent No.: US 7,122,624 B2
(45) Date of Patent: Oct. 17, 2006

(54) PARATHYROID HORMONE RECEPTOR LIGANDS

(75) Inventors: Ted B. Usdin, Betheseda, MD (US); Samuel R. J. Hoare, San Diego, CA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 579 days.

(21) Appl. No.: 10/014,162

(22) Filed: Dec. 11, 2001

(65) Prior Publication Data

US 2003/0032096 A1 Feb. 13, 2003

Related U.S. Application Data

(63) Continuation of application No. PCT/US00/16776, filed on Jun. 15, 2000.

(60) Provisional application No. 60/139,335, filed on Jun. 15, 1999.

(51) Int. Cl.
*C07K 14/635* (2006.01)

(52) U.S. Cl. .................................................. 530/324

(58) Field of Classification Search ................ 530/399, 530/324, 325, 326, 327, 328, 329, 330, 331
See application file for complete search history.

(56) References Cited

U.S. PATENT DOCUMENTS 3,886,132 A * 5/1975 Brewer et al. ............... 530/324
5,194,375 A * 3/1993 Park et al. .................. 435/69.1

FOREIGN PATENT DOCUMENTS

| WO | WO 98/04591 | 2/1998 |
| WO | WO 02/33049 | 4/2002 |

OTHER PUBLICATIONS

Angal et al. "Purification by exploitation of activity" Chapter 5, In, Protein Purification Methods: A Practical Approach, Harris et al. (Eds.), Sep. 1989, IRL Press, Oxford, UK, pp. 245.*
Guo et al. Protein tolerance to random amino acid change. Proc Natl Acad Sci U S A. Jun. 22, 2004;101(25):9205-10.*

Gardella, T. J., et al. (1996) Converting Parathyroid Hormone-related Peptide (PTHrP) into a Potent PTH-2 Receptor Agonist. J. Biol. Chem. 271(33):19888-19893.
Hoare, S. R. J., et al. (1999) Comparison of Rat and Human Parathyroid Hormone 2 (PTH2) Receptor Activation: PTH Is a Low Potency Partial Agonist at the Rat PTH2 Receptor. Endocrinology 140(10):4419-4425.
Hoare, S. R. J., et al. (2000) Tuberoinfudibular Peptide (7-39) [TIP(7-39)], a Novel, Selective, High-Affinity Antagonist for the Parathyroid Hormone-1 Receptor with No Detectable Agonist Activity, JPET 295(2):761-770.
Hoare, S. R. J., et al. (2000) Molecular Determinants of Tuberoinfundibular Peptide of 39 Residues (TIP39) Selectively for the Parathyroid Hormone-2 (PTH2) Receptor. J. Biol. Chem. 275(35):27274-27283.
Mezey, E., et al. (1998) Anatomical Studies of the Rat PTH2 Receptor. Society for Neuroscience 24:244 (Abstract).
Nakata, T., et al. (1995) Role of Basic and Acidic Fragments in Delicious Peptides (Lys-Gly-Asp-Glu-Glu-Ser-Leu-Ala) and the Taste Behavior of Sodium and Potassium Salts in Acidic Oligopeptides. Biosci. Biotech. Biochem. 59(4):698-693.
Usdin, T. B., et al. (1995) Identification and Function Expression of a Receptor Selectively Recognizing Parathyroid Hormone, the PTH2 Receptor. J. Biol. Chem. 270(26):15455-15458.
Usdin, T. B., et al. (1996) Distribution of Parathyroid Hormone-2 Receptor Messenger Ribonucleic Acid in Rat. Endocrinology 137(10):4285-4297.
Usdin, T. B. (1997) The parathyroid hormone-2 receptor: current status. Exp. Mol. Med. 29(1):13-17.
Usdin, T. B. (1997) Evidence for a Parathyroid Hormone-2 receptor selective ligand in the hypothalamus. Endocrinology 138(2):831-834.
Usdin, T. B., et al. (1998) Progress on the Identification of a Novel PTH2 Receptor-Selective Peptide From the Hypothalamus. Society for Neuroscience 24:2044 (Abstract).
Usdin, T. B., et al. (1999) Distribution of the Parathyroid Hormone 2 Receptor in Rat: Immunolocalization Reveals Expression by Several Endocrine Cells. Endocrinology 140(7):3363-3371.
Usdin, T. B., et al. (1999) TIP39: a new neuropeptide and PTH2-receptor agonist from hypothalamus. Nature Neuroscience 2(11):941-943.
Usdin, T. B. (2000) The $PTH_2$ receptor and TIP39: a new peptide-receptor systemm. TIPS 21:128-130.

* cited by examiner

*Primary Examiner*—David Romeo
(74) *Attorney, Agent, or Firm*—Knobbe, Martens, Olson & Bear, LLP

(57) ABSTRACT

An isolated or purified PTH2 receptor ligand or PTH1 receptor ligand is disclosed.

1 Claim, 24 Drawing Sheets

FIG. 1

```
SLALADDAAFRERARLLAALERRHWLNSYM---HKLLVLDAP  bTIP39
 AVSEIQFMHNLGKHLSSMERVEWLRKKLQDVHNFVALGAS   bPTH (1-40)
 AVSEHQLLHDKGKSIQDLRRRFFLHHLIAEIHT-AEIRAT   hPTHrP (1-39)
```

FIG. 8

PARATHYROID HORMONE RECEPTOR LIGANDS

CROSS-REFERENCE TO RELATED APPLICATIONS

This application is a continuation of international application number PCT/US00/16776 filed Jun. 15, 2000, and claims the benefit of priority of international application number PCT/US00/16776 having international filing date of Jun. 15, 2000, designating the United States of America and published in English, which claims the benefit of priority of U.S. provisional patent application No. 60/139,335, filed Jun. 15, 1999; both of which are hereby expressly incorporated by reference in their entireties.

FIELD OF THE INVENTION

The present invention relates to ligands of PTH2 and PTH1 receptors, wherein said ligands may be peptides, fragments and analogs thereof having PTH2 or PTH1 receptor binding activity, and methods for using same.

BACKGROUND OF THE INVENTION

Parathyroid Hormone Receptors

The parathyroid hormone receptors (PTH receptors) are part of an extended family of receptors. Usdin, et al., *J Biol Chem* 270:15455–15458 (1995). The human parathyroid hormone type 2 receptor (PTH2 receptor) shares about 51% amino-acid sequence identity with the human parathyroid hormone type 1 receptor (PTH1 receptor). Both PTH receptors belong to the Type II family of G-protein-coupled receptors which respond to peptide modulators, including calcitonin, glucagon, secretin and vasoactive intestinal polypeptide. Both PTH receptors are activated by PTH, but only the PTH1 receptor is activated by parathyroid hormone-related protein (PTHrP). The PTH2 and PTH1 receptors, together with their ligands, have presumably evolved to selectively mediate different physiological functions.

Parathyroid Hormone 2 Receptor

The PTH2 receptor is a G-protein coupled receptor selectively activated by parathyroid hormone (PTH) and not by PTHrP. The first demonstration of this was by Usdin et al. (*J Biol Chem* 270:15455–15458 (1995)) and later by Behar et al. (*Endocrinology* 137:2748–57 (1996)) and Gardella et al. (*J Biol Chem* 271:19888–19893 (1996)). It is most similar in sequence and ligand recognition specificity to the PTH1 receptor (also called the PTH/PTHrP receptor). Abou-Samra, et al., *Cell Biology* 89:2732–2736 (1992); Juppner, et al., *Science* 254:1024–1026 (1991). Prior to discovery of the PTH2 receptor, studies of PTH action had not predicted the existence of the PTH2 receptor.

Recent work implies a significant role of the PTH2 receptor in regulating a number of diverse physiological processes. In view of this work it is clear that identifying the endogenous ligand that binds to and activates the PTH2 receptor is extremely important and may provide a therapeutic vehicle with which to treat a number of metabolic disorders. Antagonists of the PTH2 receptor would also have therapeutic importance as agents for modulating PTH2 receptor function.

Parathyroid Hormone 1 Receptor

The parathyroid hormone type 1 receptor (PTH1 receptor) mediates the principal physiological responses to PTH and to PTH-related protein (PTHrP). Potts et al., in Williams' Textbook of Endocrinology, pp. 920–966 (1995). PTH is involved in the regulation of calcium homeostasis, in that the hormone acts on the PTH1 receptor in bone and kidney to elevate blood calcium levels. PTHrP is a locally-acting autocrine/paracrine factor and developmental regulator. Both of these peptides are involved in disorders of calcium metabolism. In humoral hypercalcaemia of malignancy (HHM) certain tumors produce very high levels of PTHrP, leading to activation of the PTH1 receptor and elevation of blood calcium levels. Grill et al., *European Journal of Cancer* 34:222–229 (1998). In primary hyperparathyroidism (HPT), elevated blood calcium levels results from excessive secretion of PTH from a parathyroid gland. Nemeth and Fox, *Trends Endocrinol Metab* 10:66–71 (1999). In secondary and tertiary HPT, chronic renal failure leads to reduced calcium levels, morphological changes of the parathyroid gland and elevated PTH secretion. Slatopolsky et al., *Kidney Int Suppl* 73:S14–9 (1999). The PTH1 receptor is also involved in regulating phosphate homeostasis. Since activation of the PTH1 receptor is involved in these disorders, antagonism of the effects of PTH or PTHrP on the receptor may be of therapeutic utility.

SUMMARY OF THE INVENTION

An isolated or purified PTH2 receptor ligand or PTH1 receptor ligand is disclosed.

BRIEF DESCRIPTION OF THE DRAWINGS

FIG. 1. Alignment of the rat (upper) (SEQ ID NO: 109) and human (lower) (SEQ ID NO: 110) PTH2 receptor sequences. The deduced amino-acid sequences were aligned using the Gap algorithm of the Wisconsin GCG Package. Identical residues are indicated by vertical lines and similar residues by dots. Putative transmembrane domains are indicated by gray shading, as determined by visual inspection of hydrophobicity plots.

FIG. 8. Amino-acid sequence alignment of bovine TIP39 (SEQ ID NO: 1), with the N-terminal sequence of bovine PTH (SEQ ID NO: 111) and PTHrP (SEQ ID NO: 112). Residues common to all three sequences are boxed. Residues common to only bTIP39 and bPTH are enclosed by the dashed box and additional residues common to only bPTH and PTHrP are underlined.

DETAILED DESCRIPTION OF THE INVENTION

Figure 2C:
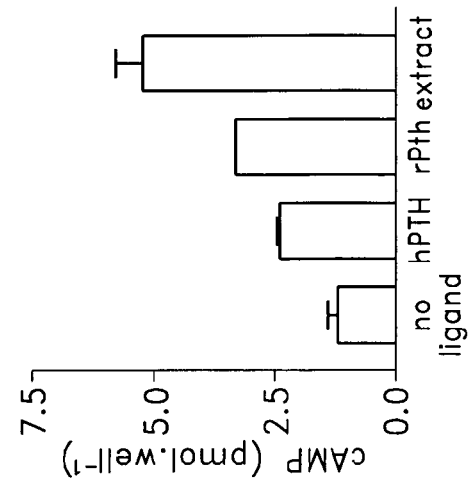
FIG. 2. Stimulation of cAMP accumulation by human PTH, rat PTH, and bovine hypothalamic extract. COS-7 cells were transfected with plasmids encoding β-galactosidase (A), the human PTH2 receptor (B) and the rat PTH2 receptor (C). Total cAMP was measured (using a 25 µl assay volume). The response to vehicle, 3.2 µM hPTH(1–34), 3.2 µM rPTH(1–34) and 200 µg ml$^{-1}$ bovine hypothalamic extract is shown. Data are expressed as total cAMP produced per well of a 96-well plate and represent the mean±range of duplicate measurements. The experiment was performed twice with similar results.

The disclosure below teaches PTH receptor ligands. The disclosure also teaches peptides, fragments thereof, and analogs that bind PTH2 and PTH1 receptors. The peptides, fragments thereof, or analogs possess a variety of diagnostic and therapeutic uses, which are discussed below.

Biochemical Related Embodiments

Based on the anatomical distribution of the PTH2 receptor and its coupling to activation of adenylyl cyclase, a number of functions for a new hypothalamic peptide are now described. It is important to note that while the hypothalamus was the most convenient place from which to purify the peptide, it is likely to also be synthesized in other areas.

High concentrations of the PTH2 receptor in somatostatin-containing hypothalamic periventricular nucleus neurons suggest that it modulates somatostatin release from the hypothalamus. This will affect secretion of all pituitary hormones. Accordingly, a peptide, fragment, or analog, with PTH2 receptor binding activity would be useful in the treatment of acromegaly, infertility, thyroid dysfunction, Cushings syndrome, gynecomastia, excessive lactation, and other pituitary dysfunctions. The PTH2 receptor is also thought to be involved in the regulation of pituitary function and in particular growth hormone secretion.

Expression of the PTH2 receptor in other hypothalamic areas including the arcuate and paraventricular nuclei, and partial colocalization with neuropeptide Y suggest a role in regulation of homeostasis, and in particular of feeding. Accordingly, a peptide, fragment, or analog, with PTH2 receptor binding activity would be useful in treating obesity or other eating or metabolic disorders.

Expression of the PTH2 receptor in midline thalamic nuclei, several amygdaloid nuclei, and the septum suggests involvement in limbic functions. Accordingly, a peptide, fragment, or analog, with PTH2 receptor binding activity would be useful in treatment of mental disorders, including depression, schizophrenia and dementia.

Very high levels of expression of the PTH2 receptor on nerve fibers and terminals in the outer layers of the dorsal horn of the spinal cord and the caudal part of the trigeminal nucleus suggest a role for the PTH2 receptor in modulating painful sensation. The nerve cells that project to this part of the spinal cord are primarily involved in perception of painful or unpleasant (nociceptive) stimuli. Further, the PTH2 receptor is synthesized by cells in the marginal layer of the spinal cord, which may respond to the intensity of a painful stimulus. This suggests that the PTH2 receptor is involved in modulation of nociception. Accordingly, a peptide, fragment, or analog, with PTH2 receptor binding activity, would be useful in treating certain aspects of acute or chronic pain. The PTH2 receptor is present on the spinal cord terminals of a specific subset of sensory neurons (some of those containing the peptide CGRP) suggesting involvement in selective aspects of sensory perception, perhaps visceral and joint sensation. Further, PTH2 receptor ligands are useful in the treatment of migraine headaches.

High levels of PTH2 receptor expression on somatostatin synthesizing cells in pancreatic islets suggest a role in modulating pancreatic islet somatostatin release and therefore that the peptide leads to modulation of insulin and/or glucagon production and/or release. Thus, peptides, fragments, or analogs, with PTH2 receptor binding activity may have utility in the treatment of diabetes and other metabolic disorders.

PTH2 receptor expression by calcitonin synthesizing thyroid parafollicular cells suggests a role for the peptide in regulating calcitonin secretion and thus in regulation of blood and body calcium levels. Accordingly, peptides, fragments, or analogs, with PTH2 receptor binding activity have utility in the treatment or prevention of osteoporosis, hypercalcemia and other disorders affecting calcium metabolism.

The PTH2 receptor is present in blood vessels and the heart, and administration of the peptide has been observed to alter blood pressure. PTH2 may also affect proliferation of vascular endothelium, and/or cardiac contractility. Areas of utility for peptides, fragments, or analogs having PTH2 receptor binding activity include treatment of hypertension, congestive heart failure, and control of tumor growth (through an effect on angiogenesis).

The PTH2 receptor is also expressed by cells within the pulmonary bronchioles. These cells may be involved in airway constriction and mucous secretion. Thus, peptides, fragments, or analogs, with PTH2 receptor binding activity have utility in treating asthma, emphysema, or other restrictive lung diseases.

The PTH2 receptor is present on a very small number of discrete cells in the kidney that may be part of the juxtaglomerular apparatus. These cells affect blood pressure by releasing renin which acts on circulating angiotensinogen to produce a vasoactive agent. Other workers have provided evidence that a hypothalamic extract stimulated release of renin from the kidney producing a decrease in blood pressure. However, there has been no follow up of this work. Moreover, these references failed to isolate and purify the agent to homogeneity or even to a level of purity suitable for amino acid sequence analysis. Nor did they ultimately articulate the amino acid sequence articulated herein. A PTH2 receptor ligand may be useful in treatment of hypertension through a renin-modulating mechanism.

The PTH2 receptor is present on oligodendrocytes, which are the myelin producing cells in the central nervous system. Peptides, fragments, or analogs with PTH2 receptor binding activity could affect the differentiation and proliferation of these cells. Specifically, the peptides, fragments, or analogs of the present invention would be useful in increasing the formation of myelin, and thus be useful in treating demyelinating conditions such as multiple sclerosis and leukodystrophies.

As discussed above, the original peptide was purified from hypothalamic tissue. The wild type form of the original peptide can be purified from brain tissue of mammals. Examples of such mammals include rats, bovines, and humans. A wild type peptide can also be obtained from the brain tissue of these and other mammals as well.

A wild type peptide having PTH2 receptor binding activity can be isolated from various bodily tissues using standard techniques well known in the art. Generally, a tissue source for the peptide is selected, and the peptide is solubilized therefrom. A variety of solubilization techniques are well known in the art. For example, osmotic lysis, grinding, use of blenders, ultrasonic disruption, presses and other methods are available. The resulting tissue extract can be stabilized to prevent the possible degradation of the peptide. Stabilization is achieved by monitoring and stabilizing pH levels, minimizing the degree of oxidation, monitoring medium polarity and ionic strength, inhibiting protease activity or reducing protease contamination, and maintaining the extract at a favorable temperature to increase the yield of the peptide. One example of a peptide isolation protocol is found in Bennet, et al., *Biochem J* 175: 1139–41 (1978).

Once the peptide is isolated from the tissue source, it is enriched and concentrated using a variety of techniques. Differential solubility of the peptide with respect to the other components of the cellular milieu can be exploited to purify the peptide. Salt cuts, ion exchange chromatography, affinity column chromatography using the PTH2 receptor as a means of isolating the peptide, are all examples of purification techniques. The end result of this step is a peptide that is substantially enriched as compared to the other components of the tissue from which the peptide was isolated.

As used herein, "enriched" means that the concentration of the material is at least 2, 5, 10, 100, or 1,000 times its natural concentration in unprocessed brain tissue. In one advantageous embodiment, the peptide is found at 0.01%, by weight, preferably at least about 0.1% by weight. Enriched preparations of about 0.5%, 1%, 5%, 10% and 20% by weight are also contemplated.

The term "isolated" requires that the material be removed from its original environment (e.g., the natural environment if it is naturally occurring). For example, a naturally-occurring polypeptide present in a living animal is not isolated, but the same polypeptide, separated from some or all of the coexisting materials in the natural system, is isolated.

It is also advantageous that a peptide, fragment, or analogs thereof be produced in a purified form. The term "purified" does not require absolute purity; rather, it is intended as a relative definition, with reference to the purity of the material in its natural state. Purification of natural material to at least one order of magnitude, preferably two or three orders, and more preferably four or five orders of magnitude is expressly contemplated. In another embodiment, the term purified with respect to the peptides, fragments, or analogs of the invention means a state of purification permitting accurate amino acid sequence determination using standard techniques well known in the art.

The amino acid sequence of the original peptide was determined using methods well known in the art and described in Examples that follow. The Edman degradation method was used for determining the amino acid sequence of the peptide starting from the amino terminus of the peptide. The Edman degradation procedure removes and identifies one amino acid at a time from the amino end of the peptide, and can be repeated so as to identify the complete sequence of amino acids present in an isolated peptide. Sanger, *Adv Protein Chem* 7:1–67 (1952); Findlay & Geisow, eds., Protein Sequencing: A Practical Approach, IRL Press, Oxford (1989). Methods are also known for determining an amino acid sequence from the carboxy-terminal end. Matsuo, et al., *Biochem Biophys Res Commun* 22:69–74 (1966); Strydom, D. J., *Anal Biochem* 174:679–686 (1988). The sequence of the peptide, called tuberinfundibular peptide of 39 residues (TIP39), was:

NH$_2$-SLALADDAAFRERARLLAALERRHWLN-SYMHKLLVLDAP-COOH (SEQ ID NO: 1).

The invention contemplates using the entire TIP39 peptide having PTH2 receptor binding activity as a diagnostic and therapeutic agent. In another embodiment, the invention contemplates a series of peptide truncations, beginning at either the amino-terminal or carboxy-terminal ends of the protein. The peptides can be produced by another of a number of protocols well known to those of skill in the art. Some short examples include, purifying one or more of the peptides taught by the invention, followed by modification of the peptide. Alternatively, the peptides can be produced recombinantly, using molecular biology and biochemical techniques, or synthetically and then used in the methods described below.

A variety of truncations to the peptide of SEQ ID NO:1 are contemplated. Examples of these peptide truncations are listed below in Table 1 and Table 2. These peptides may themselves be chemically modified.

TABLE 1

Peptide Analog Amino-Terminal Truncations of TIP39

| Sequence | SEQ ID NO |
|---|---|
| X-DAP-Z | SEQ ID NO: 37 |
| X-LDAP-Z | SEQ ID NO: 36 |
| X-VLDAP-Z | SEQ ID NO: 35 |
| X-LVLDAP-Z | SEQ ID NO: 34 |
| X-LLVLDAP-Z | SEQ ID NO: 33 |
| X-KLLVLDAP-Z | SEQ ID NO: 32 |
| X-HKLLVLDAP-Z | SEQ ID NO: 31 |
| X-MHKLLVLDAP-Z | SEQ ID NO: 30 |
| X-YMHKLLVLDAP-Z | SEQ ID NO: 29 |
| X-SYMHKLLVLDAP-Z | SEQ ID NO: 28 |
| X-NSYMHKLLVLDAP-Z | SEQ ID NO: 27 |
| X-LNSYMHKLLVLDAP-Z | SEQ ID NO: 26 |
| X-WLNSYMHKLLVLDAP-Z | SEQ ID NO: 25 |
| X-HWLNSYMHKLLVLDAP-Z | SEQ ID NO: 24 |
| X-RHWLNSYMHKLLVLDAP-Z | SEQ ID NO: 23 |
| X-RRHWLNSYMHKLLVLDAP-Z | SEQ ID NO: 22 |
| X-ERRHWLNSYMHKLLVLDAP-Z | SEQ ID NO: 21 |
| X-LERRHWLNSYMHKLLVLDAP-Z | SEQ ID NO: 20 |
| X-ALERRHWLNSYMHKLLVLDAP-Z | SEQ ID NO: 19 |
| X-AALERRHWLNSYMHKLLVLDAP-Z | SEQ ID NO: 18 |
| X-LAALERRHWLNSYMHKLLVLDAP-Z | SEQ ID NO: 17 |
| X-LLAALERRHWLNSYMHKLLVLDAP-Z | SEQ ID NO: 16 |
| X-RLLAALERRHWLNSYMHKLLVLDAP-Z | SEQ ID NO: 15 |
| X-ARLLAALERRHWLNSYMHKLLVLDAP-Z | SEQ ID NO: 14 |
| X-RARLLAALERRHWLNSYMHKLLVLDAP-Z | SEQ ID NO: 13 |
| X-ERARLLAALERRHWLNSYMHKLLVLDAP-Z | SEQ ID NO: 12 |
| X-RERARLLAALERRHWLNSYMHKLLVLDAP-Z | SEQ ID NO: 11 |
| X-FRERARLLAALERRHWLNSYMHKLLVLDAP-Z | SEQ ID NO: 10 |
| X-AFRERARLLAALERRHWLNSYMHKLLVLDAP-Z | SEQ ID NO: 9 |
| X-AAFRERARLLAALERRHWLNSYMHKLLVLDAP-Z | SEQ ID NO: 8 |
| X-DAAFRERARLLAALERRHWLNSYMHKLLVLDAP-Z | SEQ ID NO: 7 |
| X-DDAAFRERARLLAALERRHWLNSYMHKLLVLDAP-Z | SEQ ID NO: 6 |
| X-ADDAAFRERARLLAALERRHWLNSYMHKLLVLDAP-Z | SEQ ID NO: 5 |
| X-LADDAAFRERARLLAALERRHWLNSYMHKLLVLDAP-Z | SEQ ID NO: 4 |
| X-ALADDAAFRERARLLAALERRHWLNSYMHKLLVLDAP-Z | SEQ ID NO: 3 |
| X-LALADDAAFRERARLLAALERRHWLNSYMHKLLVLDAP-Z | SEQ ID NO: 2 |
| X-SLALADDAAFRERARLLAALERRHWLNSYMHKLLVLDAP-Z | SEQ ID NO: 1 |

"X" may represent an amino group, a hydrophobic group, including but not limited to carbobenzoxyl, dansyl, or T-butyloxycarbonyl; an acetyl group; a 9-fluorenylmethoxycarbonyl (FMOC) group; a macromolecular carrier group including but not limited to lipid-fatty acid conjugates, polyethylene glycol, or carbohydrates.

"Z" may represent a carboxyl group; an amido group; a T-butyloxycarbonyl group; a macromolecular carrier group including but not limited to lipid-fatty acid conjugates, polyethylene glycol, or carbohydrates.

TABLE 2

Peptide Analog Carboxy Terminal Truncations of TIP39

| Sequence | SEQ ID NO |
|---|---|
| X-SLA-Z | SEQ ID NO: 73 |
| X-SLAL-Z | SEQ ID NO: 72 |
| X-SLALA-Z | SEQ ID NO: 71 |
| X-SLALAD-Z | SEQ ID NO: 70 |
| X-SLALADD-Z | SEQ ID NO: 69 |
| X-SLALADDA-Z | SEQ ID NO: 68 |
| X-SLALADDAA-Z | SEQ ID NO: 67 |
| X-SLALADDAAF-Z | SEQ ID NO: 66 |
| X-SLALADDAAFR-Z | SEQ ID NO: 65 |
| X-SLALADDAAFRE-Z | SEQ ID NO: 64 |
| X-SLALADDAAFRER-Z | SEQ ID NO: 63 |
| X-SLALADDAAFRERA-Z | SEQ ID NO: 62 |
| X-SLALADDAAFRERAR-Z | SEQ ID NO: 61 |
| X-SLALADDAAFRERARL-Z | SEQ ID NO: 60 |
| X-SLALADDAAFRERARLL-Z | SEQ ID NO: 59 |
| X-SLALADDAAFRERARLLA-Z | SEQ ID NO: 58 |
| X-SLALADDAAFRERARLLAA-Z | SEQ ID NO: 57 |
| X-SLALADDAAFRERARLLAAL-Z | SEQ ID NO: 56 |

TABLE 2-continued

Peptide Analog Carboxy Terminal Truncations of TIP39

| Sequence | SEQ ID NO |
|---|---|
| X-SLALADDAAFRERARLLAALE-Z | SEQ ID NO: 55 |
| X-SLALADDAAFRERARLLAALER-Z | SEQ ID NO: 54 |
| X-SLALADDAAFRERARLLAALERR-Z | SEQ ID NO: 53 |
| X-SLALADDAAFRERARLLAALERRH-Z | SEQ ID NO: 52 |
| X-SLALADDAAFRERARLLAALERRHW-Z | SEQ ID NO: 51 |
| X-SLALADDAAFRERARLLAALERRHWL-Z | SEQ ID NO: 50 |
| X-SLALADDAAFRERARLLAALERRHWLN-Z | SEQ ID NO: 49 |
| X-SLALADDAAFRERARLLAALERRHWLNS-Z | SEQ ID NO: 48 |
| X-SLALADDAAFRERARLLAALERRHWLNSY-Z | SEQ ID NO: 47 |
| X-SLALADDAAFRERARLLAALERRHWLNSYM-Z | SEQ ID NO: 46 |
| X-SLALADDAAFRERARLLAALERRHWLNSYMH-Z | SEQ ID NO: 45 |
| X-SLALADDAAFRERARLLAALERRHWLNSYMHK-Z | SEQ ID NO: 44 |
| X-SLALADDAAFRERARLLAALERRHWLNSYMHKL-Z | SEQ ID NO: 43 |
| X-SLALADDAAFRERARLLAALERRHWLNSYMHKLL-Z | SEQ ID NO: 42 |
| X-SLALADDAAFRERARLLAALERRHWLNSYMHKLLV-Z | SEQ ID NO: 41 |
| X-SLALADDAAFRERARLLAALERRHWLNSYMHKLLVL-Z | SEQ ID NO: 40 |
| X-SLALADDAAFRERARLLAALERRHWLNSYMHKLLVLD-Z | SEQ ID NO: 39 |
| X-SLALADDAAFRERARLLAALERRHWLNSYMHKLLVLDA-Z | SEQ ID NO: 38 |
| X-SLALADDAAFRERARLLAALERRHWLNSYMHKLLVLDAP-Z | SEQ ID NO: 1 |

"X" may represent an amino group, a hydrophobic group, including but not limited to carbobenzoxyl, dansyl, or T-butyloxycarbonyl; an acetyl group; a 9-fluorenylmethoxycarbonyl (FMOC) group; a macromolecular carrier group including but not limited to lipid-fatty acid conjugates, polyethylene glycol, or carbohydrates.

"Z" may represent a carboxyl group; an amido group; a T-butyloxycarbonyl group; a macromolecular carrier group including but not limited to lipid-fatty acid conjugates, polyethylene glycol, or carbohydrates.

In addition to the terminal truncations of the peptide of the invention, internal truncations of the peptide are also contemplated. Internal truncations of the peptide include:

-LAL- and -LAL-5-39, wherein 5–39 means A, AD, ADD, . . . ADDAAFRERARLLAALERRHWLNSYMHKLLVLDAP-(SEQ ID NO: 74)

-ALA and ALA-6-39, wherein 6–39 means D, DD, DDA, . . . DDAAFRERARLLAALERRHWLNSYMHKLLVLDAP-(SEQ ID NO: 75)

-LAD and LAD-7-39, wherein 7–39 means D, DA, DAA, . . . DAAFRERARLLAALERRHWLNSYMHKLLVLDAP-(SEQ ID NO: 76)

-ADD and ADD-8-39, wherein 8–39 means A, AA, AAF, . . . AAFRERARLLAALERRHWLNSYMHKLLVLDAP-(SEQ ID NO: 77)

-DDA and DDA-9-39, wherein 9–39 means A, AF, AFR, . . . AFRERARLLAALERRHWLNSYMHKLLVLDAP-(SEQ ID NO: 78)

-DAA and DAA-10-39, wherein 10–39 means F, FR, FRE, . . . FRERARLLAALERRHWLNSYMHKLLVLDAP-(SEQ ID NO: 79)

-AAF and AAF-11-39, wherein 11–39 means R, RE, RER, . . . RERARLLAALERRHWLNSYMHKLLVLDAP-(SEQ ID NO: 80)

-AFR and AFR-12-39, wherein 12–39 means E, ER, ERA, . . . ERARLLAALERRHWLNSYMHKLLVLDAP-(SEQ ID NO: 81)

-FRE and FRE-13-39, wherein 13–39 means R, RA, RAR, . . . RARLLAALERRHWLNSYMHKLLVLDAP-(SEQ ID NO: 82)

-RER and RER-14-39, wherein 14–39 means A, AR, ARL, . . . ARLLAALERRHWLNSYMHKLLVLDAP-(SEQ ID NO: 83)

-ERA and ERA-15-39, wherein 15–39 means R, RL, RLL, . . . RLLAALERRHWLNSYMHKLLVLDAP-(SEQ ID NO: 84)

-RAR and RAR-16-39, wherein 16–39 means L, LL, LLA, . . . LLAALERRHWLNSYMHKLLVLDAP-(SEQ ID NO: 85)

-ARL and ARL-17-39, wherein 17–39 means L, LA, LAA, . . . LAALERRHWLNSYMHKLLVLDAP-(SEQ ID NO: 86)

-RLL and RLL-18-39, wherein 18–39 means A, AA, AAL, . . . AALERRHWLNSYMHKLLVLDAP-(SEQ ID NO: 87)

-LLA and LLA-19-39, wherein 19–39 means A, AL, ALE, . . . ALERRHWLNSYMHKLLVLDAP-(SEQ ID NO: 88)

-LAA and LAA-20-39, wherein 20–39 means L, LE, LER, . . . LERRHWLNSYMHKLLVLDAP-(SEQ ID NO: 89)

-AAL and AAL-21-39, wherein 21–39 means E, ER, ERR, . . . ERRHWLNSYMHKLLVLDAP-(SEQ ID NO: 90)

-ALE and ALE-22-39, wherein 22–39 means R, RR, RRH, . . . RRHWLNSYMHKLLVLDAP-(SEQ ID NO: 91)

-LER and LER-23-39, wherein 23–39 means R, RH, RHW, . . . RHWLNSYMHKLLVLDAP-(SEQ ID NO: 92)

-ERR and ERR-24-39, wherein 24–39 means H, HW, HWL, . . . HWLNSYMHKLLVLDAP-(SEQ ID NO: 93)

-RRH and RRH-25-39, wherein 25–39 means W, WL, WLN, . . . WLNSYMHKLLVLDAP-(SEQ ID NO: 94)

-RHW and RHW-26-39, wherein 26–39 means L, LN, LNS, . . . LNSYMHKLLVLDAP-(SEQ ID NO: 95)

-HWL and HWL-27-39, wherein 27–39 means N, NS, NSY, . . . NSYMHKLLVLDAP-(SEQ ID NO: 96)

-WLN and WLN-28-39, wherein 28–39 means S, SY, SYM, . . . SYMHKLLVLDAP-(SEQ ID NO: 97)

-LNS and LNS-29-39, wherein 29–39 means Y, YM, YMH, . . . YMHKLLVLDAP-(SEQ ID NO: 98)

-NSY and NSY-30-39, wherein 30–39 means M, MH, MHK, . . . MHKLLVLDAP-(SEQ ID NO: 99)

-SYM and SYM-31-39, wherein 31–39 means H, HK, HKL, . . . HKLLVLDAP-(SEQ ID NO: 100)

-YMH and YMH-32-39, wherein 32–39 means K, KL, KLL, . . . KLLVLDAP-(SEQ ID NO: 101)

-MHK and MHK-33-39, wherein 33–39 means L, LL, LLV, . . . LLVLDAP-(SEQ ID NO: 102)

-HKL and HKL-34-39, wherein 34–39 means L, LV, LVL, . . . LVLDAP-(SEQ ID NO: 103)

-KLL and KLL-35-39, wherein 35–39 means V, VL, VLD, . . . VLDAP-(SEQ ID NO: 104)

-LLV and LLV-36-39, wherein 36–39 means L, LD, LDA, . . . LDAP-(SEQ ID NO: 105)

-LVL and LVL-37-39, wherein 37–39 means D, DA, or DAP

-LDA and -LDAP (SEQ ID NO: 106)

The present invention also contemplates a series of amino acid substitutions, insertions, and deletions that result in an amino acid sequence that differs from that of SEQ ID NO: 1, yet retains PTH2 receptor binding and/or activation characteristics as determined by binding studies and cAMP production assays, which are discussed below. Accordingly, the invention contemplates peptides based on the peptide disclosed herein comprising one or more amino acid substitution, insertion, or deletion at positions S1U, L2U, A3U, L4U, A5U, D6U, D7U, A8U, A9U, F10U, R11U, E12U, R13U, A14U, R15U, L16U, L17U, A18U, A19U, L20U, E21U, R22U, R23U, H24U, W25U, L26U, N27U, S28U, Y29U, M30U, H31U, K32U, L33U, L34U, V35U, L36U, D37U, A38U, and P39U, wherein U is any amino acid, or the lack thereof, that produces a peptide with PTH2 receptor binding activity and the ability to elicit the generation of cAMP.

When an amino acid residue is substituted for an already existing amino acid, the invention contemplates the use of conservative amino acids in the substitution. In one embodiment, when U is a conservative amino acid, the substitution produces a peptide with an altered amino acid sequence that retains PTH2 receptor binding activity and the ability to elicit the generation of cAMP. For example, when the amino acid being substituted or replaced is an acidic amino acid, (D or E) another acidic amino acid is used in the mutagenesis to produce the peptide product. To illustrate, if D6 were to be substituted, the resulting substitution would be D6E.

The twenty amino acids commonly used in protein synthesis can be divided into groups. These groups can be used to determine the possible conservative amino acid substitutions for use with the peptide of the present invention. These groups include: the aliphatic residues: alanine (A), valine (V), leucine (L), and isoleucine (I); the hydroxyl residues: serine (S) and threonine (T); the amide residues: asparagine (N) and glutamine (E); the acidic residues: aspartic acid (D) and glutamic acid (E): the basic residues: lysine (K), arginine (R), and histamine (H); the aromatic residues: phenylalanine (F), tyrosine (Y), and tryptophan (W); and the sulfur-containing residues: methionine (M) and cysteine (C).

In view of these definitions, the following conservative amino acid substitutions are contemplated by the present invention. They include: S1T, L2I, L2V, L2A, A3V, A3I, A3L, L4V, L4A, L4I, A5L, A5I, A5V, D6E, D7E, A8V, A8I, A8L, A9V, A9I, A9L, F10Y, F10W, R11K, R11H, E12D, R13K, R13H, A14V, A14I, A14L, R15K, R15H, L16V, L16I, L16A, L17V, L17I, L17A, A18V, A18I, A18L, A19V, A19I, A19L, L20I, L20V, L20A, E21D, R22K, R22H, R23K, R23H, H24R, H24K, W25Y, W25F, L26V, L26I, L26A, N27Q, S28T, Y29F, Y29W, M30C, H31R, H31K, K32R, K32H, L33V, L33I, L33A, L34V, L34I, L34A, V35I, V35L, V35A, L36V, L36I, L36A, D37E, A38V, A38I, and A38L.

Another set of mutations may be made by replacing residues with ones having quite different properties, yet which still produce a final peptide with the desired property or properties. For example, replacing one or multiple basic residues with non-basic residues may render the peptide less susceptible to proteolytic degradation.

Alternatively, modified amino acids such as norleucine can be used to produce novel PTH2 receptor binding ligands. For example, one mutation contemplated is M30 norleucine. Mutations can be made for a variety of reasons, including increasing or decreasing binding affinity, or altering the potential for oxidation damage by eliminating or replacing particular amino acid residues.

The present invention also contemplates additional peptides that possess PTH2 or PTH1 receptor binding activity and the ability to elicit or block cAMP generation. These peptides can be generated recombinantly or synthetically, or isolated from the tissues of various subject mammals, as described above. Peptides with at least 60, 70, 80, 90, 95, or 99% of their amino acid sequence identical to that of SEQ ID NO: 1 as determined by FASTA or BLAST using default opening and gap penalties and a PAM scoring matrix are also contemplated. Percent sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a predetermined portion of one or both sequences). The programs provide a "default" opening penalty and a "default" gap penalty, and a scoring matrix such as PAM 250 (a standard scoring matrix; see Dayhoff et al., in Atlas of Protein Sequence and Structure, vol. 5, supp.3 (1978) can be used in conjunction with the computer program. The percent identity can then be calculated as the total number of identical matches/length of the sequence within the matched span+number of gaps introduced into the longer sequence in order to align the two segments. Peptides that are at least 70 percent identical will typically have one or more amino acid substitutions, deletions, and/or insertions. Usually, the substitutions will be conservative so as to have little or no effect on the overall net charge, polarity, or hydrophobicity of the peptide but optionally may increase the activity of the peptide.

Analogs of the present invention include small molecules modeled on the peptides. The peptides of the present invention can be modeled to produce small molecule libraries which are screened for candidate compounds using PTH2 or PTH1 receptor binding and/or activation assays as the screening protocol. Advances in the field of combinatorial chemistry provide methods well known in the art to produce large numbers of candidate compounds that can have a binding or other effect on the PTH2 receptor. Accordingly, the screening is contemplated of small molecule libraries modeled from the peptides of the present invention for compounds with binding affinity or other activity for the PTH2 or PTH1 receptor.

Pharmaceutical Related Embodiments

The peptides, fragments, and analogs of the invention are generally administered to animals, including but not limited to mammals, e.g., humans, cattle, cats, dogs, sheep, goats, pigs, and rats.

The pharmacologically active peptides, fragments, and analogs of the invention can be processed in accordance with conventional methods of galenic pharmacy to produce medicinal agents for administration to patients, e.g., mammals including humans.

The peptides, fragments, and analogs of the invention can be employed in admixture with conventional excipients, i.e., pharmaceutically acceptable organic or inorganic carrier substances suitable for parenteral, enteral (e.g., oral) or topical application that do not deleteriously react with the active peptides, fragments, and analogs of the invention. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules. A syrup, elixir, or the like can be used wherein a sweetened vehicle is employed.

Sustained or directed release compositions can be formulated, e.g., liposomes or those wherein the active compound is protected with differentially degradable coatings, e.g., by microencapsulation, multiple coating, etc. It is also possible to freeze-dry the new compounds and use the lyophilizates obtained, for example, for the preparation of products for injection.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

The active ingredient will be administered in a daily dosage regimen from about 1.0 mg to about 400 mg, preferably from about 10 mg to about 200 mg Advantageously, equal doses will be administered two to four times per day or by continuous intravenous infusion. When the administration is carried out under the care of a physician, the effect of the PTH receptor binding peptide is to relieve the symptoms associated with a variety of PTH dysfunctional conditions.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Computer Related Embodiments

The peptide sequence provided in SEQ ID NO: 1, fragments thereof, and analogs thereto may be "provided" in at least one medium to facilitate their use as models. As used herein, provided refers to a manufacture, other than an isolated amino acid sequence, which contains an amino acid sequence of the present invention. Such a manufacture provides the amino acid sequences of the present invention in a form that allows a skilled artisan to examine the manufacture using means not directly applicable to examining the peptide, fragments, or analogs of the present invention as they exist in nature or in a purified form.

In one application of this embodiment, an amino acid sequence of the present invention can be recorded on computer readable media. As used herein, "computer readable media" refers to any medium that can be read and accessed directly by a computer. Such media include, but are not limited to: magnetic storage media, such as floppy disks, hard disks storage medium, and magnetic tape; optical storage media such as CD-ROM; electrical storage media such as RAM and ROM; and hybrids of the categories such as magnetic/optical storage media. A skilled artisan can readily appreciate how any of the presently known computer readable mediums can be used to create a manufacture comprising computer readable medium having recorded thereon an amino acid sequence of the present invention.

As used herein, "recorded" refers to a process for storing information on computer readable medium. A skilled artisan can readily adopt any of the presently known methods for recording information on computer readable medium to generate manufactures comprising the amino acid sequence information of the present invention.

A variety of data storage structures are available to a skilled artisan for creating a computer readable medium having recorded thereon an amino acid sequence of the present invention. The choice of the data storage structure will generally be based on the means chosen to access the stored information. In addition, a variety of data processor programs and formats can be used to store the amino acid sequence information of the invention on computer readable medium. The sequence information can be represented in a word processing text file, formatted in commercially-available software, or represented in the form of an ASCII file, stored in a database application, such as DB2, Sybase, or the like. A skilled artisan can readily adapt any number of dataprocessor structuring formats (e.g. text file or database) in order to obtain computer readable medium having recorded thereon the amino acid sequence information of the present invention.

By providing the amino acid sequences of the present invention in computer readable form, a skilled artisan can routinely access the sequence information for a variety of purposes. Computer software is publicly available that allows a skilled artisan to model peptide structures based in part on sequence information.

Structural information (such as crystal structure coordinates, nuclear magnetic resonance information, etc.) based on the amino acid sequences of the present invention as well as structural information of the PTH receptor can be used by this software to model the interactions of the amino acid sequences of the present invention and the PTH receptor. This modeling function would permit a skilled artisan to localize portions of a PTH receptor ligand to serve as a model for the generation of small molecules and the like. These small molecules are contemplated for use as agonists and antagonists of the PTH receptor.

As used herein, "a computer-based system" refers to the hardware means, software means, and data storage means used to analyze the amino acid sequence information of the present invention. The minimum hardware means of the computer-based system of the present invention comprises a central processing unit (CPU), input means, output means, and data storage means. A skilled artisan can readily appreciate that any one of the currently available computer-based system are suitable for use in the present invention.

As stated above, the computer-based systems of the present invention comprise data storage means having stored therein an amino acid sequence of the present invention and the necessary hardware means and software means for supporting and implementing a search means. As used herein, "data storage means" refers to memory that can store amino acid sequence information of the present invention, or a memory access means that can access manufactures having recorded thereon the amino acid sequence information of the present invention.

As used herein, "search means" refers to one or more programs that are implemented on the computer-based system to compare a candidate sequence with the sequence information stored within the data storage means. Search means are used to identify structural domains that match the structural motifs involved in binding and/or activating the PTH receptor. A skilled artisan can readily recognize that any one of the available implementing software packages for conducting domain searches can be adapted for use in the present computer-based systems.

As used herein, a "candidate sequence" can be any amino acid sequence of two or more amino acids, more likely three or more. A skilled artisan can readily recognize that the longer a candidate sequence is, the less likely a candidate sequence will be present as a random occurrence in the database.

The following examples are not limiting, but are merely illustrative of the compositions and methods of this invention. Additionally, reference to PTH2 receptor binding by particular ligands described below may also imply an attendant stimulating activity of these ligands.

EXAMPLES

Particular aspects of the invention may be more readily understood by reference to the following examples, which are intended to exemplify the invention, without limiting its scope to the particular exemplified embodiment.

Distribution of the PTH2 Receptor

The PTH2 receptor is a G-protein coupled receptor selectively activated by parathyroid hormone (PTH) (Behar V, Pines M, 137:2748–57 (1996); Gardella, et al., J Biol Chem 271:19888–19893 (1996)), which was identified in a homology based screen, using common sequences within the secretin (Type II) family of G-protein coupled receptors. Usdin, et al., J Biol Chem 270:15455–15458 (1995). It is most similar in sequence and ligand recognition specificity to the PTH/PTHrP (PTH1) receptor (Abou-Samra, et al., Cell Biology 89:2732–2736 (1992); Juppner, et al., Science 254:1024–1026 (1991)). Upon amino acid sequence alignment the PTH2 and PTH1 receptors have about 50% identity. Both are activated by PTH but only the PTH1 receptor is activated by parathyroid hormone-related protein (PTHrP). Studies of PTH action had not predicted the existence of the PTH2 receptor. The PTH1 receptor is expressed at high levels in the kidney and skeleton where it most likely mediates the effects of PTH on calcium homeostasis. Its mutation in Jansen's disease or in transgenic mice demonstrates a critical role in skeletal development. Schipani, et al., Science 268:98–100 (1995); Lanske, et al., Science 273:663–6 (1996). PTH has effects at sites outside the kidney and bone including the vasculature, heart and pancreas. el-Shahawy, et al., Nephron 57:69–74 (1991); Fadda, et al., Am J Physiol 258:E975–84 (1990); Geiger, et al., Am J Nephrol 12:259–64 (1992); Massry, et al., Miner Electrolyte Metab 21:13–28 (1995). Since Northern blot and RT-PCR analysis indicate a near ubiquitous distribution for the PTH1 receptor it could be responsible for the effects of PTH in most tissues. (Urena, et al., Endocrinology 133: 617–23 (1993); Tian, et al., Am. J. Nephrology 13:210–213 (1993)). Most of the effects of PTH are also produced by PTHrP, and locally produced PTHrP is thought to be the endogenous messenger at many sites where PTH effects are observed. Philbrick, et al., Physiol Rev 76:127–73 (1996). Some effects of PTH appear to be mediated by receptors with ligand specificity or second messenger coupling different from the PTH/PTHrP receptor. Those described to date (Inomata, et al., Endocrinology 136:4732–40 (1995); Kovacs, et al., Proc Natl Acad Sci USA 93:15233–8 (1996)) do not correlate well with the properties of the PTH2 receptor established in transfected tissue culture cells. Thus, considerably more investigation is required to, determine the physiological role of the PTH2 receptor. Knowledge of the tissues and cells where the PTH2 receptor is expressed will provide an important guide for experiments investigating its function.

Northern blots show that PTH2 receptor mRNA is most abundant in the brain and that is also present in lung, pancreas, placenta and testis. Usdin, et al., Journal of Biological Chemistry 270:15455–15458 (1995). In situ hybridization histochemistry reveals that many more tissues express PTH2 receptor mRNA, and that it is expressed by distinct and often quantitatively minor cell populations within those tissues. Usdin, et al., Endocrinology 137: 4285–97 (1996). In the cardiovascular system it is expressed by vascular endothelium and smooth muscle, endocardium, and myocardium. In the gastrointestinal tract scattered cells which, based on morphology and distribution, appear to be mucous producing cells and endocrine cells express PTH2 receptor mRNA. In the testis it is expressed by sperm, especially within the head of the epididymis, and it is also present within some ovarian follicles. Within the kidney its mRNA was detected within a very small number of cells near the vascular pole of glomeruli.

The Example below discusses the development of an antibody specifically recognizing the PTH2 receptor. It was thought important to confirm that the PTH2 receptor protein was expressed by cells where its mRNA was previously detected, since protein expression does not necessarily parallel that of the mRNA encoding it. Labeling with the antibody also led to detection of cells not previously known to express the PTH2 receptor, and double labeling contributed to their identification.

Example 1

Antibody Production

Rabbits were immunized with the synthetic peptide RQIDSHVTI-PGYVWSSSEQDC (SEQ ID NO: 113) conjugated to keyhole limpet hemocyanin (synthesized and conjugated by the biopolymer synthesis facility at Massachusetts General Hospital, Boston, Mass.). This peptide corresponded to residues 480 to 500 of the rat PTH2 receptor (Genbank Entry U55836), which are located within the intracellular C-terminus of the receptor.

Immunoglobulin G (IgG) produced from the immunized rabbits was purified from the serum using protein A Sepharose (Pharmacia; Piscataway, N.J.). The antibody preparation was then affinity purified as described in Harlow & Lane, Cold Spring Harbor: Cold Spring Harbor Laboratories, after coupling 0.5 mg of the antigen peptide to Sulfolink gel (Pierce; Rockford, Ill.) according to the manufacturer's protocol. Protein A or affinity purified antibody was used at a final concentration of approximately 0.3–0.4 micrograms/ml.

Example 2

Antibody Specificity

HEK293 cells stably expressing the human PTH1 or PTH2 receptor have previously been briefly described in Usdin, *Endocrinology* 138:831–838 (1997). Incubation with 1 μM PTH produced an approximately 50-fold stimulation of cAMP accumulation in either cell line, 1 μM PTHrP produces similar stimulation in only the PTH1 receptor expressing cells, and there was no significant stimulation by either peptide in non-transfected HEK293 cells. Saturation analysis using binding of $^{125}$I-rPTH(1–34) to membranes prepared from these cells indicates a receptor density of approximately 1 pmole/ng protein in each cell line.

Cells expressing the human PTH2 receptor sequence were used to evaluate the purified antibodies described in Example 1. The deduced rat and human receptor sequences differ at only 3 out of the 21 amino acids in the sequence used to generate the antibody, so cells expressing the cloned human receptor were thought to mediate a satisfactory screening protocol. Antibodies from two rabbits immunized with the synthetic peptide produced strong labeling of HEK293 cells stably expressing the human PTH2 receptor, detected either with a fluorescent secondary antibody or a horseradish peroxidase coupled secondary antibody. Pre-immune serum did not label the PTH2 receptor expressing cells and no labeling of either the parent HEK293 cells or HEK293 cells stably expressing the human PTH1 receptor, which should express the same endogenous epitopes as the parent cells, was detected. Similarly, there was intense labeling of 20–30% of COS-7 cells transfected with PTH2 receptor cDNA but no labeling of cells in mock transfected cultures.

Several bands were labeled in western blots of PTH2 receptor enriched membranes, probably representing a combination of multiple glycosylation states and aggregation or oligomerization of the receptor when analyzed by western blot analysis. For western blots, P2 membranes were prepared from confluent plates of HEK293 derived cell lines. Pellets were suspended directly in gel loading buffer or first digested with PNGase F (New England Biolabs, Beverly Mass.) according to supplier's protocol. Electrophoresis and transfer to nitrocellulose membranes were performed according to the protocols supplied with the 10% Nu-PAGE gels and transfer buffer (Novex; San Diego, Calif.). Membranes were stained with Ponceau-S to verify even transfer of proteins from the gel, the positions of molecular weight standards marked, membranes blocked by incubation in Blotto for 60 minutes followed by incubation with primary antisera, and then horseradish peroxidase coupled secondary antibody for one hour diluted in Blotto. Antibody binding was detected using enhanced chemiluminescence (SuperSignal Ultra; Pierce, Rockford, Ill.).

The highest mobility major band migrated with an apparent molecular weight of 84 kd, consistent with the size of a band labelled with a radioactive photoaffinity PTH2 receptor ligand. Behar, et al., *Endocrinology* 137:2748–57 (1996). Following digestion with PNGase F, the mobility of the high mobility major band increased to an apparent molecular weight of 63 kD, consistent with the predicted size of the protein based on its cDNA sequence. No signal was seen in membranes prepared from the parent HEK293 cells or ones expressing the PTH1 receptor. The limited sequence identity between the antigen and the rat PTH1 receptor was identical to that with the human PTH1 receptor, and no significant labeling was detected in rat kidney tubules. Absorption of the antibody with the peptide used to generate it eliminated tissue labeling and specific staining was absent when pre-immune serum was used to label tissue.

Example 3

Immunohistochemical and In situ Hybridization Analysis of Various Rat Tissues

Immunostaining protocols and reagents are described in detail on the world wide web (intramural.nimh.nih.gov, on Protocols page). Standard indirect immunofluorescence or avidin-biotin horseradish peroxidase histochemistry (ABC) was performed on 4% paraformaldehyde perfused 12 gm thick cryostat sectioned tissue. A few sections were made from tissue frozen and sectioned before fixation. This material was post-fixed in 4% paraformaldehyde. Tissue was obtained from 150–200 gm Sprague-Dawley rats or rat embryos of noted ages, except for mouse bone. Fixed, decalcified, paraffin sectioned mouse femur was obtained from Molecular Histology Laboratories (Rockville, Md.), deparaffinized in xylene and then rehydrated through decreasing concentrations of ethanol and incubated in phosphate buffered saline prior to labeling, as performed for other tissues.

Tissue culture cells were grown on glass coverslips, rinsed briefly with PBS, fixed for 10 minutes in 4% formaldehyde, rinsed extensively with PBS, and then incubated with primary and secondary antibodies as described above for tissue. Absorbed (control) antibody solution was prepared by incubating antibody diluted to the working concentration overnight at 4° C. in blocking buffer containing 1 microgram/ml peptide antigen (not conjugated to keyhole limpet hemocyanin).

The in situ hybridization data presented herein are from detailed reexamination of material generated in a previous study reported in Usdin, et al., *Endocrinology* 137:4285–97 (1996).

Fluorescent secondary antibodies were indocarbocyanine (Cy3), fluorescein isothiocyanate (FITC), or aminomethylcoumarin acetate (AMCA) conjugates of donkey immunoglobulin prepared for multiple labeling (Jackson Immunoresearch Labs; West Grove, Pa.). Labeling with horseradish peroxidase used Vectastain ABC elite reagents (Vector Laboratories, Burlingame Calif.). Antibody 10A8 recognizing MG160 (a Golgi selective marker) (Gonatas, et al., *J Biol Chem* 264:646–53 (1989) [published erratum appears in *J Biol Chem* 1989 Mar. 5;264(7):42641]; Gonatas, et al., *J Cell Sci* 108:457–67 (1995)) used at 1:100) was a gift of Nicholas K. Gonatas (University of Pennsylvania). Mouse monoclonal antibody to caveolin-3 (used at 1 microgram per ml) was from Transduction Laboratories (Lexington, Ky.).

Rat monoclonal antibody to somatostatin was from Pharmingen (San Diego, Calif.). Rabbit antibody to somatostatin (used at 1:400) was from Incstar Corp. (Stilwater, Me.). Guinea pig antibody to insulin (used at 1:2,000) was from Incstar. Rabbit antibody to histidine decarboxylase (used at 1:2,000) was from Euro-Diagnostica (Malmo, Sweden).

The results for various tissue types are discussed below.

Pancreas

Some, but not all, of the cells located in the outer rim of pancreatic islets were strongly labeled by the PTH2 receptor antibody. This distribution of labeled cells is characteristic of several non-insulin producing islet cell types. Double labeling shows that the PTH2 receptor positive cells were somatostatin producing cells. There was precise coincidence of labeling by PTH2 receptor and somatostatin directed antibodies, but no overlap between the PTH2 receptor positive cells and antibody staining for insulin, pancreatic polypeptide, or glucagon, which are present in distinct cells. Bauer EG, In Cell and Tissue Biology, A Textbook of Histology. Urban and Schwarzenberg, Baltimore, 737–750 (1988); Baskin, et al., *Anat Rec* 208:567–78 (1984); Hunyady, et al., *Endocrinology* 138:2632–5 (1997)).

An earlier study of PTH2 receptor mRNA distribution (Usdin, et al., *Endocrinology* 137:4285–97 (1996)), did not report expression of the receptor in pancreatic islets. In that earlier study there was less probe hybridization over islets than over exocrine tissue. This observation lead to the suggestion that pancreatic islets did not contain PTH2 receptor mRNA. However, on reexamination of slides from that study, a small number of clearly labeled cells were indeed apparent on the rim of islets in a position corresponding to the PTH2 receptor antibody labeling.

Viewed through the microscope there also appeared to be labeling of cells in the exocrine pancreas. This labeling was very weak and difficult to unequivocally document, but it was blocked by absorption of the antibody with the antigenic peptide. Labeling of exocrine as well as endocrine pancreatic cells was quite clear in embryos, providing additional support for the suggestion of low-level persistence of exocrine expression of the PTH2 receptor in adult rats.

Thyroid Gland

Parafollicular cells within the thyroid gland were labeled by the PTH2 receptor antibody. They comprise a numerically minor population of cells within the thyroid gland and, like the D-cells in pancreatic islets, were not obvious following in situ hybridization. When slides from the previous in situ hybridization study were reexamined, increased grain density over cells with the distribution of parafollicular cells was observed. Double labeling with antibodies against somatostatin and against the PTH2 receptor demonstrated that many of the cells labeled by PTH2 receptor antibody contain somatostatin.

Gastrointestinal System

Several types of cells in the gastrointestinal tract were labeled by the PTH2 receptor antibody. Mucin producing cells, identified by their characteristic morphology and distribution, were labeled in the gastric epithelium. In situ hybridization previously demonstrated labeling of additional cells which seemed likely to be endocrine cells, based on their frequency and location within the epithelium. Double labeling experiments confirmed the identity of mucin-producing cells and endocrine cells in gastric epithelium. There was partial overlap between labeling by the PTH2 receptor antibody and labeling by an antibody against somatostatin. There was also co-localization of labeling by an antibody to histidine decarboxylase, which has recently been established as a marker for gastrin secreting cells (Hunyady, et al., *Endocrinology* 139:4404–15 (1998)), and the PTH2 receptor antibody. In addition, parasympathetic ganglion cells in the submucosal and myenteric plexuses were distinctly labeled by the antibody throughout the gastrointestinal tract.

Cardiovascular System

The PTH2 receptor directed antibody labeled cells throughout the cardiovascular system, including vascular endothelium and smooth muscle, consistent with previous in situ hybridization data. Strong labeling of cells in all parts of the heart was particularly dramatic. Much of the antibody labeling had a punctate distribution on or within cardiac muscle cells. These could represent localized domains of high concentration on the cell surface, or accumulation within intracellular organelles. The PTH2 receptor labeling was distinct from the Golgi marker MG160. Labeling of caveolin-3 was used to define the sarcolemma. Song, et al., *J Biol Chem* 271:15160–5 (1996). At the resolution afforded by confocal microscopy the PTH2 receptor accumulations appeared to be within the plane of the plasma membrane of cardiac myocytes. Much of the labeling seemed to be associated with cell junctions, and could be within intercalated disks, although this observation requires confirmation using additional markers or immunoelectronmicroscopy.

Labeling of vasculature in most tissues, including embryonic aorta, by the PTH2 receptor antibody was consistent with previous observations made using in situ hybridization.

Bone and Cartilage

Chondrocytes in tracheal cartilage were clearly and intensely labeled by the PTH2 receptor antibody. Bone has relatively high autofluorescence and endogenous peroxidase activity, but the use of affinity purified PTH2 receptor antibody allowed detection of specific labeling of cells within bone. The labeling had a punctate pattern, similar to that seen for labeling by this antibody in other tissues, and the punctate labeling was eliminated by absorption of the antibody with the peptide antigen. In contrast, tissue autofluorescence generally has a more homogeneous appearance. Based on their distribution, the labeled cells appeared to primarily be chondrocytes in the growth plate and subarticular cartilage. Expression was particularly strong in developing bone.

Kidney

Using in situ hybridization histochemistry previously observed one or two cells expressing PTH2 receptor mRNA near the vascular pole of glomeruli. The same pattern of staining was seen with the PTH2 receptor recognizing antibody, and in this case the signal to noise ratio was much better.

Other Tissues

PTH2 receptor labeling in other tissues generally confirmed the distribution previously determined from in situ hybridization histochemistry. Usdin, et al., *Endocrinology* 137:4285–97 (1996). The most intense labeling was of neurons was seen within a limited number of nuclei in the brain, as demonstrated by in situ hybridization. There was no labeling in the pituitary gland by the PTH2 receptor antibody. There appeared to be weak labeling of a small population of cells within the adrenal medulla. There was also weak labeling throughout the zona glomerulosa of the adrenal cortex. Within the parathyroid gland a very minor population of cells, which may be oxyphils, appeared to be weakly labeled by the PTH2 receptor antibody, and a similar labeling pattern was seen following in situ hybridization. PTH2 receptor antibody labeling was present in pulmonary bronchioles, some cells within both the white and red pulp in the spleen, and supporting cells (not neurons) in sympathetic ganglia. PTH2 receptor protein was detected in the testis and epididymis with the same general pattern as previously observed for expression of PTH2 receptor mRNA. However, the intensity of the antibody staining, relative to the intensity of the in situ hybridization signal in the testis, was lower than that in other organs.

Example 4

Functional Expression of Human and Rat PTH2 Receptors

The detailed anatomical investigation of the PTH2 receptor in the Examples above was performed using rat tissue and mouse bone. When interpreting this data, it is important to consider that the pharmacological characterization of the PTH2 receptor has been performed using the cloned human receptor, but most studies of the physiological responses were done in rats. It is therefore important to determine the pharmacological profile of the rat PTH2 receptor.

A second reason for investigating the ligand activation specificity of the rat PTH2 receptor emerged during the characterization of the human receptor. [Nle$^{8,18}$, Tyr$^{34}$]bPTH(3–34) caused significant activation of the human PTH2 receptor under conditions where no effect on the human PTH 1 receptor was observed. This ligand was originally described as a PTH receptor antagonist based on its effects in vitro. Rosenblatt, et al., *J Biol Chem* 252: 5847–51 (1977); Seare, et al., *J Biol Chem* 254:6980–6 (1979). In vivo studies, however, suggested that it was a weak PTH receptor agonist. Cray, et al., *Br I Pharmacol* 76:259–63 (1982). The relatively large effect on the human PTH2 receptor led to the investigation of its ligand(s) on the effect on the rat PTH2 receptor to test the possibility that the previously observed effects of [Nle$^{8,18}$, Tyr$^{34}$]bPTH(3–34) in vivo could reflect actions mediated by the PTH2 receptor.

The relatively abundant expression of the PTH2 receptor in the brain, in combination with the inability to detect PTH mRNA in the brain, suggested the presence of another PTH2 receptor activating ligand. Usdin, *Endocrinology* 138:831–838 (1998). The Examples below describe purification, characterization, and use of a novel peptide TIP39 from bovine hypothalamic extracts as a likely endogenous ligand of the PTH2 receptor.

To express rat PTH2 receptor in cell culture, a rat hypothalamus cDNA library was prepared in the vector CDM7 amp as described. Aruffo & Seed, *Proc Natl Acad Sci USA* 84:8573–8577 (1987). Miniprep DNA from 47 pools of 20,000 clones per pool was screened by PCR with rat PTH2 receptor-specific primers (amplifying bases 1069 to 1908, GenBank #U55836). Positive pools were re-screened with a sense vector sequence primer and an antisense primer in the 5' end of the receptor sequence (bases 659 to 679) and then by Southern blotting of an EcoRI-digest, using a $^{32}$P labeled probe (bases 1069–1908). A clone was isolated from a single positive pool by colony hybridization using the same $^{32}$P labeled probe. Both strands were sequenced as previously described (Usdin, et al., *Endocrinology* 133:2861–2870 (1993)) following subcloning of restriction fragments into pUC18 vector.

COS-7 cells were grown and transfected as previously described (Clark, et al., *Mol Endocrinol* 12:193–206 (1998)) except that transfections were performed in 10 cm tissue culture dishes using 10 µg of plasmid DNA. Cell culture supplies were obtained from Life Technologies (Frederick, Md.) except for fetal bovine serum which was from Sigma (St. Louis, Mo.). Bovine hypothalamic extract was prepared by acid extraction, gel-filtration and reverse-phase HPLC as previously described (Usdin, *Endocrinology* 138:831–838 (1998)) and discussed below in Examples.

The cells were transferred following trypsinization to 96-well plates at a density of 50,000 cells/well the following day. The constructs containing the cDNA sequences of the human PTH2 receptor and β-galactosidase have been previously described. Usdin, et al., *J Biol Chem* 270:15455–15458(1995); Usdin, et al., *Biotechniques* 14:222–224 (1993).

Figure 1:
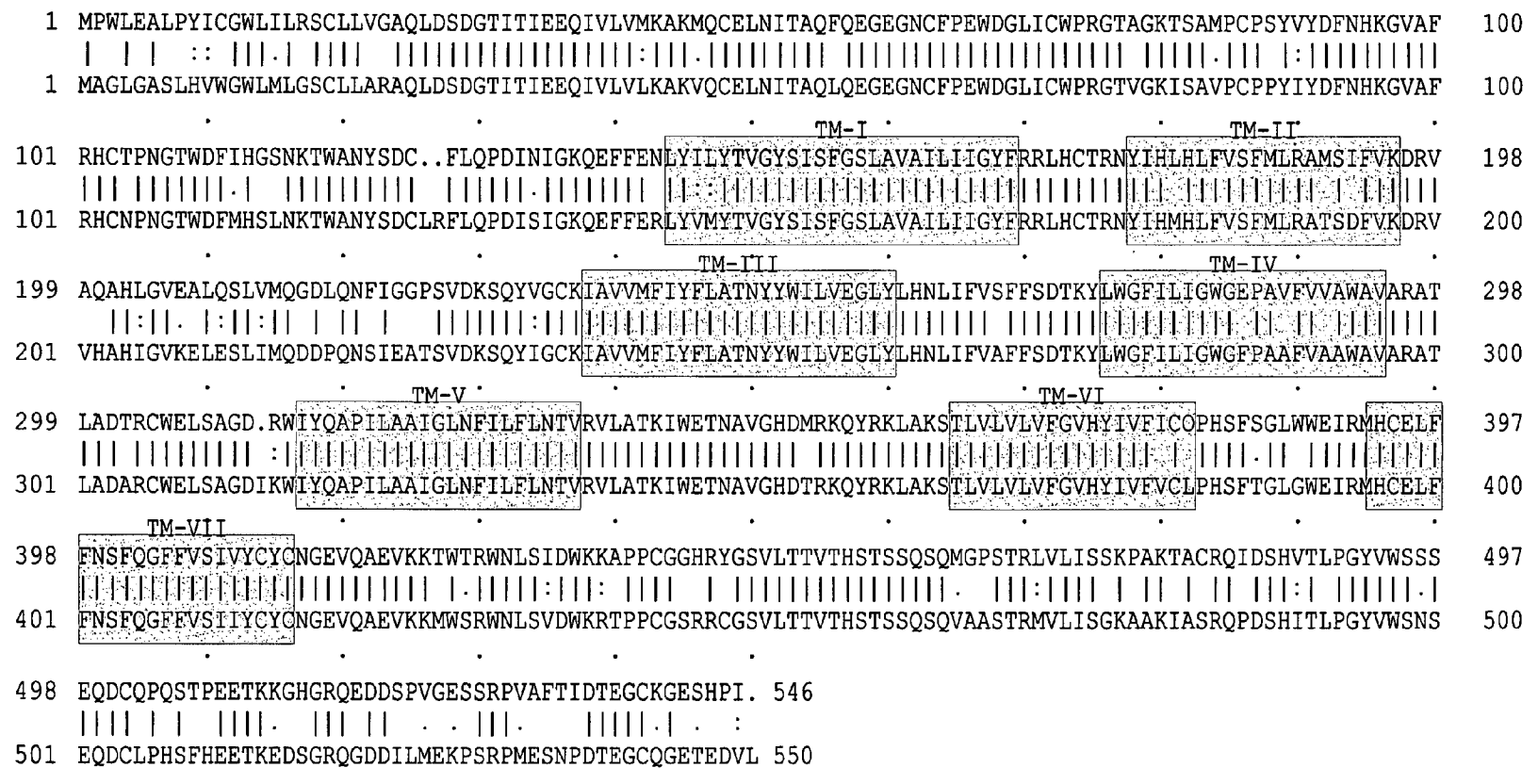
Figure 2B:
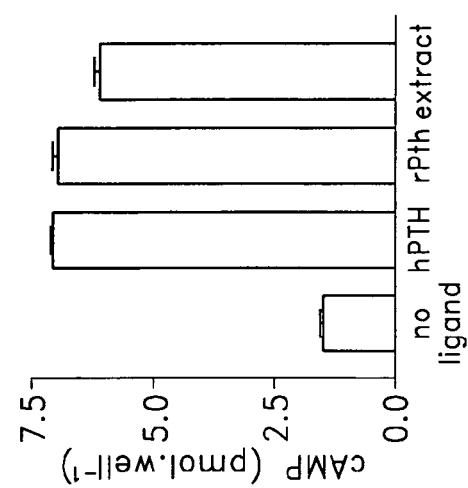
Figure 2A:
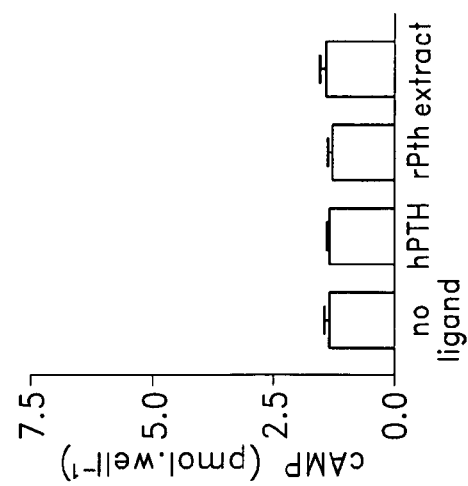

The sequence of the rat PTH2 receptor was previously determined from a partial length cDNA clone and the product of a RT-PCR reaction. Usdin, et al., *Endocrinology* 4285–4297 (1996). For this study a cDNA clone containing the entire coding sequence of the receptor was obtained by screening a rat hypothalamic cDNA library with a probe derived from the 5' end of that sequence. There is 100% sequence identity between the independently derived sequences. The new 2.4 kb clone contains 28 bases of 5' untranslated sequence, 655 bases of 3' untranslated sequence and 1.7 kb of coding sequence. On alignment (FIG. 1) the deduced amino acid sequence is 82% identical to the human PTH2 receptor sequence. When the rat PTH2 receptor clone was introduced into COS-7 cells it was activated by PTH (FIG. 2C), but the response to a high concentration of either rat or human PTH(1–34) was much less than that of the human PTH2 receptor (FIG. 2B). In contrast, the bovine hypothalamic extract enriched in PTH2 receptor stimulating activity caused a larger increase in cAMP than the PTH peptides (FIG. 2C) and this stimulation was approximately equal to the effect produced by the same amount of extract at the human PTH2 receptor (FIG. 2B). None of the ligands produced a detectable stimulation of adenylyl cyclase activity in cells transfected with β-galactosidase (FIG. 2A).

Example 5

Agonist Pharmacology of Human and Rat PTH2 Receptors

COS-7 cells prepared according to Example 4 were prepared for use in this Example. Following removal of medium, transfected COS-7 cells were treated for 40 min at 37° C. with 50 µl/well cAMP assay buffer (Dulbecco's modified Eagle's medium containing 25 mM HEPES supplemented with 0.1% bovine serum albumin, 30 µM Ro 20–1724 (RBI, Natick, Mass.), 100 µM (4-(2-aminoethyl))-benzenesulfonylflouride and 1 µg/ml bacitracin). This buffer was removed and replaced with 40 µl fresh buffer. Test agents were added in a volume of 10 µl and the cells incubated for an additional 40 min at 37° C. All peptides were purchased from either Bachem (Torrance, Calif.) or Peninsula Laboratories (Belmont, Calif.). The letters 'b,' 'r' and 'h' designate the peptide sequence as bovine, rat and human, respectively. [$^{125}$I]cAMP was obtained from NEN (Boston, Mass.). [α-$^{32}$P]dCTP was purchased from ICN Biomedicals (Costa Mesa, Calif.). Bovine hypothalamic extract was prepared by acid extraction, gel-filtration and reverse-phase HPLC as previously described. Usdin, *Endocrinology* 138:831–838 (1998). The assay was then terminated by the addition of 50 µl 0.1 N HCl, 0.1 mM CaCl$_2$. A 25 µl assay volume was used for assays of the activity of bovine hypothalamic extract and parallel assays of PTH ligands. cAMP was quantified using a RIA as previously described. Clark, et al., *Mol Endocrinol* 12:193–206 (1998). Antagonist inhibitory potency was examined by measuring the concentration-dependence of rPTH(1–34)-stimulated cAMP accumulation in the presence and absence of antagonist.

Data Analysis

Concentration-dependence data for ligand-stimulated cAMP accumulation was analyzed using the following four parameter-logistic equation using Prism 2.01 (GraphPad Software Incorporated).

$$cAMP = min + (max - min)/(1.0 + 10^{(Log\ EC50 - X)n})$$

where X is the logarithm of the ligand concentration, min is the cAMP level in the absence of ligand, max is the maximum level produced and n is the Hill slope. Statistical comparison of two sample means was evaluated using the two-tailed Student's t-test. Statistical comparison of multiple means was performed initially by single-factor analysis of variance followed by post-hoc analysis with the Newman-Keuls test. Antagonist inhibitory potency was quantified using the $pA_2$, value, the negative logarithm of the concentration of antagonist that produces a two-fold decrease of agonist $EC_{50}$. This was calculated using the following equation:

$$pA_2 = ((EC_{50}/EC_{50}') - 1) - \log[antagonist]$$

where $EC_{50}'$ is the agonist $EC_{50}$ in the presence of the antagonist.

The surprisingly small response to PTH(1–34) by the rat PTH2 receptor (FIG. 2) led us to further exploration of the effects of PTH-based ligands on cAMP accumulation. The pharmacology of the rat PTH2 receptor was compared with that for the human PTH2 receptor. Rat and human PTH (1–84) were included in this evaluation since the full-length peptide has been identified as a bioactive circulating form of the hormone. A preliminary experiment was conducted to determine the dependence of the response to rPTH(1–34) on the amount of DNA in the transfection. The response increased with increasing amounts of DNA but was maximal at 3 μg and 10 μg per 10 cm plate for both receptors. The latter amount was used in all subsequent experiments.

Figure 3A:
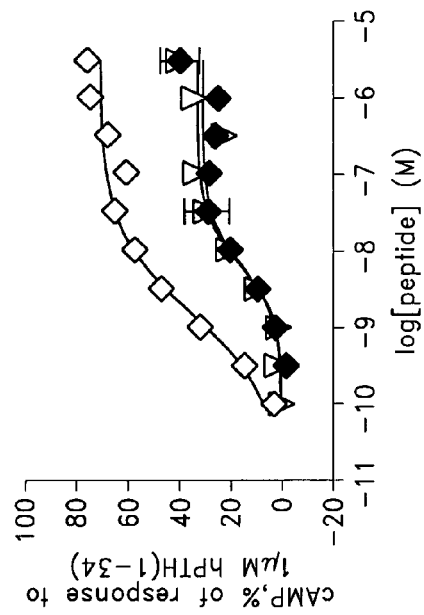
FIG. 3. Pharmacological characterization of human and rat PTH-2 receptors expressed in COS-7 cells. Transient expression in COS-7 cells was performed with plasmids encoding the human PTH2 receptor (A, C) and the rat PTH2 receptor (B, D). Total cAMP was measured. A, B—Activation of PTH2 receptors by rat and human PTH ligands and by a PTHrP analogue (○—rPTH(1–34); ●—rPTH(1–84); Δ—hPTH(1–34); (solid triangle)—hPTH(1–84); ×PTHrP (1–34)). C, D—Effect of bovine PTH ligands on cAMP accumulation ((open diamond)-[Nle$^{8,18}$, Tyr$^{34}$]bPTH(1–34); (solid diamond)-[Nle$^{8,18}$, Tyr$^{34}$]bPTH(3–34); ∇—bPTH (3–34)). The data are presented as the cAMP produced as a percentage of the response to a maximally-stimulating concentration of the reference ligand (hPTH(1–34) for the human PTH2 receptor and rPTH(1–34) for the rat PTH2 receptor). Ligand-specific cAMP accumulation was divided by that for the reference agonist (which was assayed in parallel with each ligand) and converted to a percentage. Data represent the mean±range of duplicate measurements. The experiments were repeated two or three times, except for the assays for [Nle$^{8,18}$, Tyr$^{34}$]bPTH(3–34) and bPTH (3–34) at the rat receptor which were repeated once.

At the human PTH2 receptor all PTH ligands containing the N-terminal amino acid stimulated cAMP accumulation (FIG. 3A). The highest potencies ($EC_{50}$ of 1 nM or less) were observed for rPTH(1–34), rPTH(1–84) and hPTH (1–34). For hPTH(1–34) a similar potency was observed in previous studies. hPTH(1–84) and [Nle$^{8,18}$, Tyr$^{34}$]bPTH (1–34) were slightly less potent and activated the receptor with a lower intrinsic activity (Table 3). Strikingly, at the rat PTH2 receptor all PTH ligands were considerably less potent than at the human receptor (FIG. 3, Tables 3 and 4). The highest potency observed was only 19 nM (for rPTH (1–84), Table 4). For all other PTH ligands the $EC_{50}$ was approximately 100 nM (Table 4). Lower potency at the rat receptor was specific to PTH ligands since PTHrP(1–34) displayed a 14-fold higher potency for the rat receptor than the human receptor (Tables 3 and 4). PTHrP(1–34) acted with low intrinsic activity at both receptors (Tables 3 and 4). A range of intrinsic activity was observed for PTH ligands at the rat PTH2 receptor (Table 3). For all PTH and PTHrP ligands the maximal stimulation of cAMP production was less at the rat PTH2 receptor compared with the human receptor (compare column 4 of Table 4 with column 3 of Table 3).

TABLE 3

Pharmacological characterization of the human PTH2 receptor

| Ligand | $-\log EC_{50}$ ($EC_{50}$ nM) | $E_{max}$, % of response to 1 μM hPTH(1-34) |
|---|---|---|
| hPTH(1-34) | 8.95 ± 0.09 (1.1) | 100 |
| hPTH(1-84) | 8.26 ± 0.14 (5.5) | 79 ± 1 |
| rPTH(1-34) | 9.39 ± 0.10 (0.41) | 94 ± 7 |
| rPTH(1-84) | 9.24 ± 0.05 (0.58) | 98 ± 4 |
| [Nle$^{8,18}$, Tyr$^{34}$]bPTH(1-34) | 8.41 ± 0.16 (3.9) | 76 ± 7 |
| [Nle$^{8,18}$, Tyr$^{34}$]bPTH(3-34) | 8.28 ± 0.05 (5.2) | 37 ± 3 |
| bPTH(3-34) | 8.05 ± 0.06 (8.9) | 38 ± 7 |
| PTHrP(1-34) | 6.03 ± 0.15 (930) | 25 ± 3 |
| Extract | NA | 77 ± 2 |

The potency ($-\log EC_{50}$) and intrinsic activity ($E_{max}$) of ligands were measured for activation of adenylyl cyclase activity in COS-7 cells transiently expressing the receptor. Intrinsic activity was defined as the maximal stimulation by a ligand divided b the reponse to any maximally-stimulating concentration of hPTH(1-34) (1 μM) which was assayed in parallel for each agonist. For hPTH(1-34) the maximal ligand-stimulated cAMP production was 4.0 ± 0.4 pmol.well$^{-1}$ A slightly greater response (6.0 ± 0.6 pmol.well$^{-1}$) was observed when the ligand was assayed in parallel with the extract, for which a smaller assay volume was used (25 μl). Data are mean ± standard error of the mean of three or four experiments. Figures in brackets are meaning $EC_{50}$, nM. NA-not applicable.

TABLE 4

Pharmacological characterization of the rat PTH2 receptor.

| Ligand | $-\log EC_{50}$ ($EC_{50}$ nM) | $E_{max}$, % of response of rPTH2r to 3 μM rPTH(1-34) | $E_{max}$, % of response of hPTH2r to 1 μM hPTH(1-34) |
|---|---|---|---|
| hPTH(1-34) | 6.85 ± 0.29 (140) | 43 ± 4 | 22 ± 7 |
| hPTH(1-84) | 6.98 ± 0.21 (110) | 42 ± 5 | 15 ± 4 |
| rPTH(1-34) | 7.09 ± 0.16 (81) | 100 | 46 ± 11 |
| rPTH(1-84) | 7.72 ± 0.12 (19) | 97 ± 5 | 28 ± 4 |
| [Nle$^{8,18}$, Tyr$^{34}$]bPTH(1-34) | 6.85 ± 0.20 (141) | 19 ± 3 | 5 ± 1 |
| [Nle$^{8,18}$, Tyr$^{34}$]bPTH(3-34) | NR | NR | NR |
| bPTH(3-34) | NR | NR | NR |
| PTHrP(1-34) | 7.17 ± 0.14 (68) | 14 ± 1 | 7 ± 3 |
| Extract | NA | 220 ± 34 | 88 ± 8 |

The potency ($-\log EC_{50}$) and intrinsic activity ($E_{max}$) of ligands were measured for activation of adenylyl cyclase activity in COS-7 cells transiently expressing the receptor. Intrinsic activity was defined as the maximal stimulation by a ligand divided by the reponse to a maximally-stimulating concentration of rPTH(1-34) (3.2 μM) which was assayed in parallel for each agonist. For rPTH(1-34) the maximal ligand-stimulated cAMP production was 2.1 ± 0.4 pmol.well$^{-1}$ for 50 μl-volume assays. The maximal response of ligands was also compared with the maximal response of the human PTH2 receptor to 1 μM hPTH(1-34) (the most efficacious agonist at the human receptor). This response was measured in parallel for each agonist. Data are mean ± standard error of the mean of three or four experiments. Figures in brackets are meaning $EC_{50}$, nM. NA-not applicable. NR-no detectable response (see text for details).

Figure 3C:
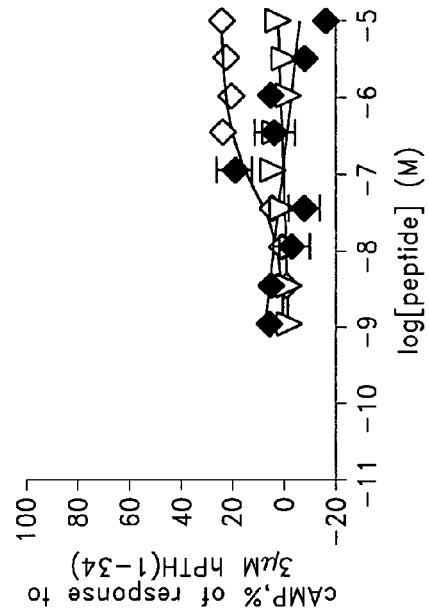
Figure 3B:
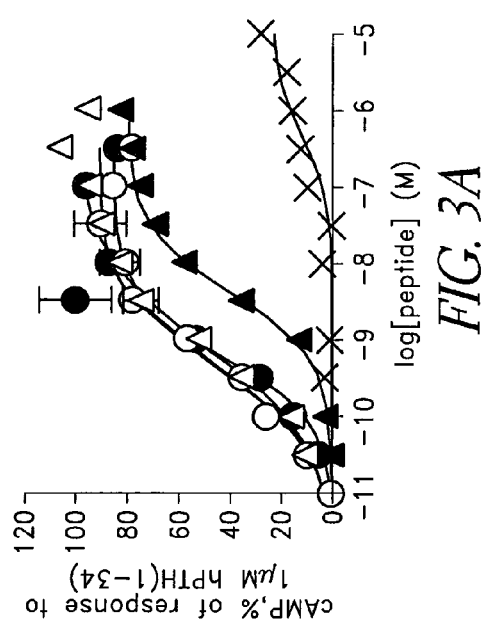
Figure 3D:
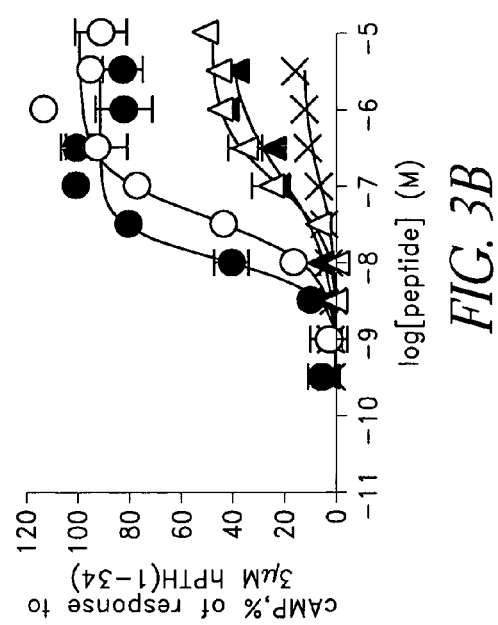

Pharmacology of N-Terminal Truncated Analogues of bPTH on Human and Rat PTH2 Receptors Analogues of bovine PTH lacking the first two N-terminal amino acids activated the human PTH2 receptor (FIG. 3C). In addition, [Nle$^{8,18}$, Tyr$^{34}$]bPTH(3-34) and bPTH(3-34) acted as partial agonists and displayed lower intrinsic activity than [Nle$^{8,18}$, Tyr$^{34}$]bPTH(1-34) (Table 3). However, no ligand-specific cAMP accumulation was observed for the truncated peptides at the rat receptor (FIG. 3D). Linear regression analysis of data from two experiments for each ligand indicated that the slope was not significantly different from zero (p>0.05). For comparison a similar analysis of data for the weak agonist PTHrP(1–34) (FIG. 3C) indicated a positive slope significantly different from zero (p<0.05) in three separate experiments.

Figure 4:
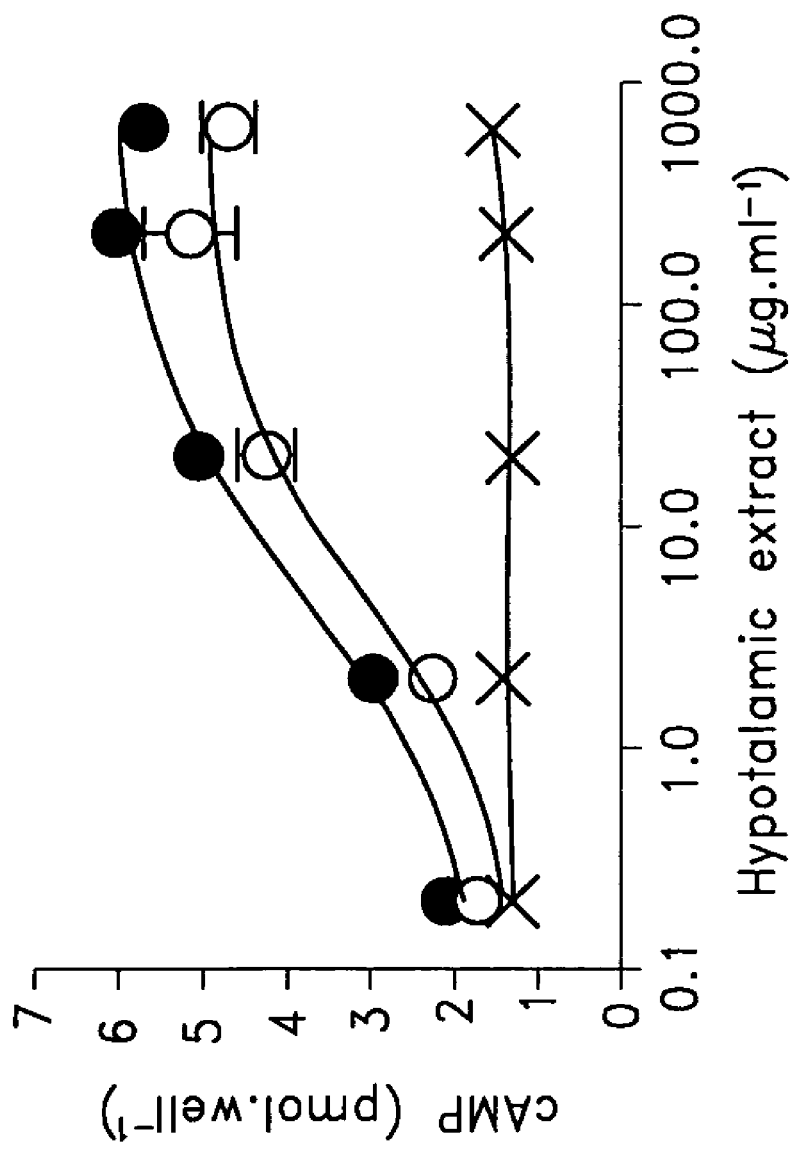
FIG. 4. Effect of bovine hypothalamic extract on human and rat PTH2 receptor-expressing cells. COS-7 cells were transfected with plasmids encoding β-galactosidase (×), the human PTH2 receptor (O) or the rat PTH2 receptor (●). Total cAMP was assayed as described in Examples using an assay volume of 25 μl per well of a 96-well plate. The data represent mean±range of duplicate measurements. In many cases the error bars are smaller than the symbols. The experiment was repeated once with similar results.

Stimulation of AMP Accumulation in Response to Bovine Hypothalamic Extract at Human and Rat PTH2 Receptors Initial experiments demonstrated that bovine hypothalamic acid extract activated the rat PTH2 receptor. Full dose-response curves (FIG. 4) show that the maximal and half-maximal responses to the extract are not significantly different at the human and rat PTH2 receptors (maximal responses=4.6±0.4 vs. 5.6±1.2 pmol cAMP well$^{-1}$, p=0.44; $EC_{50}$=4.0±0.6 vs. 5.0±1.2 ug ml$^{-1}$, p=0.44, for human and rat receptors respectively). At the human PTH2 receptor the maximal response to the extract was slightly less than the response to hPTH(1–34) (Table 3). However, at the rat PTH2 receptor the response to the extract was more than double that of the most efficacious ligand (rPTH(1–34), Table 4). Therefore all the PTH ligands tested were partial agonists at the rat PTH2 receptor.

Rank Order of Agonist Intrinsic Activity

Since a high concentration of a reference agonist was tested in parallel with all the ligands it was possible to determine the rank order of intrinsic activity. The reference ligands were hPTH(1–34) for the human PTH2 receptor (Table 3) and rPTH(1–34) for the rat PTH2 receptor (Table 4). For both the human and rat receptors analysis of variance indicated significant differences between the mean intrinsic activity values of the different ligands ($p=8.3\times10^{-11}$ for human receptor and p $4.4\times10^{-7}$ for the rat receptor). The ligand rank order of intrinsic activity was determined by pair-wise comparisons using, the Newman-Keuls test. The descending rank order for the hPTH2 receptor was hPTH(1–34)=rPTH(1–34)=rPTH(1–84)>hPTH(1–84)=[Nle$^{8,18}$, Tyr$^{34}$]bPTH(1–34)=extract>[Nle$^{8,18}$, Tyr$^{34}$]bPTH(3–34)=bPTH(3–34)>PTHrP(1–34). However a different rank order was observed for the rPTH2 receptor: extract>rPTH(1–34)=rPTH(1–84)>hPTH(1–34)=hPTH(1–84)=[Nle$^{8,18}$, Tyr$^{34}$]bPTH(1–34)=PTHrP(1–34)>[Nle$^{8,18}$, Tyr$^{34}$]bPTH(3–34)=bPTH(3–34). (The latter two ligands for the rat receptor were not included in the statistical analysis but were assumed to be of lower intrinsic activity than PTHrP(1–34) since stimulation of cAMP accumulation was not detected for these ligands.)

Measurement of Antagonist Inhibitory Potency

Figure 5A:
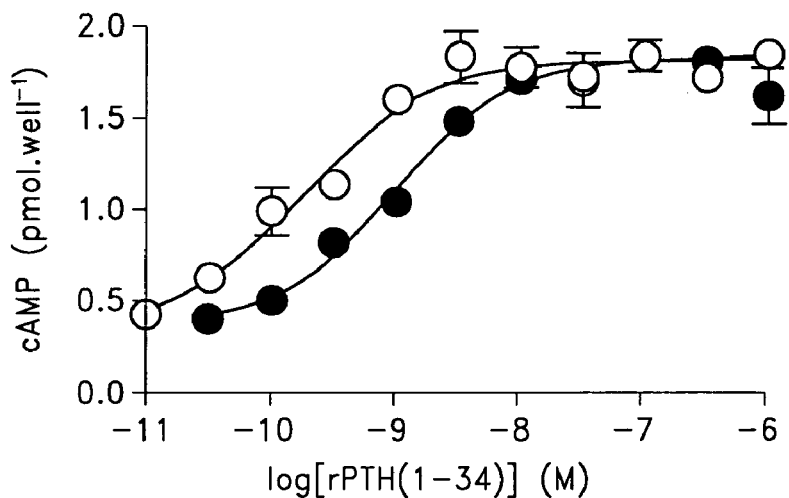
FIG. 5. Inhibitory potency of an antagonist ligand at human and rat PTH-2 receptors. COS-7 cells were transfected with plasmids encoding the human receptor (A) or rat receptor (B). The concentration-dependence of cAMP accumulation was measured as described in Examples, alone (O) and in the presence of 1 μM [Nle$^{8,18}$, D-Tryp$^{12}$, Tyr$^{34}$]bPTH (7–34) (●). The data represent mean±range of duplicate measurements. In many cases the error bars are smaller than the symbols. The data are from a representative experiment that was repeated twice with similar results. For human and rat receptors the antagonist did not affect basal cAMP accumulation in the absence of rPTH(1–34) (respectively 110±16% and 104±11% of basal response in the absence of antagonist) and did not affect the maximal stimulation in response to rPTH(1–34) (respectively 107±5% and 94±11% of maximal response in the absence of antagonist).
Figure 5B:
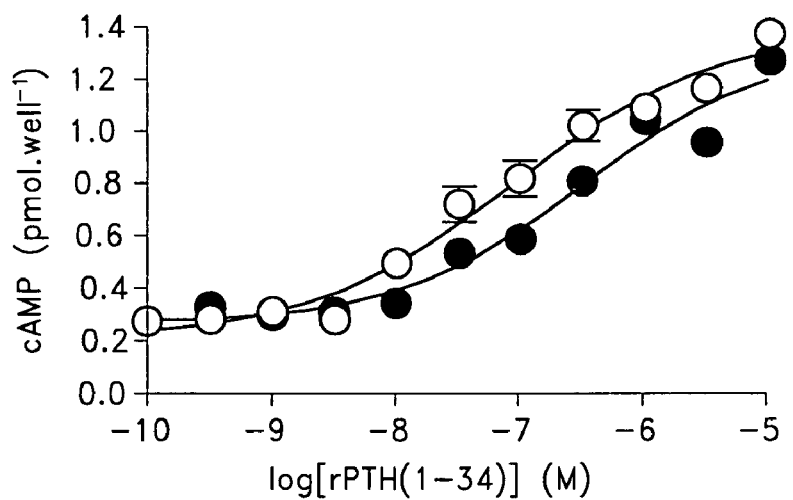

The different rank order of intrinsic activity values for agonist ligands suggests that the conformation of the receptors is different in a manner that affects the ability of ligand to activate the receptor. To investigate differences of activation-independent ligand binding affinity at the two receptors we compared the inhibitory potency of an antagonist ligand ([Nle$^{8,18}$, D-Tryp$^{12}$, Tyr$^{34}$]bPTH(7–34)). In these experiments the concentration-dependence of rPTH(11–34) for stimulation of adenylyl cyclase was measured in the presence and absence of 1 μM of the antagonist ligand. The rPTH(1–34) $EC_{50}$ value obtained in the presence and absence of the antagonist was used to calculate the antagonist $pA_2$, the concentration of antagonist required to produce a two-fold increase of $EC_{50}$. [Nle$^{8,18}$, D-Tryp$^{12}$, Tyr$^{34}$]bPTH(7–34) (1 μM) produced a rightward shift of the rPTH(1–34) concentration-response curve for both human and rat PTH2 receptors (FIG. 5). The $pA_2$ value for the antagonist was 6.5±0.1 (320 nM) at the human receptor and 6.5±0.2 (310 nM) at the rat receptor. These values are not significantly different (p=0.91). Activation-independent binding of this antagonist ligand is therefore similar at both human and rat PTH2 receptors.

Example 6

Purification of Bovine Hypothalamic Peptide TIP39

Figures 6A, 6B:
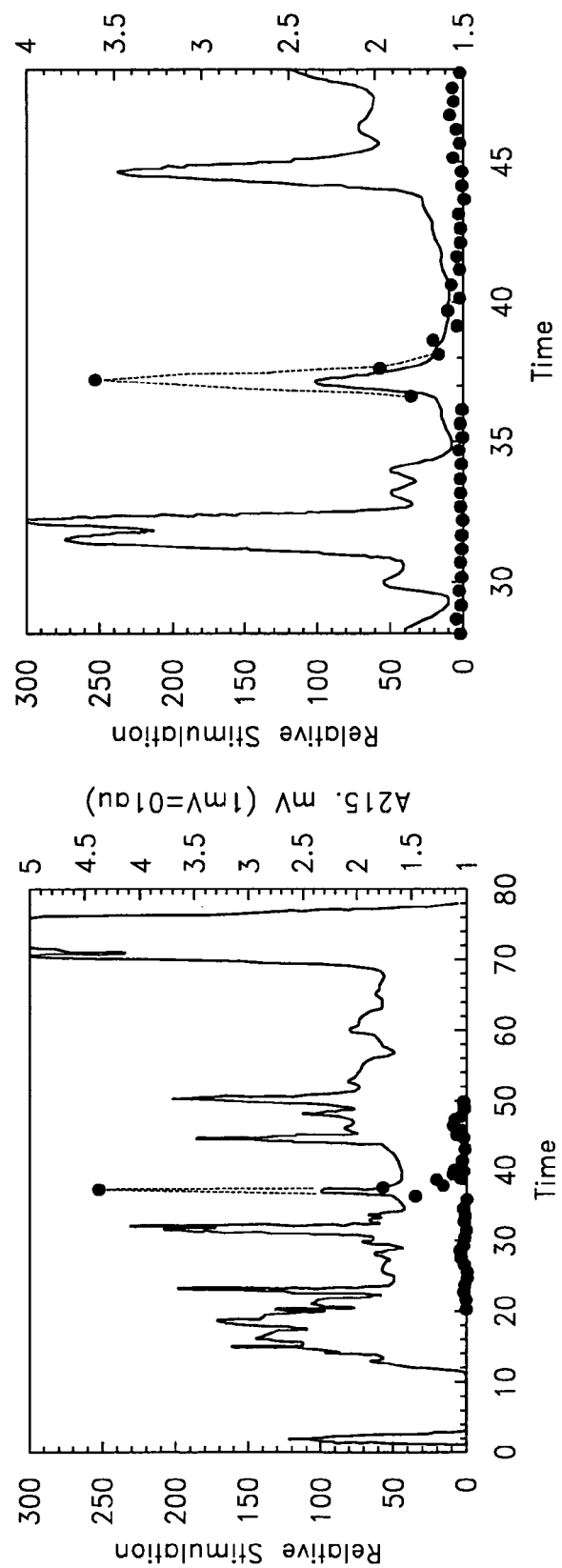
FIG. 6. Purification of the PTH2 receptor activating peptide. a) and b) HPLC purification of the bovine hypothalamic peptide. Peptides were extracted from bovine hypothalamus and purified. The final purification step on a Jupiter C18 column is shown. The UV absorbance trace (solid line) is plotted on the right vertical axis and relative stimulation of cAMP production (circles) is plotted on the left vertical axis. The entire run is shown in a) and a small region in b). c) Mass spectrometric analysis of the purified peptide. The MALDI-TOF spectrum from one region of a spot containing the purified peptide is shown.
Figure 6C:
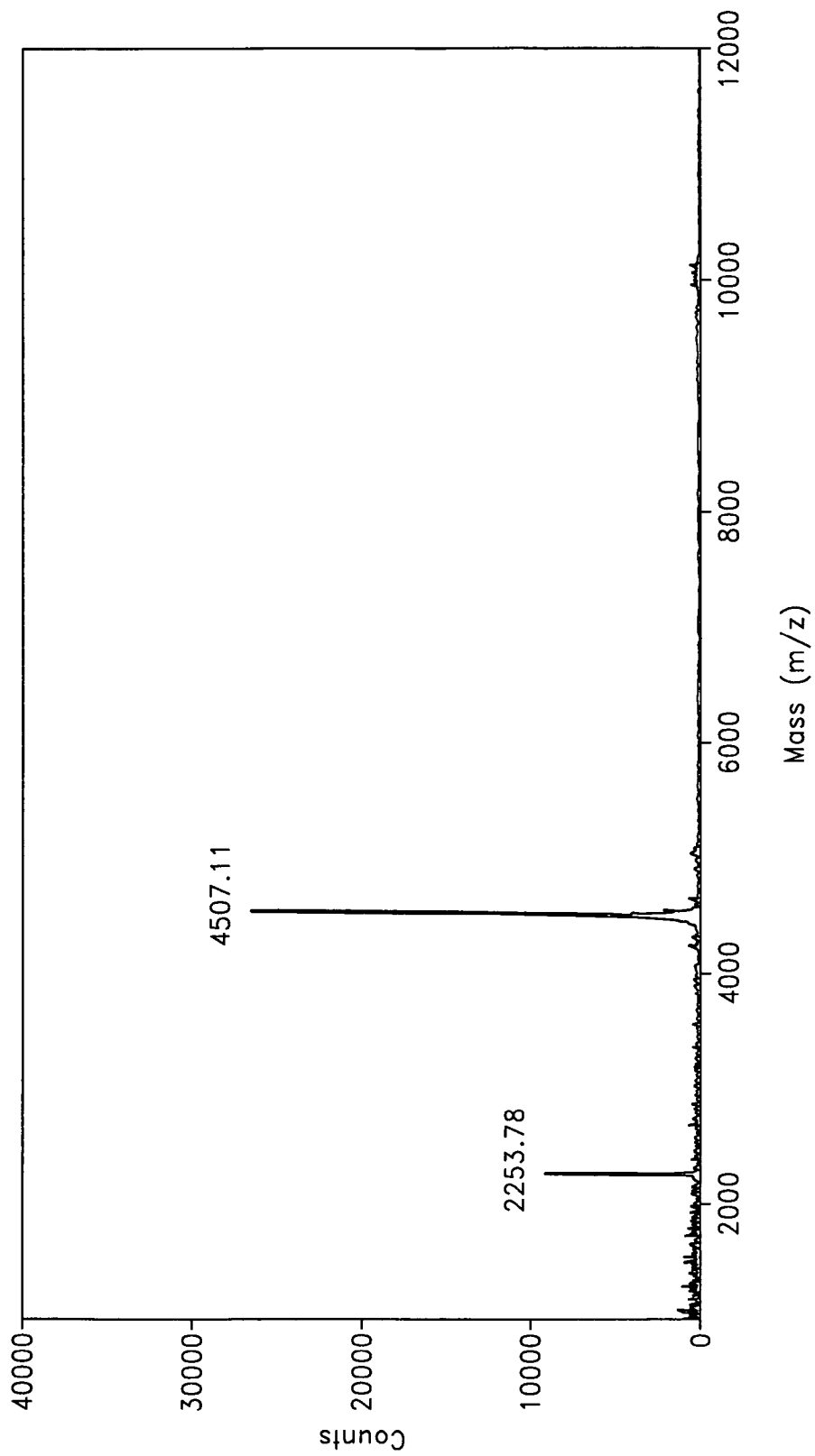
Figure 7A:
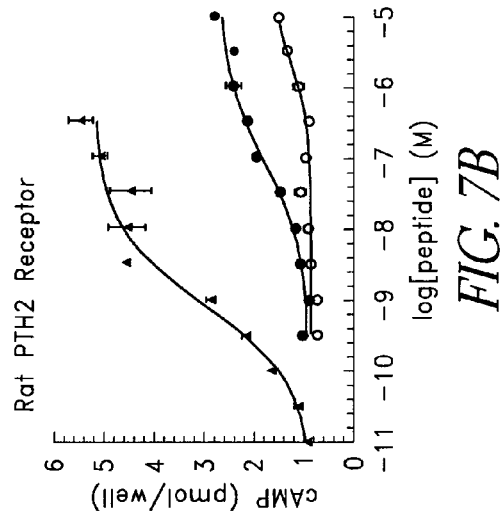
FIG. 7. Comparison of receptor activation by the synthetic hypothalamic peptide and PTH analogs. COS-7 cells transiently expressing the human PTH2 (a), rat PTH2 (b), human PTH1 (c) or rat PTH1 (d) receptor were stimulated with the synthetic hypothalamic peptide (triangles), rat PTH (1–34) (solid circles), or rat PTHrP (1–36) (open circles). Results from a typical experiment are shown.
Figure 7B:
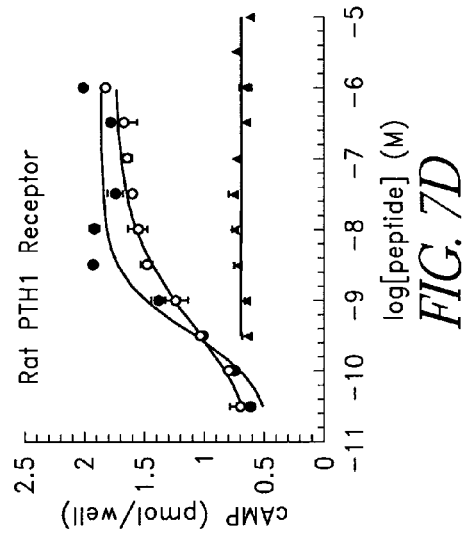
Figure 7C:
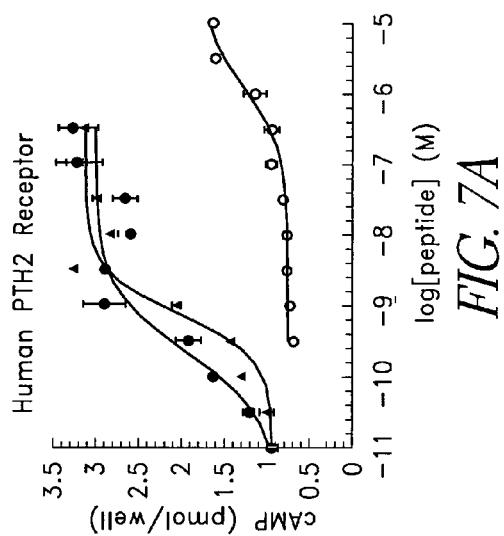
Figure 7D:
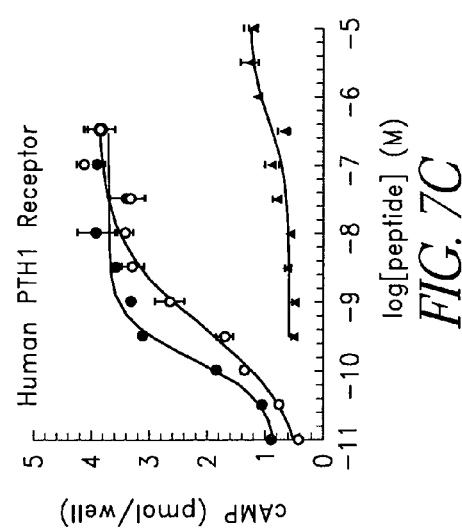

A biochemical purification scheme was developed for the ligand found in bovine hypothalamus extract, by using portions of an acid extract of fifty pounds of bovine hypothalamus to explore different chromatographic conditions. (FIG. 6) One bioactive fraction resulting from a series of six optimized chromatographic procedures was associated with a single symmetric peak of UV absorbance, and a single species of average molecular weight 4521.7, detected by mass spectrometry. A partial N-terminal amino acid sequence was determined by micro-scale Edman degradation. A second fifty pound batch of bovine hypothalamus was processed using the optimized purification scheme and a species of molecular weight 4505.45 was observed in the peak bioactive fractions. This suggested that the same polypeptide had been purified, with the mass difference accounted for by an oxidation during the first extraction and purification. The complete amino acid sequence of this 39 residue polypeptide, determined by microscale Edman degradation and mass spectrometry of tryptic fragments, is SEQ ID NO: 1. There was no evidence for post translational modification of any of the amino acids. The peptide had no obvious sequence homology to PTH or to PTHrP and a search of GenBank revealed no similar polypeptides.

The detailed purification and characterization protocol is described below. Bovine hypothalami were dissected and collected on dry ice at a commercial slaughterhouse. Bovine hypothalamus tissue (~23.75 kg) was received, frozen on dry-ice, with no evidence of melting. The frozen tissue, mixed with dry ice pellets, was ground using a Hobart hamburger grinder (22 hole-⅜ in. hole screen). The ground tissue was collected in stainless steel trays and stored at −25° C. until loaded into a freeze drier. Freeze drying was performed in a Virtis SRC-250 with a product shelf temperature gradient from −35° C. to 0° C. over four days. The freeze dried tissue (total weight 5.75 kg), was stored at −25° C. until further processed.

The freeze dried tissue was delipidated essentially in two large batches. Small batches of lyophilized tissue were transferred into a 4 L borosilicate glass beaker and homogenized into acetone using an Omni Inc. high shear rotor-stator probe, 35×195 mm. The motor armature of the homogenizer was bathed in $N_2$ to prevent ignition of acetone vapors. After homogenization the tissue slurry was poured into a 32 cm Buchner funnel lined with qualitative filter paper, and a gentle vacuum applied to speed the solvent removal. The contents of several 4 L beakers were added to the Buchner funnel, in total 3.05 kg for the first batch, and 2.7 kg for the second. The tissue was further extracted by pouring acetone through the filter pad, followed by a hexane extraction in the same way. The tissue was next washed with acetone in order to prevent the formation of a biphasic system between the hexane and the aqueous extraction medium in the subsequent step. The organic solvents were recovered by rotary evaporation for recycling within this project.

The desired peptide was extracted from the delipidated tissue into an aqueous acidic solution, (10 mM EDTA, 5.0% formic acid, 1.0% TFA, 1% NaCl, 1 μg/ml Bacitracin), at room temperature in a chemical fume hood. A borosilicate glass vessel larger than that used in the first processing was available, so the peptide extraction step could be performed in just two batches. The delipidated tissue from an original ~3.05 kg of freeze dried material was transferred directly from the Buchner funnel to a ~40 L borosilicate glass vessel containing ~30 L of the aqueous acidic solution. Extraction was by vigorous agitation with a pneumatic stirrer for ~15 minutes. The tissue slurry was quickly course filtered at room temperature by the use of three IEC centrifuges with basket rotors. The baskets were lined with Whatman 3MM paper and a fiberglass pre-filter. The most effective way to perform this filtration was by maintaining the rpm below 1,000 for the majority of the time, then finishing at 2,000 rpm to further dry the tissue. After basket centrifugation, the filtrate was stored at +4° C. until a final clarification step could be performed.

Another new piece of apparatus that became available after the first processing project was a continuous flow centrifuge, Zentrifugenbau type LE,#4032-20285, manufactured by a Swiss company, CEPA, Carl Pedberg. The centrifuge was fitted with a 3 mm inlet nipple (flow restrictor), and the filtrate was further clarified by allowing it to pass through slowly. The centrifuge chamber was cooled by passing +5° C. water through the jacket. The flow of filtrate into the centrifuge was started after the cylinder had reached at least 18,000 rpm. The operating rpm was 30,000. The maximum volume that was taken out of cold storage for centrifugation was 5 L at a time. The 30 L was filtered in 5 hrs., which is about twice as fast as using a bottle-type centrifuge. The final filtrate was stored over night at +4° C.

The clarified filtrate was transferred into the 40L borosilicate extraction vessel and 500g C18 phase-bonded silica (Matrix #84336) which had been prepared in 20% AcCN/ $H_2O$+5% AcOH was added. (The same C-18 which had been used to perform the first extraction process). The C18-containing slurry was stirred with the pneumatic stirrer for ~15 minutes.

The C18 was collected by vacuum filtration onto qualitative filter paper (Reeve-Angel, grade 22, 25 cm, cat# 5202-250) in a 25 cm Buchner funnel. The Buchner funnel containing the C18 was moved to a 5 L Schott borosilicate glass vacuum flask, and the C18 was washed with 20% AcCN/$H_2O$+5% AcOH, 1.5L. The 20% AcCN/$H_2O$+5% AcOH eluate was green in color, as was the case the previous time this work was performed.

The Buchner funnel was again moved, to another 5L Schott vacuum flask, and the C18 was washed with 1.5 L of 40% 1-propanol/$H_2O$+5% AcOH to elute the desired peptide from the C18. The C18 was then re-equilibrated in 20% AcCN/$H_2O$+5% AcOH and returned to the 40 L extraction vessel, as was same aqueous acidic solution, and a second absorption was performed. The C18-containing slurry was stirred for 15 minutes and then collected in a Buchner funnel. It was washed with 1.5 L of 20% AcCN/$H_2O$+5% AcOH and collected in the same flask from the first elution followed by 1.5 L of 40% 1-propanol/H2O+5% AcOH, which was also collected/combined with the 40% 1-propanol fraction from the first elution. The majority of the propanol was removed by rotary evaporation with a Büchi Rotavapor R-151, which can hold ~15 liters of solvent. The water bath was warmed at +40° C., and a very good vacuum, <300 mbar, was used. At the conclusion of the rotary evaporation the concentrated aqueous solution was transferred to borosilicate glass dishes and frozen to −50° C.

Processing in an identical manner was done on the remaining ~2.7 kg of freeze dried tissue as a single batch.

The entire concentrate from the 40% 1-propanol fraction, (both batches), was stored frozen at −50° C. until loaded into a Virtis 250 freeze drier.

The borosilicate glass dishes containing the concentrated 40% 1-propanol eluate, as well as portions of the twice-C 18-extracted aqueous acidic solutions and the 20% AcCN/ $H_2O$ fraction were loaded into a Virtis 250 freeze drier at −30 deg C. By having some of the material from each step in the processing for assay, the effectiveness of the peptide extraction and enrichment was determined. The volume of material required two (top) shelves in the freeze drier, i.e. 20% of a load, so one shelf was left empty as a spacer to minimize any opportunity for cross-contamination, and other lab materials were loaded and lyophilized at the same time.

Because of the organic component in the frozen extract, shelf temperature was raised slowly to 0° C. over 2 days, and freeze drying occurred over 5 additional days. At the end of this time the dry, off-white, light fluffy material was rapidly transferred into tarred 120 cc borosilicate bottles, and immediately capped to prevent absorption of moisture from the air.

Chromatographic purification: 1) Lyophilized material from the initial acid extract was dissolved in 50% acetic acid. This material was applied to a 3 liter Sephadex G-50 column equilibrated and eluted with 50% acetic acid. Fractions were collected and assayed for PTH2 receptor stimulating activity. 2) Activity containing fractions from the G-50 column were pooled. They were pumped in several batches onto a 22×250 millimeter Vydac (manuf. The Separations Group) C4 column which was equilibrated in 0.1% trifluoroacetic acid (TFA). While being pumped onto the column the material was diluted with an equal volume of 0.1% TFA being pumped through another pump. The column was then eluted with a gradient of 20% to 40% acetonitrile. Fractions were collected and small aliquots used for bioassay. 3) Activity containing fractions from step 2 were injected onto a Vydac Sulfo-propyl HPLC column which had been equilibrated in 50% acetic acid. Following return of the UV trace to baseline this column was eluted with a gradient of 0 to 25 mM NaCl in 50% acetic acid. Fractions were collected and small aliquots used for bioassay. 4) Activity containing fractions from step 3 were diluted with an equal volume of 8 M guanidine hydrochloride dissolved in 0.1% TFA and then injected onto a 4.6×250 mm Vydac C4 column which was equilibrated in 0.13% heptafluorobutyric acid. Following return of the UV trace to baseline this column was eluted with a gradient of 20 to 60% acetonitrile in 0.13% heptafluorobutyric acid. Fractions were collected and small aliquots used for bioassay. 5) Activity containing fractions from step 4 were diluted with an equal volume of 8 M guanidine hydrochloride dissolved in 0.1% TFA and then injected onto a 4.6×250 mm Jupiter C18 column (Phenomenex) which was equilibrated in 0.1% hydrochloric acid. Following return of the UV trace to baseline this column was eluted with a gradient of 20 to 60% acetonitrile in 0.1% hydrochloric acid. Fractions were collected and small aliquots used for bioassay. Based on the appearance of the UV absorbance profile an aliquot of the material was analyzed by MADLI mass spectrometry, and based on that analysis subjected to microscale Edman degradation.

Bioassay

Small aliquots of fractions were dried in polypropylene 96-well plates. PTH2 receptor expressing HEK293 cells were transferred to the wells and incubated at room temperature for 30 minutes. Following cell lysis relative cAMP levels were determined by competition with HRP-cAMP in a solid phase ELISA.

Sequence Determination

Edman degradation on the intact purified peptide was using a standard N-terminal protocol and an automated sequencer. This sequence was confirmed and the C-terminal residue assigned by online MS/MS spectroscopy of HPLC separated tryptic fragments using a Finnagin Instruments LC/Q system.

Synthetic Peptide Pharmacology

Dose-response curves were obtained by determining cAMP levels following incubation of HEK293 cells stably expressing the human PTH2 or PTH1 receptor, or COS-7 cells transiently expressing the human or rat PTH2 or PTH1 receptor, with synthetic hypothalamic peptide (Anaspec), PTH, or PTHrP as previously described in Clark, et al., *Mol Endocrinol* 12:193–206 (1998). (See FIG. 7).

The sequence was chemically synthesized and the resulting peptide had a molecular weight identical to the one purified, and the same fragment ions were produced following trypsin digestion. The synthetic peptide activated the human and rat PTH2 receptors with $EC_{50}$s of 0.5+/−0.12 nM and 0.8+/−0.3 nM (mean+/−S. E. M., n=3) respectively, which were well within the range expected for a polypeptide receptor ligand. The peptide was much more potent than PTH ($EC_{50}$=49+/−23 nM, n=3) at the rat PTH2 receptor and has a much greater maximal effect (approximately 3-fold). It had essentially no activity at the human or rat PTH1 receptors. The hypothalamic peptide and PTH ($EC_{50}$=0.15+/−0.24 nM, n=3) had similar potency at the human PTH2 receptor. The PTH1 receptor was also similarly activated by two distinct peptides, PTH and PTHrP, but 7 of their 11 most N-terminal residues were the same, while there was no obvious structural homology between PTH and the hypothalamic peptide. No example of a receptor potently activated by two ligands with as little similarity are known.

Example 7

PTH2 Receptors and PTH2 Receptor Ligands as Modulators of Nociception

The PTH2 receptor is expressed at relatively high levels by nerve terminals in the outer layers of the spinal cord dorsal horn. The nerve cells that project to this part of the spinal cord are primarily involved in perception of painful or unpleasant (nociceptive) stimuli. This suggests that the PTH2 receptor is involved in modulation of nociception. Identification and understanding of new modulators of nociception is important for understanding basic mechanisms underlying processing of sensory information, and is likely to contribute to the design of treatments for medical conditions, including chronic pain.

Evidence of PTH2 Receptor Involvement in Nociception

An examination of the modulation of PTH2 receptor expression by various stimuli was carried out to evaluate its involvement in functional circuits. Rats were sacrificed one hour following an injection of 4% formalin into one leg. In situ hybridization demonstrated c-Fos mRNA induction with an established "pain pattern". One set of sections was hybridized with a PTH2 receptor probe. On visual inspection of emulsion autoradiograms PTH2 receptor mRNA expression was decreased in several brain areas, including the hypothalamic PeriVN and some midline thalamic nuclei, in animals receiving the painful stimulus. In the PeriVN of treated animals (N=6 for control and treatment) the area occupied by silver grains was 48% of control (p=0.03), total optical density was 71% control (p=0.02), the number of cells with a grain level over background was 75% of control (p=0.028) and the area of labeling per cell was 66% control (p=0.04). These results indicate that this painful stimulus decreased the amount of PTH2 receptor expression in PeriVN neurons, and the number of neurons expressing it at detectable levels. Quantitation in other areas is underway.

PTH2 Receptor Ligands as Modulators of Nociception

Intracranial ventricular (ICV) cannulas are implanted into rats as described in the full protocol described below. Alternatively, rats are purchased with these cannulas implanted by a supplier (e.g. Taconic). Following several days for recovery from the surgery, an experiment is performed by placing an animal in a test cage, attaching tubing to the indwelling cannula and then administering test peptide (SEQ ID NO: 1) (10 micrograms or less) dissolved in sterile artificial CSF as described for pituitary hormone measurements. Standard assays of nociceptive sensitivity are performed following administration of vehicle or various doses of test peptide. These assays are discussed below.

Tail Flick Assay:

The tail flick assay uses an Omnitech Inc. (Columbus, Ohio) automated tail flick analgesia meter. This apparatus measures the latency for a rat's reflexive response to radiant heat focused on the tail. Rats are tested according to the methods described by Grant et al. (Anesth. Analg. 1994, 79:706) and the operation protocol provided by Omnitech, Inc. Briefly, the tail is placed in the photo-beam sensor/radiant heat source component of the apparatus. The heat source is activated and the reflexive flick of the tail interrupts the photo-beam. The latency of the tail-flick following stimulus is thus recorded. The intensity of the heat source is adjusted so that average latencies range from 4–6 seconds in control rats. The instrument setting to obtain this latency is determined in preliminary experiments using 3 animals. A 12 second shut-off is used to avoid thermal injury. 4 animals each at 6 peptide doses are used for the initial arm of this experiment to determine if the peptide (SEQ ID NO: 1) has an effect, and if so at what dose. In a second arm of the Example, the effect of the peptide to modulate the effect of other known effectors compounds (substance P, CGRP, enkephalin) is assessed. A second 24 animals is used in this arm for a total of 48 animals.

Hotplate Assay

This assay employs a Hotplate Analgesia Meter from Columbus Instruments and is based on the assay described by Eddy and Leimbach (J. Pharmacol. Exp. Ther. 1953, 107: 385–393). The Hotplate provides a constant 52 to 55° C. surface. This temperature is low enough to avoid harming the subjects, but is high enough to be uncomfortable for a rat. A small plastic cage around the Hotplate prevents the animals from scampering off the plate surface. The time delay between the placement of the animal onto the Hotplate to the moment that the experimenter observes temperature discomfort in the subject (i.e. licking of paws and feet, jumping) is recorded. As soon as the animals show the expected pain responses, they are removed from the hot surface and returned to their cage. If an animal does not respond within 240 seconds, it is removed and returned to its home cage in order to avoid the possibility of tissue damage. Animals are examined for tissue damage (blisters). The cut-off latency is shortened if any animals show signs of tissue damage. 4 animals each at 6 peptide doses are used for the initial arm of this experiment to determine if the new peptide has an effect, and if so at what dose.

In a second series of experiments the effect of the peptide to modulate the effect of other known effectors (substance P, CGRP, enkephalin) are assessed. A second 24 animals are used in this arm for a total of 48 animals.

Example 8

Assaying Chemical Libraries (Small Molecule Libraries) for PTH Receptor Ligand Activity Having various PTH2 ligands shown to bind to and elicit PTH2 receptor activity, the present invention contemplates the use of these ligands in assays to screen libraries of compounds for potential drug candidates. The generation of chemical libraries is well known in the art. A combinatorial chemical library can be used to generate compounds to be screened in the assays described herein. A combinatorial chemical library is a collection of diverse chemical compounds generated by either chemical synthesis or biological synthesis by combining a number of chemical "building blocks" reagents. For example, a linear combinatorial chemical library such as a polypeptide library is formed by combining amino acids in every possible combination to yield peptides of a given length. Millions of chemical compounds theoretically can be synthesized through such combinatorial mixings of chemical building blocks. One commentator observed that the systematic, combinatorial mixing of 100 interchangeable chemical building blocks results in the theoretical synthesis of 100 million tetrameric compounds or 10 billion pentameric compounds. Gallop et al., "Applications of Combinatorial Technologies to Drug Discovery, Background and Peptide Combinatorial Libraries," Journal of Medicinal Chemistry, Vol. 37, No. 9, 1233–1250 (1994).

Once generated, combinatorial libraries can be screened for compounds that possess desirable biological properties, such as PTH2 receptor binding and/or activation. For example, candidate compounds for use with the present invention would likely have the ability to bind to the PTH2 receptor. Assays to measure binding and cAMP generation in cells are two assays described herein that can be used to screen the compound libraries.

Another assay involves the binding of radiolabeled PTH2 receptor ligands to a population of cells expressing the PTH2 receptor to form a PTH2 receptor-ligand complex. A small molecule library is then added to the PTH2 receptor-ligand complexes in an attempt to displace the bound, labeled PTH2 peptide ligand. Those candidate compounds that successfully displace the radiolabeled ligands are selected and used in subsequent rounds of screening to develop non-peptide PTH2 receptor binding compounds.

Once a library of compounds is screened, subsequent libraries are generated using those chemical building blocks that possess the features shown in the first round of screen to have activity against the target enzyme. Using this method, subsequent iterations of candidate compounds will possess more and more of those structural and functional features desired, until a group of novel pharmaceutical compounds are identified. These compounds can then be further tested for their safety and efficacy for use in mammals.

It will be readily appreciated that this particular screening methodology is exemplary only. A wide variety of screening techniques are known for a large number of naturally-occurring targets and in any particular case, a person of ordinary skill in the art can readily create an appropriate assay when the function of the target protein is known.

Example 9

Nucleic Acid Sequences Encoding PTH2 Receptor Ligands

Nucleic acid sequences encoding the peptides, fragments, and analogs of the present invention are readily obtainable by calculation of these amino acid sequences into nucleic acid sequences using the genetic code to correlate amino acid identity with three-base-pair codons that may encode a given amino acid. The genetic code used for such determinations is routinely found in many textbooks and reference books, for example, Stryer, *Biochemistry* 636 (1975). Alternately, the actual coding sequence used by an organism of interest is determined by means the polymerase chain reaction (PCR), using degenerate primers designed to find any combination of codons used for a particular amino acids. Those primers that correspond to the actual codon usage in the DNA of interest anneal to the target DNA and permit PCR amplification of the region between the 5' and 3' primer targets. Amplified PCR products are sequenced and the sequence of the polynucleotide encoding the peptides, fragments, and analogs of the present invention is determined.

Determination of the TIP39 Sequence

A PCR based technique (inverse PCR) was used to determine part of the bovine genomic sequence for TIP39. This revealed a stop codon immediately following the proline at residue 39, a potential polyadenylation signal at residue 21, and nucleotides encoding two arginine residues immediately preceding the first residue identified by protein sequencing of the purified peptide. This demonstrated that TIP39 is the carboxyl terminal fragment of a precursor polypeptide, that may contain additional active peptides.

Search of GenBank with the sequence of bovine TIP39 (SEQ ID NO: 107) identified a homologous sequence in a working draft human genomic sequence, GenBank accession number AC068670 (SEQ ID NO: 108). The predicted amino acid sequence of the putative peptide encoded by this human DNA is identical to the sequence of bovine TIP39. The predicted nucleotide sequence differs by 3 bases in the coding region. There are also two arginine residues immediately upstream of residue number one of TIP39.

A fragment of bovine genomic DNA sequence was aligned with a fragment of human genomic sequence. See Appendix. The upper line of sequence is bovine and the lower line human. The nucleotide number 593 (arbitrary) corresponds to the first amino acid of protein-sequenced TIP39. The bovine genomic sequence was obtained by PCR using degenerate primers based on the amino acid sequence of TIP39. New primers were designed based on the actual nucleotide sequence determined between these primers and the sequence of flanking DNA determined by inverse PCR. The sequence of TIP39 was used in a tBLASTn search of the GenBank HTGS database to identify the fragment of draft quality human DNA.

Example 10

Molecular Determinants Of TIP39 Selective For PTH2 Receptors: N-terminal Truncation of TIP39 Reverses PTH2 Receptor/PTH2 Receptor Binding Selectivity Binding of TIP39 and rPTH(1–34) to PTH2 and PTH1 Receptors In HEK293 cells the stably-expressed human PTH2 receptor (293PTH2 receptor) is potently activated by TIP39

Figure 9B:
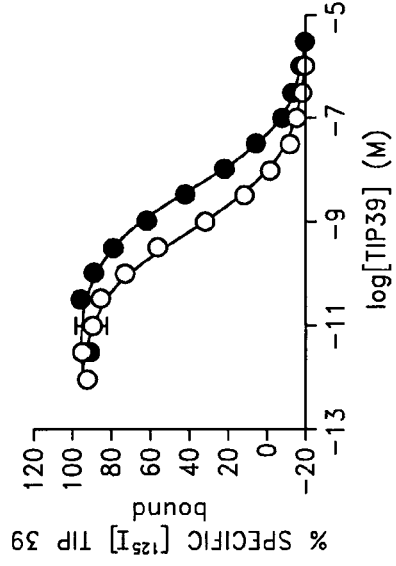
FIG. 9. Comparison of human PTH2 receptor activation and binding by TIP39 and rPTH(1–34). 293PTH2 and 293PTH1 receptors were used for these experiments. A Stimulation of cAMP production in intact cells by TIP39 (O), rPTH(1–34) (Δ) and PTHrP(1–34) (□). B Inhibition of [$^{125}$I]TIP39 binding to isolated cell membranes by TIP39. C Inhibition of [$^{125}$I]TIP39 binding to cell membranes by [Nle$^{8,21}$, Tyr$^{34}$]rPTH(1–34). Binding of the ligands was measured in the absence (O) and presence (●) of 10 μM GTPγS, using the centrifugation binding assay described in Examples. Specific [$^{125}$I]TIP39 binding was defined as the difference between total binding (no unlabeled ligand present) and non-specific binding (the lower plateau of the binding curve for B, and [$^{125}$I]TIP39 binding measured in the presence of 1.00 μM unlabeled TIP39 for C).
Figure 9C:
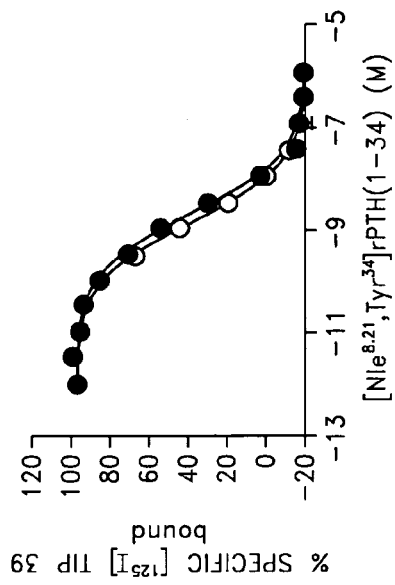
Figure 9A:
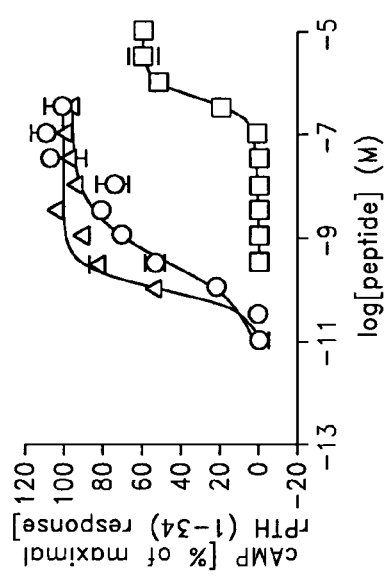
Figure 10B:
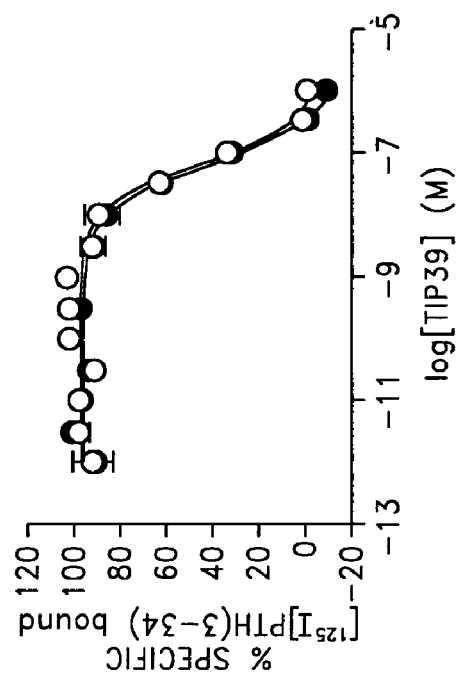
FIG. 10. Comparison of PTH1 receptor activation and binding by TIP39 and rPTH(1–34). 293PTH1 receptors were used for these experiments. A Stimulation of cAMP production in intact cells by TIP39 (O), rPTH(1–34) (Δ) and PTHrP(1–34) (□). B Inhibition of [$^{125}$I][Nle$^{8,21}$, Tyr$^{34}$]rPTH(1–34) binding to isolated cell membranes by TIP39 in the absence (O) and presence (●) of 10 μM GTPγS, using the centrifugation binding assay described in Examples. Specific [$^{125}$I][Nle$^{8,21}$, Tyr$^{34}$]rPTH(1–34) binding was defined as the difference between total binding (no unlabeled ligand present) and non-specific binding (measured in the presence of 300 nM unlabeled [Nle$^{8,21}$, Tyr$^{34}$]rPTH(1–34)).
Figure 10A:
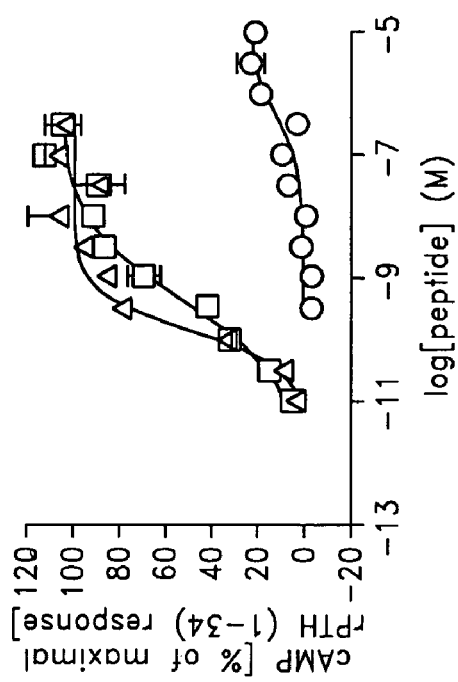
Figure 11A:
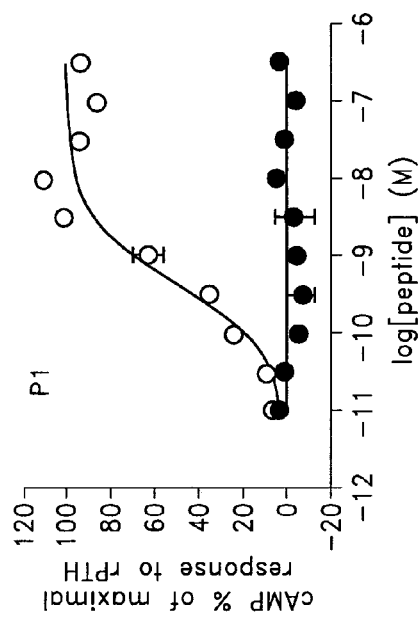
FIG. 11. Activation of chimeric PTH1/PTH2 receptors and wild-type PTH receptors by TIP39 and [Nle$^{8,21}$, Tyr$^{34}$]rPTH(1–34). Wild-type and chimeric receptors were expressed in COS-7 cells. Ligand-stimulated cAMP was measured as described in Examples (●—TIP39; O—[Nle$^{8,21}$, Tyr$^{34}$]rPTH(1–34)). A PTH2 receptor. B PTH1 receptor. C Chimeric receptor composed of N-terminal domain and first transmembrane domain of the PTH 1 receptor fused to the remainder of the PTH2 receptor (P2-NP1). D Chimeric receptor composed of the N-terminal domain and first transmembrane domain of the PTH2 receptor fused to the remainder of the PTH1 receptor (P1-NP2).
Figure 11B:
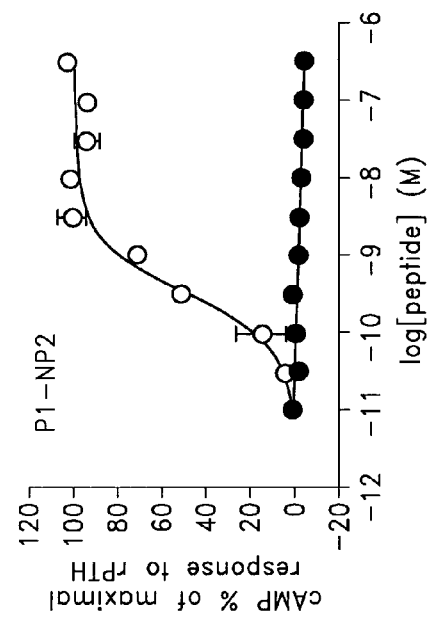
Figure 11C:
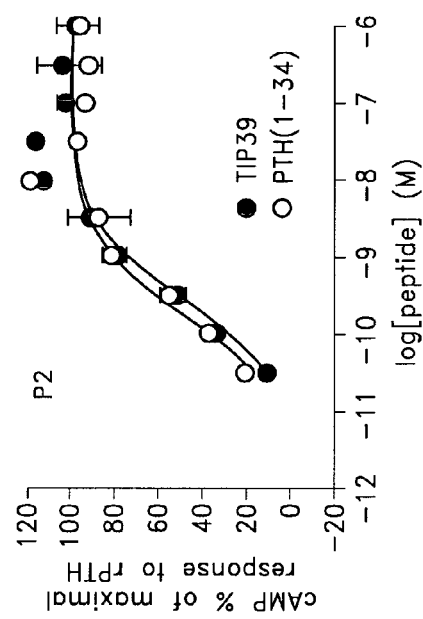
Figure 11D:
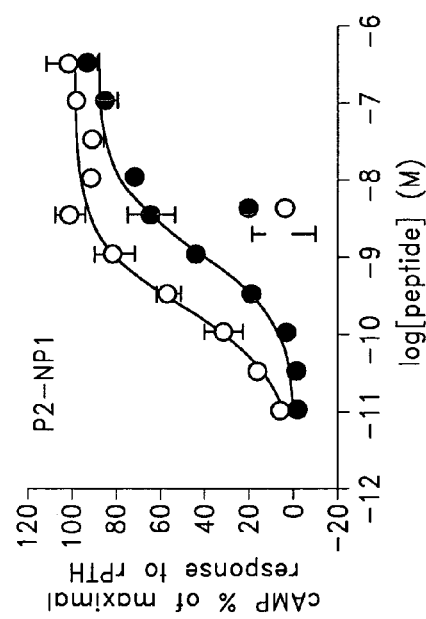

($EC_{50}$=0.44 nM) and by rPTH(1–34) ($EC_{50}$=58 pM, $E_{max}$=85% of the response to TIP39) whereas PTHrP(1–34) is much less potent (FIG. 9). The human PTH1 receptor stably expressed in HEK293 cells (293PTH1 receptor) is potently activated by rPTH(1–34) and PTHrP(1–34) ($EC_{50}$ values of 0.50 nM and 0.44 nM respectively) but is not appreciably activated by TIP39 (FIG. 10). TIP39 therefore selectively activates the PTH2 receptor in HEK293 cells. This activation profile closely resembles that of the receptors transiently expressed in COS-7 cells. It is possible that TIP39 binds to the PTH1 receptor but fails to activate it. It is also not clear how closely related are the concentration dependencies of TIP39 activation and binding. We therefore measured the binding of TIP39 to PTH1 and PTH2 receptors. The binding assays were performed in the absence and presence of 10 μM GTPγS to determine whether ligand binding was sensitive to receptor-G-protein (R-G) coupling.

[Nle$^{8,21}$, Tyr$^{34}$]rPTH(1–34) ([$^{125}$I]rPTH(1–34) has been used previously as a radioligand for the PTH2 receptor but we found that the signal-to-noise ratio was low in membrane binding assays (typically 3.5-fold and 2-fold in the absence and presence of GTPγS respectively). Since TIP39 is a potent agonist for the PTH2 receptor we evaluated it as a radioligand. TIP39 contains a tyrosine residue at position 29 that can be radio-iodinated as well as a methionine residue at position 30 that can potentially be oxidized during iodination. TIP39 labeled in a chloramine-T catalyzed reaction did not bind detectably to the PTH2 receptor. [$^{125}$I]TIP39 prepared in a lactose peroxidase catalyzed reaction bound to the PTH2 receptor in HEK293 membranes with a considerably higher signal-to-noise ratio than [$^{125}$I]rPTH(1–34) (20-fold and 15-fold in the absence and presence of GTPγS respectively) and no specific binding was detected in membranes prepared from non-transfected HEK293 cells. Unlabeled TIP39 displaced [$^{125}$I]TIP39 binding to the PTH2 receptor with high potency ($IC_{50}$=0.59 nM, FIG. 9B). The presence of 10 μM GTPγS produced a parallel 4.7-fold rightward shift of the binding curve, suggesting that TIP39 binds with higher affinity to the RG complex than to the uncoupled receptor (FIG. 9B). The pseudo Hill slope for TIP39 was significantly less than unity. No increase of the slope was observed by doubling or trebling the 2-hour incubation time. At the PTH1 receptor, TIP39 completely inhibited [$^{125}$I][Nle$^{8,18}$, Tyr$^{34}$]bPTH(3–34) binding with a moderate affinity of 59 nM, the binding curve described by a pseudo Hill slope of unity (FIG. 10B). Binding was insensitive to GTPγS indicating that the ligand binds with indistinguishable affinity to the RG and R states of the receptor (FIG. 10B). TIP39 therefore binds selectively to the PTH2 receptor over the PTH1 receptor. The peptide is a high affinity agonist of the PTH2 receptor and a moderate affinity antagonist of the PTH1 receptor. Binding selectivity was maintained in the presence of GTPγS indicating that this selectivity results from a stronger interaction with the PTH2 receptor and is not simply a result of receptor-G-protein coupling enhancing ligand affinity for this receptor.

The PTH2 receptor is activated with high potency by PTH as well as TIP39. We compared the binding of [Nle$^{8,21}$, Tyr$^{34}$]rPTH(1–34) (rPTH(1–34)) with that of TIP39. rPTH (1–34) displaced [$^{125}$I]TIP39 binding to the PTH2 receptor with high affinity ($IC_{50}$=1.1 nM, FIG. 9C). GTPγS produced a slight (1.5-fold) but statistically significant increase of $IC_{50}$ for rPTH(1–34) but did not alter the slope. The human PTH2 receptor therefore binds two distinct peptide ligands with high affinity. Since the receptor bound [$^{125}$I]rPTH (1–34) we next addressed whether the ligand binding parameters of unlabeled ligands were dependent upon the radioligand used. With [$^{125}$I]rPTH(1–34) as the radioligand, the binding parameters of TIP39 and unlabeled rPTH(1–34) were not significantly different from the values obtained using [$^{125}$I]TIP39 as the tracer. Both unlabeled ligands completely inhibited binding of both radioligands, consistent with identical or overlapping binding sites for TIP39 and rPTH(1–34).

Activation of Chimeric PTH2/PTH1 Receptors by TIP39 and rPTH(1–34)

Chimeric PTH2/PTH1 receptors were used to examine the molecular determinants of the receptor that specify the PTH2 receptor signaling selectivity of TIP39. These receptors were constructed by exchanging between the human PTH2 and PTH1 receptors a region comprising transmembrane domains 2 to 7 and the intervening loops (including the first intracellular loop) and the C-terminal tail, collectively referred to as the juxtamembrane domain. Chimeric and wild-type receptors were expressed in COS-7 cells and ligand-stimulated cAMP accumulation was measured.

The four receptors studied (chimeric and wild-type) produced an equivalent maximal accumulation of cAMP in response to rPTH(1–34) and were activated with an equivalent potency ($EC_{50}$) by this ligand (FIG. 11). As previously described, the PTH2 receptor was fully and potently activated by TIP39 whereas the ligand produced no detectable response at the PTH1 receptor (FIG. 11). A chimeric receptor made up of the juxtamembrane region of the PTH2 receptor and N-terminal extracellular domain of the PTH1 receptor (P2-NP1) was also fully activated by TIP39 (FIG. 11C)— the maximal cAMP accumulation was 98% of that for rPTH(1–34) at the same receptor. TIP39 activated this receptor with high potency ($EC_{50}$=2.0 nM), slightly lower than the potency of this ligand at the wild-type PTH2 receptor ($EC_{50}$=0.42 nM). The reciprocal chimera P1-NP2 containing the juxtamembrane domain of the PTH1 receptor was not detectably activated by TIP39 (FIG. 11D). These findings indicate that the juxtamembrane receptor region specifies the PTH2/PTH1 receptor signaling selectivity of TIP39.

Binding of TIP39 and rPTH(1–34) to Chimeric PTH2/PTH1 Receptors

Figure 12A:
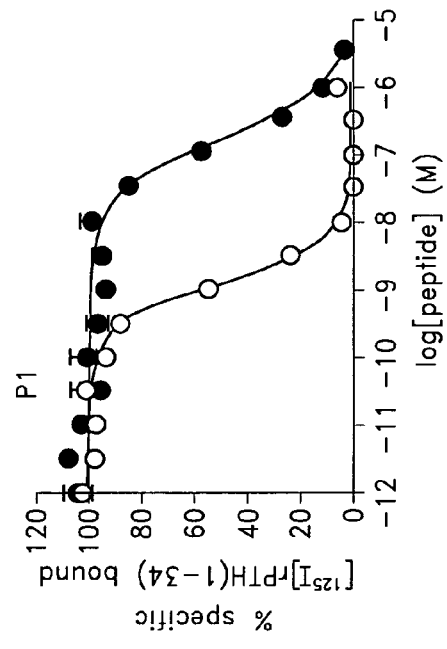
FIG. 12. Binding of TIP39 and [Nle$^{8,21}$, Tyr$^{34}$]rPTH (1–34) to chimeric PTH1/PTH2 receptors and wild-type PTH2 receptors. A) PTH2 receptor. B) PTH1 receptor. C P2-NP1 receptor D P1-NP2 receptor. Membranes were prepared from COS-7 cells transfected with receptor cDNA's. Binding of unlabeled TIP39 (●) and [Nle$^{8,21}$, Tyr$^{34}$]rPTH(1–34) (O) was measured by displacement of radioligand binding using the filtration binding assay described in Examples. [$^{125}$I] [Nle$^{8,21}$, Tyr$^{34}$]rPTH(1–34) was used to label PTH1 and P1-NP2 receptors and [$^{125}$I]TIP39 for PTH2 and P2-NP1 receptors. Specific binding was defined as the difference between total binding (no unlabeled ligand present) and non-specific binding (the lower plateau of the binding curve for homologous displacement assays, and binding measured in the presence of a 1.00 μM concentration of the unlabeled analogue of the radioligand for heterologous displacement assays).
Figure 12B:
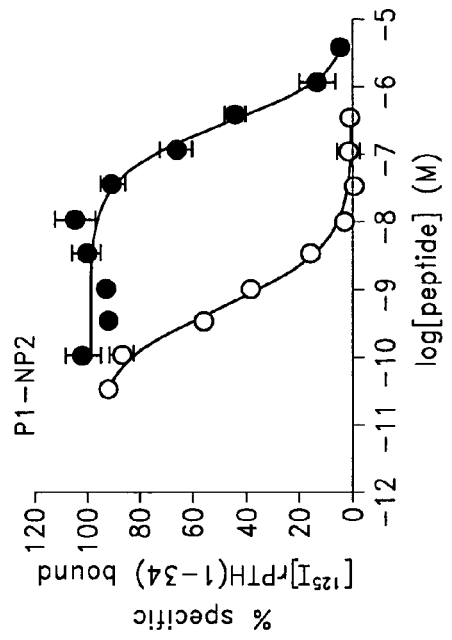
Figure 12C:
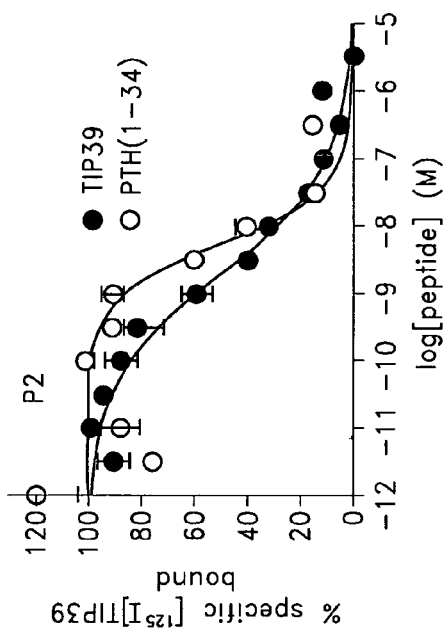
Figure 12D:
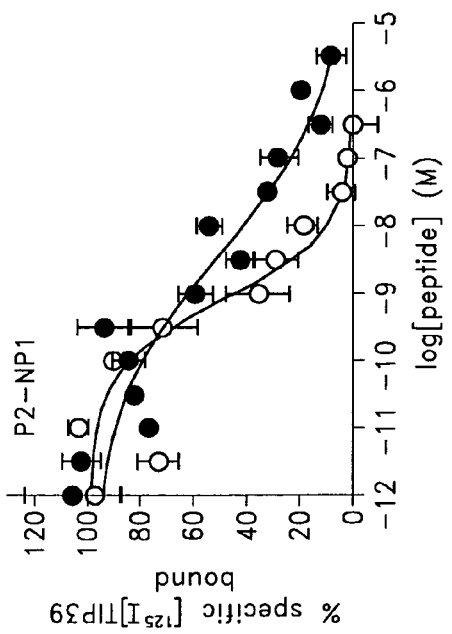

We examined the molecular determinants of the receptor specifying TIP39's binding selectivity for the PTH2 receptor using the chimeric PTH2/PTH1 receptors described above. rPTH(1–34) bound with high affinity to wild-type and chimeric PTH receptors in COS-7 membranes (FIG. 12) suggesting that the conformation of the chimeric receptors was not greatly disrupted compared with that of the wild-type receptors. The P2-NP 1 chimera, comprised of the juxtamembrane domain of the PTH2 receptor and N-terminal region of the PTH1 receptor, bound TIP39 with high potency ($IC_{50}$=2.3 nM) that was not significantly different from the TIP39 $IC_{50}$ at the wild-type PTH2 receptor (2.0 nM) (FIG. 12). The reciprocal chimeric receptor (P1-NP2, containing the juxtamembrane domain of the PTH1 receptor) bound TIP39 with low affinity ($IC_{50}$=280 nM), comparable with the ligand's affinity for the wild-type PTH1 receptor (160 nM) (FIG. 12D). Therefore the juxtamembrane domain of the PTH2 receptor specifies the PTH2 receptor binding selectivity of TIP39, as well as specifying the signaling selectivity (FIG. 11). For the PTH2 and P2-NP 1 receptors the pseudo-Hill slope value was less than one whereas the value for the PTH1 and P1-NP2 receptors was approximately unity. TIP39 completely inhibited binding of [$^{125}$I]rPTH(1–34) to the PTH1 and P1-NP2 receptors and rPTH(1–34) completely displaced [$^{125}$I]TIP39 binding to the PTH2 and P2-NP1 receptors.

The receptor states identified in these binding assays were evaluated using GTPγS to promote receptor/G-protein dissociation. GTPγS (10 μM) reduced radioligand binding by 53±4%, 5±2%, 69±6% and 63±1% at the PTH2, PTH1, P2-NP1 and P1-NP2 receptors, respectively. Thus, for the chimeric receptors and the PTH2 receptor the predominant state identified in these assays was the receptor-G-protein complex. The state of the PTH1 receptor identified in the assay cannot be defined unambiguously. However the R-G-coupling status of this receptor is not relevant to the evaluation of ligand binding selectivity given that TIP39 does not detectably discriminate the RG complex from the uncoupled receptor (FIG. 10B). These considerations suggest that the juxtamembrane domain specifies TIP39's PTH2/PTH1 receptor binding selectivity under conditions in which the receptor-G-protein complex is the receptor state predominantly detected in the binding assay. The signal-noise ratio did not permit critical evaluation of the binding selectivity of the chimeric receptors in the presence of GTPγS. However in whole cell binding assays, in which the receptor is probably predominantly uncoupled from G-protein, the juxtamembrane domain again specified the PTH2/PTH1 receptor binding selectivity of TIP39 ($IC_{50}$ values for the PTH2, PTH1, P2-NP1 and P1-NP2 receptors of respectively 3.3 nM, 415 nM, 5.4 nM and 1600 nM).

Effect of N-terminal Truncation of TIP39 on Stimulation of cAMP Production and Ligand Binding at PTH2 and PTH1 Receptors The above evaluation of chimeric PTH2/PTH1 receptors indicated that the juxtamembrane region of the receptor specified both the signaling selectivity and binding selectivity of TIP39 for the PTH2 receptor over the PTH1 receptor. In studies of the orientation of ligand binding to Type II G-protein-coupled receptors the N-terminal region of the ligand has been shown to interact with the juxtamembrane domain of the receptor, leading to receptor activation and second messenger generation. We therefore tested whether the N-terminal region of TIP39 was required for receptor activation by measuring the effects of removing residues from its N-terminus on ligand-stimulated adenylyl cyclase activity. We also measured the extent to which the N-terminal region of TIP39 specifies the selective binding of the ligand to the PTH2 receptor by measuring the binding affinity of N-terminally-truncated ligands for the PTH2 and PTH1 receptors.

Figure 13A:
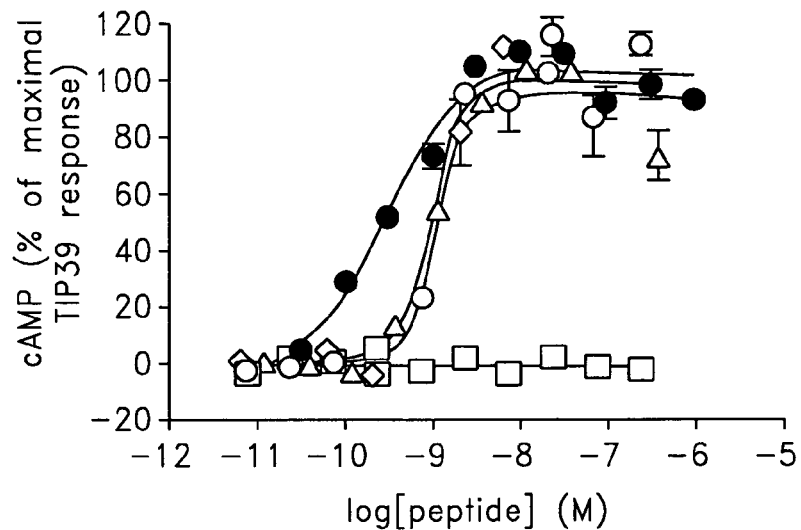
FIG. 13. Effect of N-terminal truncation of TIP39 on ligand-stimulated cAMP accumulation at PTH2 and PTH1 receptors. Adenylyl cyclase activity was measured in 293PTH2 cells (A) and 293PTH1 cells (B) as described in Examples for TIP39 (●), TIP(2–39) (O), TIP(3–39) (Δ), TIP(5–39) (◊), TIP(7–39) (□) and rPTH(1–34) (∇).
Figure 13B:
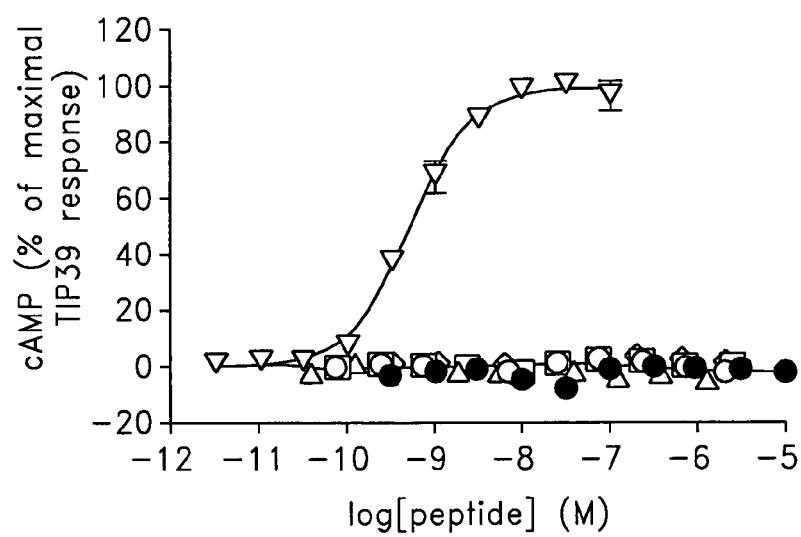

At the 293PTH2 receptor deletion of 1, 2 or 4 residues from the N-terminus of TIP39 reduced the potency for stimulation of cAMP accumulation but did not affect the maximal ligand-stimulated adenylyl cyclase activity (FIG. 13A). Deletion of 6 N-terminal residues, producing TIP (7–39), resulted in the loss of detectable ligand-stimulated cAMP accumulation (FIG. 13A). The N-terminal region of TIP39 is therefore a determinant of PTH2 receptor activation. None of the truncated TIP39 analogues detectably activated the PTH1 receptor (FIG. 13B).

Figure 14A:
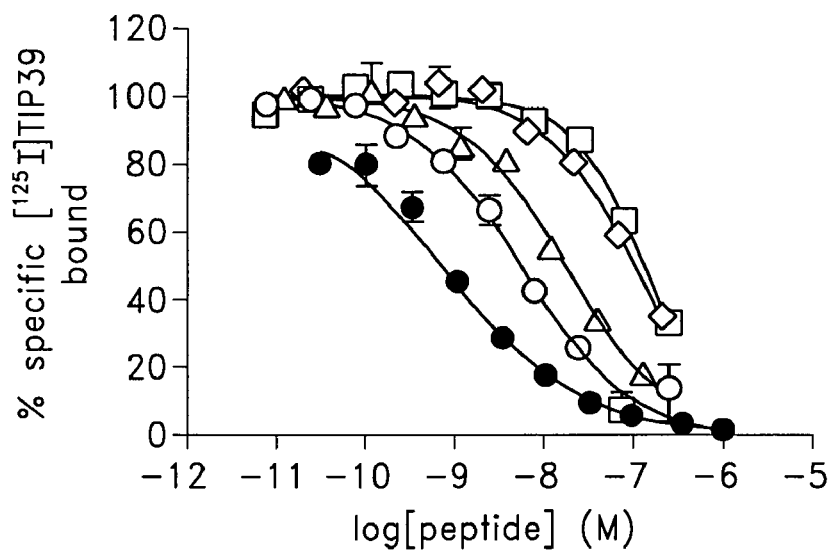
FIG. 14. Effect of N-terminal truncation of TIP39 on ligand binding to PTH2 and PTH1 receptors. Binding of unlabeled ligands was measured by displacement of radioligand binding to 293PTH2 membranes (A) and 293PTH1 membranes (B) using the filtration binding assay described in Examples. Under the conditions of the assay, the receptor-G-protein complex is the predominant receptor state detected. TIP39 (●), TIP(2–39) (O), TIP(3–39) (Δ), TIP (5–39) (◊), TIP(7–39) (□). [$^{125}$I]TIP39 was the radioligand for the PTH2 receptor and [$^{125}$I] [Nle$^{8,21}$, Tyr$^{34}$]rPTH(1–34) for the PTH1 receptor. Specific binding was defined as in FIG. 12. In the curve-fitting analysis for TIP(3–39), TIP (5–39) and TIP(7–39) at the PTH2 receptor non-specific binding was fixed at the binding measured in the presence of 1.00 μM TIP39.
Figure 14B:
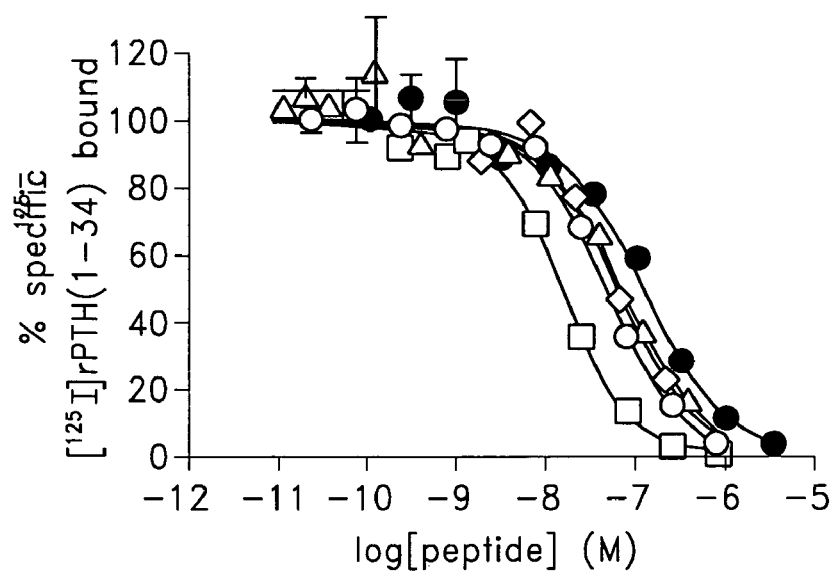

In radioligand binding assays deletion of 1, 2, 4 and 6 residues from TIP39 results in a progressive reduction of the ligand binding potency for the 293PTH2 receptor (FIG. 14A). TIP(7–39), which does not activate the PTH2 receptor, binds with 70-fold lower affinity to the PTH2 receptor than full-length TIP39 (FIG. 14A). (GTPγS (10 μM) reduced binding of [$^{125}$I]TIP39 to the PTH2 receptor by 62±2% indicating that the radioligand detects predominantly the receptor-G-protein complex of the PTH2 receptor in these assays.) In contrast, at the PTH1 receptor TIP(7–39) binds with a 5.6-fold higher affinity than TIP39 (FIG. 14B). The N-terminal region of TIP39 is therefore a determinant of TIP39's selective binding to the PTH2 receptor under conditions in which the G-protein-coupled receptor state is predominantly detected in the binding assay.

Figure 15A:
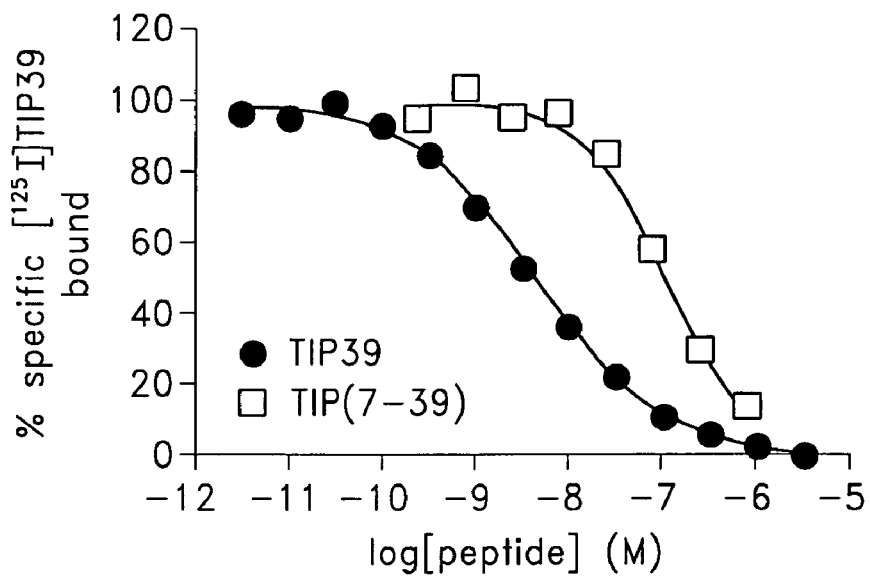
FIG. 15. Effect of N-terminal truncation of TIP39 on ligand binding to PTH2 and PTH1 receptors in the presence of 10 μM GTPγS. Binding of TIP39 (●) and TIP(7–39) (□) was measured by displacement of [$^{125}$I]TIP39 binding to 293PTH2 membranes (A) and [$^{125}$I] [Nle$^{8,21}$, Tyr$^{34}$]rPTH (1–34) binding to 293PTH1 membranes (B), using the centrifugation binding assay described in Examples. This assay measures the affinity of ligands for the free receptor, uncoupled from G-protein. Specific binding was defined as in FIG. 12. The mean $-\log IC_{50}$ values for the PTH2 and PTH1 receptors were ($IC_{50}$ values in parentheses): 7.01±0.04 (98 nM) and 8.30±0.05 (5.0 nM) respectively.
Figure 15B:
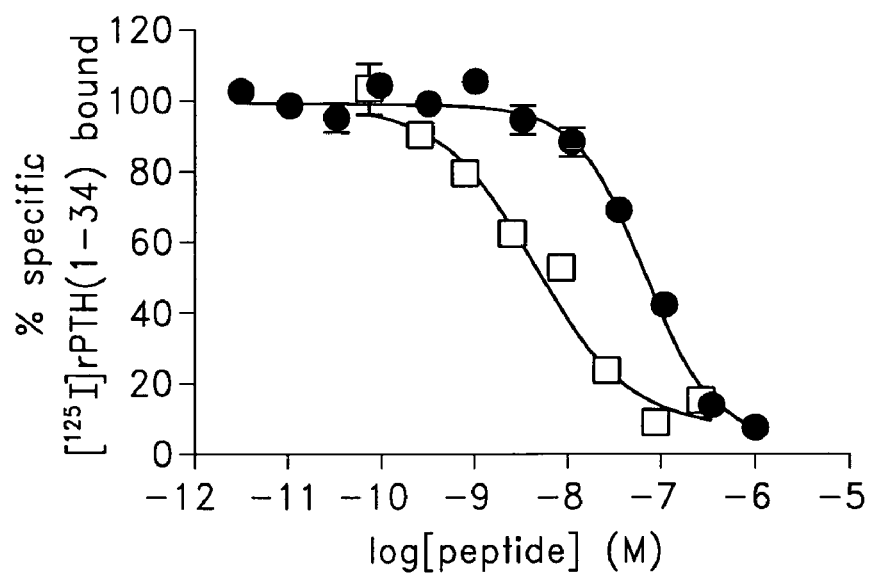

The effect of ligand truncation on receptor binding affinity was also measured at the G-protein-uncoupled receptor by measuring ligand binding in the presence of 10 μM GTPγS. Under these conditions TIP(7–39) bound to the PTH2 receptor with a 32-fold lower binding potency than full-length TIP39 (FIG. 15A). In contrast TIP(7–39) bound with 12-fold higher affinity to the PTH1 receptor (FIG. 15B). The N-terminal region of TIP39 is therefore a determinant of PTH2/PTH1 receptor binding selectivity at the G-protein-uncoupled receptor state.

In summary, removal of 6 residues from the N-terminus of TIP39 reduces receptor binding affinity at the PTH2 receptor but increases binding affinity at the PTH1 receptor. As a result, the truncation reverses the PTH2/PTH1 receptor binding selectivity of TIP39, such that TIP(7–39) is a selective, high affinity (<10 nM) antagonist of the PTH1 receptor and a weak antagonist of the PTH2 receptor.

Binding of TIP39 to Chimeric PTH2/Glucagon Receptors

The PTH2/PTH1 receptor selectivity studies above suggest that the juxtamembrane region of the PTH2 receptor contributes strongly to the binding affinity of TIP39. However the PTH1 receptor binds TIP39 with a moderate affinity and so does not provide a null background in which to measure the contribution of binding interactions to the overall affinity of the ligand. In particular the PTH2/PTH1 selectivity experiments have not addressed the role of the N-terminal extracellular domain in the binding of TIP39. It is possible that the N-terminal region contributes to the interaction of TIP39 with both PTH2 and PTH1 receptors, but this interaction may not be detected because the selectivity experiments only address the molecular determinants of the difference of ligand affinity between the two receptors.

Figure 16A:
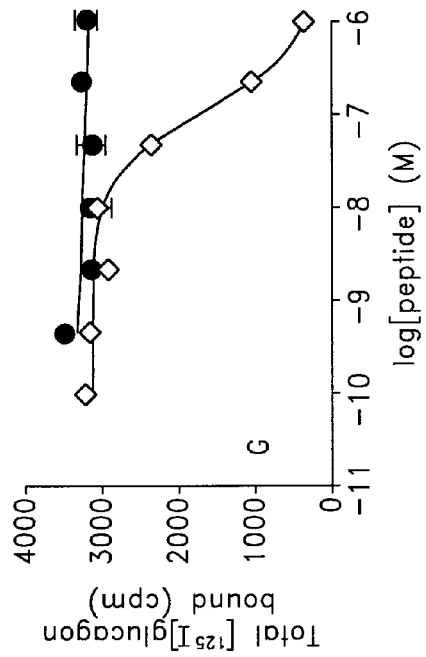
FIG. 16. Binding of TIP39 to a chimeric PTH2/glucagon receptor and PTH2 and glucagon receptors. An HA-tagged PTH2 receptor (P2, A), the human glucagon receptor (G, B) a chimeric receptor comprising the N-terminal extracellular domain of the PTH2 receptor and the juxtamembrane region of the glucagon receptor (G-NP2,C) and the reciprocal chimera (P2-NG, D) were expressed in COS-7 cells. Binding of TIP39 (●) or human glucagon(1–29) (◇) was measured by displacement of radioligand binding ([$^{125}$I]TIP39 for P2 and G-NP2 and [$^{125}$I]glucagon for G and P2-NG) using intact cells in 96-well plates. The total [$^{125}$I]TIP39 in A and C was 70,000 cpm, the total [$^{125}$I]glucagon in B was 14,000 cpm and the total [$^{125}$I]glucagon in D was 47,000 cpm. Data points are mean±s.e.m. of triplicate measurements. The experiments were performed three times with similar results, except for the glucagon receptor for which the experiment was performed twice.
Figure 16B:
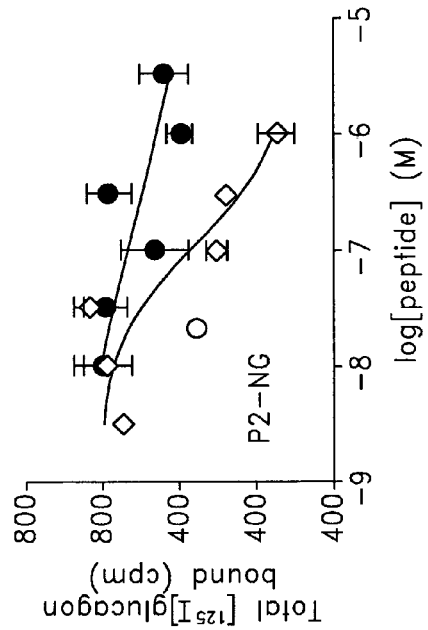
Figure 16C:
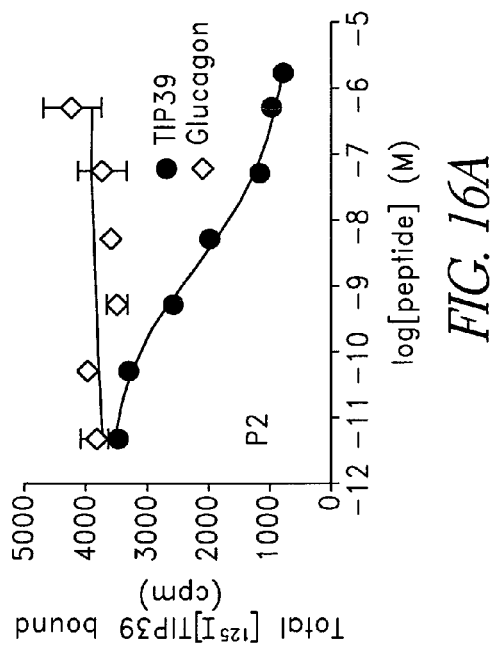
Figure 16D:
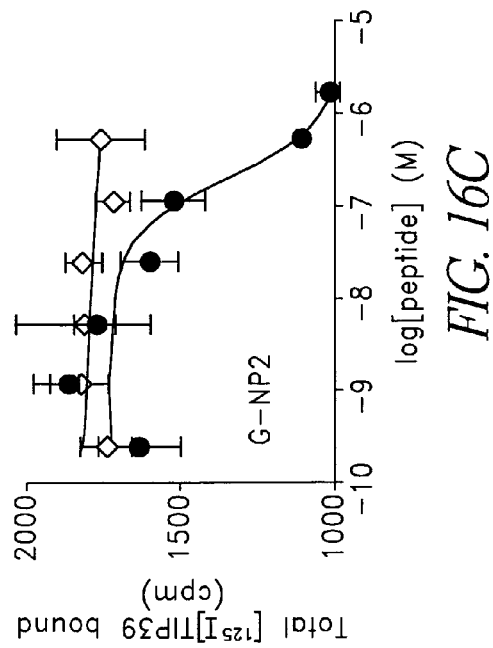

In order to more directly examine the molecular basis of TIP39 recognition by the PTH2 receptor we measured TIP39 binding to chimeric PTH2/glucagon receptors. The human glucagon receptor expressed in COS-7 cells did not detectably bind TIP39 at ligand concentrations up to 1 μM (FIG. 16B). This receptor was not detectably activated by TIP39 but glucagon(1–29) stimulated cAMP accumulation, with a –log $EC_{50}$ of 8.85±0.02 ($EC_{50}$=1.4 nM) and an $E_{max}$ of 4.3±0.2 pmol/mg (comparable with the $E_{max}$ for TIP39-activation of the PTH2 receptor). A chimeric receptor comprising the N-terminal domain of the PTH2 receptor and juxtamembrane region of the glucagon receptor (G-NP2) bound [$^{125}$I]TIP39 when expressed in COS-7 cells (FIG. 16C). Unlabeled TIP39 displaced this binding with a –log $IC_{50}$ of 6.74±0.42 ($IC_{50}$=182 nM, FIG. 16C). The TIP39 affinity of the G-NP2 receptor was 55-fold lower than that of the PTH2 receptor in COS-7 cells (FIG. 16A, –log $IC_{50}$=8.48±0.42, $IC_{50}$=3.3 nM). These data indicate that the N-terminal domain of the PTH2 receptor does contribute to TIP39 binding. The reciprocal chimeric receptor (P2-NG) detectably bound [$^{125}$I]glucagon but not [$^{125}$I]TIP39. Glucagon(1–29) displaced binding of [$^{125}$I]glucagon to the P2-NG receptor (–log $IC_{50}$=6.75±0.14, FIG. 16D) whereas TIP39 did not inhibit binding of the radioligand to this receptor (FIG. 16D). The P2-NG receptor was weakly activated by TIP39 ($EC_{50}$>1 μM) but not by glucagon(1–29) and the G-NP2 receptor was weakly activated by glucagon (1–29) ($EC_{50}$>1 μM) but not by TIP39.

Reagents and Peptides

The following peptides were purchased from Bachem (Torrance, Calif.), or Peninsula Laboratories (Belmont, Calif.): rPTH(1–34), [Nle$^{8,21}$, Tyr$^{34}$]rPTH(1–34) amide, [Nle$^{8,18}$, Tyr$^{34}$]bPTH(3–34) amide, PTHrP(1–34) and human glucagon(1–29). bTIP39 was obtained from AnaSpec Inc. (San Jose, Calif.) or Biomolecules Midwest (Waterloo, Ill.). The letters 'r' and 'b' designate the peptide sequence as rat and bovine, respectively. The peptides were dissolved in 10 mM acetic acid, with the concentration calculated using the peptide content and weight provided by the supplier. Aliquots were stored at −80° C. and used once. N-terminally-truncated TIP39 analogues were purchased from Biomolecules Midwest, purified by HPLC and quantified using the copper bicinchoninic acid method (Pierce, Rockford Ill.) with TIP39 as the standard. [$^{125}$I]cAMP was obtained from NEN (Boston, Mass.) and Na $^{125}$Iodine (2,000 Ci/mmol) was from ICN Biomedicals (Costa Mesa, Calif.). [3-$^{125}$I-iodotyrosyl$^{10}$]glucagon (2,000 Ci/mmol) was from Amersham (Arlington Heights, Ill.). Lactose peroxidase was obtained from Sigma. Cell culture supplies were obtained from Life Technologies (Frederick, Md.), except for Dulbecco's modified Eagle medium (DMEM) which was from Mediatech (Herndon, Va.).

Preparation of Radioligands

The radioligands [$^{125}$I][Nle$^{8,21}$, Tyr$^{34}$]rPTH(1–34) and [$^{125}$I][Nle$^{8,18}$, Tyr$^{34}$]bPTH(3–34) were prepared using chloramine T as catalyst and the di-iodinated peptide (4,000 Ci/mmol) purified by HPLC. [$^{125}$I]TIP39 was prepared using the lactose-peroxidase method. TIP39 (5 μg in 5 μl reaction buffer (0.1 M sodium acetate buffer pH 6.5)) was dispensed into a siliconized microfuge tube, followed by sequential addition of 0.5 mCi Na$^{125}$I, 5 μl of 20 μg/ml lactose peroxidase in reaction buffer, and 45 μl reaction buffer. After mixing, 10 μl of 0.001% H$_2$O$_2$ was added. After 20 minutes at room temperature the reaction was terminated by addition of 0.5 ml reaction buffer supplemented with 0.1% sodium azide. After a further five minutes, 0.5 ml reaction buffer supplemented with 1 M NaCl, 0.1% BSA and 1% potassium iodide was added. The radioligand was then de-salted using a C18 cartridge and purified by HPLC. The radioactive peak fractions corresponded with a single peak of UV absorbance.

Plasmid Constructions

The PTH2/PTH1 receptor chimeras have been described previously (Clark et al., Mol Endocrinol 12, 193–206, 1998). Chimeric receptors and their parent wild-type receptors contain a sequence encoding a 12 residue haemaglutinin (HA) tag inserted at the 3' end of the coding sequence. The chimeric receptors were constructed by exchanging residues 215–594 of the PTH1 receptor with residues 172–550 of the PTH2 receptor. Amino-acids 62–106 (encoded by exon E2 of the PTH1 receptor gene) were removed from the PTH1 receptor used for construction of these chimeras to facilitate comparisons with the PTH2 receptor which lacks a homologous sequence. TIP39 displayed an indistinguishable activation and ligand binding profile for the exon-deleted and full-length forms of the PTH1 receptor. A slightly different chimeric receptor nomenclature was used in this study compared with the study of Clark et al. P 1-NP2 is the same construct as P$_{rP}$-NP2 and P2-NP 1 corresponds to P$_2$-ΔNP$_{rP}$.

Chimeric PTH2/glucagon receptors were constructed by exchanging the N-terminal extracellular domain between the HA-tagged PTH2 receptor in pcDNA1/Amp and the human glucagon receptor in pCI$^{neo}$ MacNeil et al., Biochem Biophys Res Comm 198, 328–334, 1994. A BstZ17I restriction site was engineered into the human glucagon receptor sequence by converting C435 to thymidine, using the Gene-Editor Site-Directed Mutagenesis System (Promega, Madison, Wis.) according to the manufacturer's protocol, allowing the first 443 base-pairs of the coding sequence of the PTH2 receptor and the first 434 base-pairs of the glucagon receptor to be exchanged as BstZ17I/XbaI fragments.

Cell Culture and Transient Receptor Expression in COS-7 Cells

COS-7 cells were grown as previously described in Clark et al. For cAMP accumulation assays COS-7 cells were transfected as previously described in Clark et al. except that transfections were performed in 10 cm tissue culture dishes using 10 μg of plasmid DNA. The cells were transferred following trypsinization to 96-well plates at a density of 50,000 cells/well the following day. Cells were used for cAMP accumulation assays three days after transfection. For preparation of transfected COS-7 cell membranes, confluent 15 cm tissue culture plates were transfected with 30–100 μg DNA and cells harvested three days after transfection. HEK293 cells stably expressing the human PTH2 or PTH1 receptors were grown as previously (Usdin, Endocrinol 138, 831–838, 1997) and transferred to polyornithine-coated 96-well tissue culture plates one day prior to assay.

Measurement of Ligand-Stimulated cAMP Accumulation

Ligand-stimulated accumulation of cAMP was measured as described in Examples, using a radioimmunoassay to quantify cAMP (Clark et al., supra).

Isolation of Cell Membranes

P2 membrane preparations from HEK293 cells expressing the human PTH2 and PTH1 receptors were isolated as described in Examples. COS-7 cell membranes were prepared using a modified procedure. Cells were washed with 10 ml PBS per plate and mechanically dislodged in 10 ml 4 mM EDTA in PBS. Cells were centrifuged at 1,000×g for 10 min and the cell pellet suspended in lysis buffer (10 mM Tris, 2 mM EDTA, 6 mM MgCl$_2$ and 100 μM AEBSF, pH 7.5) using 32 ml lysis buffer for 5 confluent 15 cm plates of cells. After 1 hour at 4° C., 8 ml 1.25 M sucrose was added and cells were immediately homogenized by 50 strokes with a Dounce homogenizer. The homogenate was then centrifuged at 1,000×g for 10 min to remove unbroken cells and larger debris. Cell membranes were collected by centrifugation, quantified, and stored.

Radioligand Binding Assays

In these assays the binding of a range of concentrations of an unlabeled ligand was measured by displacement of radioligand binding. Three methods were employed. An assay employing centrifugation to separate bound and free radioligand was used to accurately measure ligand binding parameters. A higher-throughput method employing rapid filtration was used to generate comparative ligand binding data. Whole-cell binding assays were used to measure radioligand binding to chimeric PTH2/glucagon receptors since this assay provides the highest total binding/non-specific binding ratio, important for detecting lower affinity binding of radioligands. In these assays a very low concentration of radioligand was used so that the IC$_{50}$ closely approximates the ligand affinity.

In the centrifugation assay cell membranes (45–50 μg), radioligand (100,000–300,000 cpm) and unlabeled ligand were incubated in a final volume of 1 ml assay buffer (20 mM HEPES, 100 mM NaCl, 1 mM EDTA, 3 mM MgSO$_4$ pH 7.5, supplemented with 0.3% non-fat dried milk powder, 100 μM AEBSF and 1 μg/ml bacitracin) for two hours at 21°

C. Membranes were collected at 18,000×g, the surface of the pellet gently washed and the radioactivity counted as described in Examples. For the PTH1 receptor, [$^{125}$I][Nle$^{8,18}$, Tyr$^{34}$]bPTH(3–34) was used as radioligand at a final concentration of approximately 20–32 pM. The PTH2 receptor was labeled with [$^{125}$I]TIP39 (24–52 pM, assuming mono-iodination of TIP39 using the lactose peroxidase method) and [$^{125}$I][Nle$^{8,21}$, Tyr$^{34}$]rPTH(1–34) (14–28 pM). Less than 20% of the total radioligand added was bound within the membrane pellet. For [$^{125}$I]TIP39 binding to the PTH2 receptor in HEK293 membranes, this requirement necessitated the use of 15 μg membrane protein from transfected cells, made up to 45 μg with membranes from non-transfected HEK293 cells. (Greater than 50% of the total radioligand was bound if all the membrane in the incubation was from transfected cells).

In the filtration assay 5–10 μg membrane protein, 50,000–100,000 cpm radioligand (56–112 pM for [$^{125}$I]TIP39 and 28–56 pM for [$^{125}$I][Nle$^{8,21}$, Tyr$^{34}$]rPTH(1–34)) and unlabeled ligand were incubated for two hours at 21° C. Membranes were harvested as described in Examples. Total binding was less than 15% of the total amount of radioactivity added. The whole-cell binding assay was performed as previously described.

Data Analysis

Concentration-dependence data for ligand-stimulated cAMP accumulation and displacement of radioligand binding were analyzed using the following four parameter-logistic equation using Prism 2.01 (GraphPad Software Inc., San Diego, Calif.):

$$y = \min + (\max - \min)/(1 + 10^{(Log\ K - X)nH})$$

where X is the logarithm of the ligand concentration and $n_H$ is the pseudo Hill slope. For cAMP accumulation data y is the amount of cAMP produced at a given peptide concentration, min is the cAMP level in the absence of ligand and max is the maximum level produced. For inhibition of radioligand binding, y is the cpm bound at a given unlabeled ligand concentration, min is non-specific binding (measured in the presence of a high concentration of the unlabeled version of the radiolabeled ligand) and max is total binding (measured in the absence of unlabeled ligand). Statistical comparison of multiple means was performed initially by single-factor analysis of variance followed by post-hoc analysis with the Newman-Keuls test. Statistical comparison of two means was performed using a two-tailed Student's t-test.

Example 11

TIP 7–39 A Novel Selective Very High Affinity Antagonist for PTH1 Receptors with no Detectable Agonist Activity Binding of Antagonists to the Human PTH1 and PTH2 Receptor Radioligand binding assays were used to compare the receptor selectivity of TIP(7–39) with that of [D-Tryp$^{12}$, Tyr$^{34}$]PTH(7–34) and PTHrP(7–34). Membranes prepared from HEK293 cells expressing the human PTH1 receptor were labeled with [$^{125}$I][Nle$^{8,21}$, Tyr$^{34}$]rPTH(1–34) and from HEK293 cells expressing the human PTH2 receptor with [$^{125}$I]TIP39. Binding was measured in the presence of 10 μM GTPγS to minimize complications arising from receptor-G-protein coupling, such as pseudo-irreversible binding of the agonist radioligand.

Figure 17A:
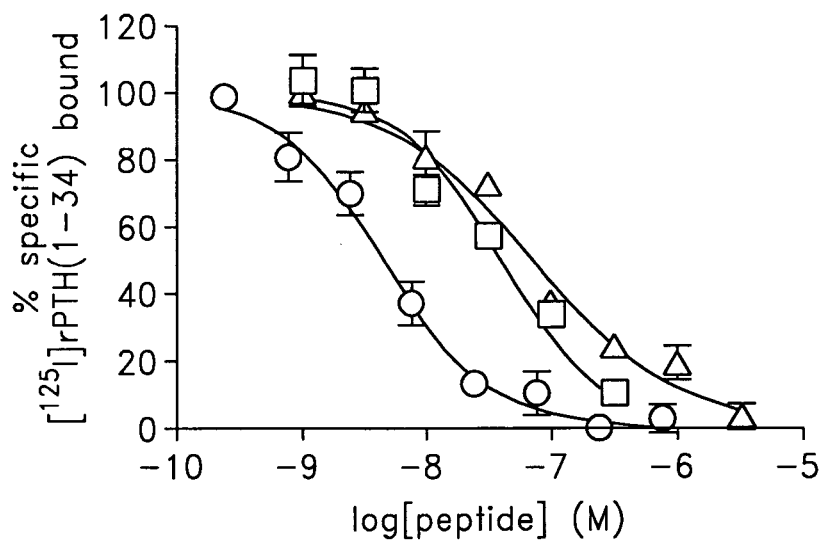
FIG. 17. Binding of antagonist ligands to human PTH1 and PTH2 receptors. Binding of the unlabeled ligands was measured by displacement of radioligand binding to HEK293 membranes as described in Examples. Binding was measured in the presence of 10 μM GTPγS (to measure antagonist affinity for the G-protein-uncoupled state of the receptors). A) Displacement of [$^{125}$I][Nle$^{8,21}$, Tyr$^{34}$]rPTH (1–34) binding to the PTH1 receptor. B) Displacement of [$^{125}$I]TIP39 binding to the PTH2 receptor. ○—TIP(7–39), □—[D-Tryp$^{12}$, Tyr$^{34}$]PTH(7–34), △—PTHrP(7–34). Non-specific binding was measured in the presence of 300 nM of the unlabeled analogue of the radioligand. For these representative experiments total binding of [$^{125}$I][Nle$^{8,21}$, Tyr$^{34}$]PTH(1–34) varied from 4400–4800 cpm, non-specific binding ranged from 1900–2400 cpm and the total radioligand added was 43,000 cpm. The ranges of total and non-specific binding for [$^{125}$I]TIP39 were 3,600–3,900 cpm and 570–1,000 cpm respectively and the total radioligand added was 46,000 cpm. Data points are the mean±s.e.m. of triplicate measurements. The data are from representative experiments that were performed 3 times except for measurement of [D-Tryp$^{12}$, Tyr$^{34}$]PTH(7–34) binding to the PTH2 receptor which was performed twice.
Figure 17B:
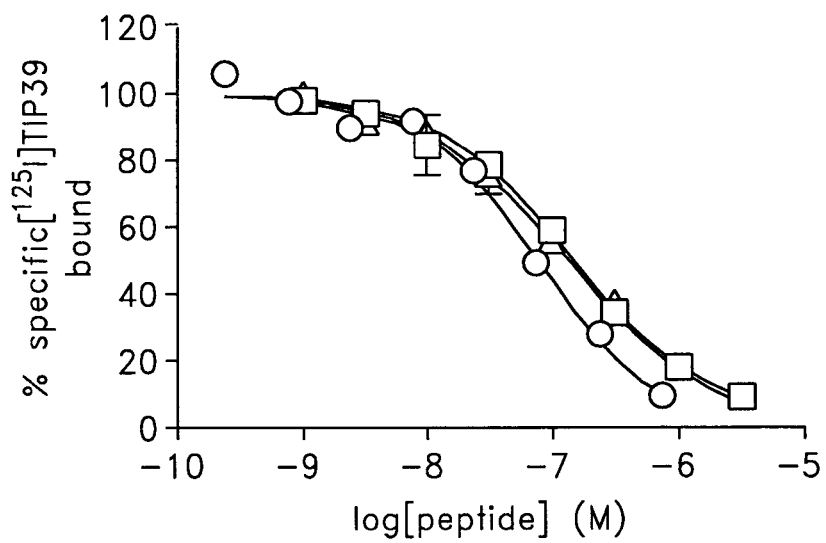

Binding of all ligands to both receptors was described by a pseudo Hill slope of approximately unity), consistent with a simple bimolecular reaction for the receptor-ligand interaction. TIP(7–39) bound with a significantly higher affinity to the PTH1 receptor than [D-Tryp$^{12}$, Tyr$^{34}$]PTH(7–34) or PTHrP(7–34) (FIG. 17). The difference of IC$_{50}$ was 7.3-fold for [D-Tryp$^{12}$, Tyr$^{34}$]PTH(7–34) and 10-fold for PTHrP(7–34). All of the antagonist ligands bound with lower affinity to the PTH2 receptor than the PTH1 receptor (FIG. 17). However, TIP(7–39) displayed a 5.5-fold greater selectivity for the PTH1 receptor than [D-Tryp$^{12}$, Tyr$^{34}$]PTH(7–34) or PTHrP(7–34).

Figure 18:
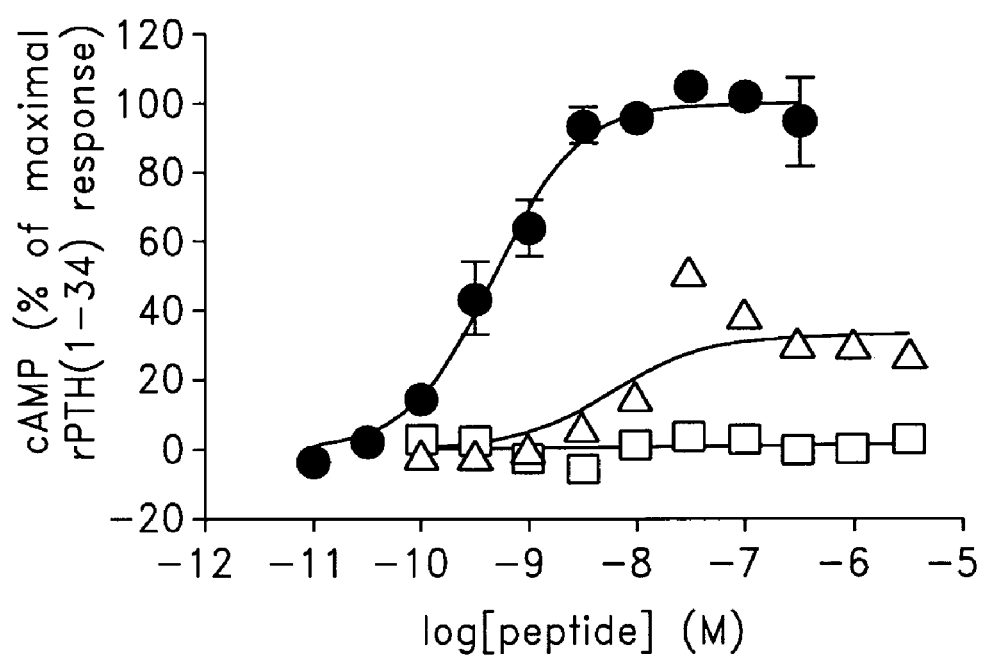
FIG. 18. Effect of TIP(7–39) on cAMP accumulation in COS-7 cells expressing a C-terminal-modified human PTH1 receptor. The PTH1 receptor was modified by addition of a 12 amino-acid residue hemaglutinin epitope to the C-terminus. cAMP accumulation was measured in response to rPTH(1–34) (●), [Nle$^{8,18}$, Tyr$^{34}$]PTH(3–34) (△) and TIP (7–39) (●) as described in Examples. The basal accumulation of cAMP was 0.95±0.04 pmol/well and the accumulation in the presence of a 320 nM rPTH(1–34) was 4.5±0.6 pmol/well (n=3). Data points are the mean±range of duplicate measurements. (Where error bars are not apparent they are smaller than the symbols). The experiment for [Nle$^{8,18}$, Tyr$^{34}$]PTH(3–34) was performed five times with similar results. The assay for TIP(7–39) was performed three times and in each experiment linear regression analysis indicated that the gradient was not significantly different from zero (p values of 0.54, 0.16 and 0.09).

Effect of TIP(7–39) on cAMP Accumulation in COS-7 Cells Expressing a C-Terminal Hemaglutinin-Tagged Human PTH1 Receptor Some PTH1 receptor ligands which were initially identified as antagonists based on inhibition of PTH-stimulated cAMP accumulation have since been demonstrated to possess significant efficacy in more sensitive assay systems. The best characterized example is [Nle$^{8,18}$, Tyr$^{34}$]bPTH(3–34). In contrast, TIP(7–39) did not detectably stimulate cAMP accumulation in HEK293 expressing the human PTH1 receptor but in these cells a response to [Nle$^{8,18}$, Tyr$^{34}$]bPTH(3–34) was also not detected. We attempted to develop a more sensitive measure of PTH1 receptor activation in order to evaluate the potential agonism of TIP(7–39), and used the ability to detect the partial agonism of [Nle$^{8,18}$, Tyr$^{34}$]bPTH(3–34) as the criteria for this assay. In COS-7 cells expressing the wild-type PTH1 receptor a measurable response to [Nle$^{8,18}$, Tyr$^{34}$]bPTH(3–34) was observed in two out of five assays. However, a hemaglutinin-tagged PTH1 receptor was detectably activated by this ligand in COS-7 cells in each of five experiments, with an E$_{max}$ of 26±4% of the maximal response to rPTH(1–34) (FIG. 18). This receptor contains a 12 amino-acid residue hemaglutinin epitope inserted at the C-terminus. TIP(7–39) did not detectably activate adenylyl cyclase activity in this assay (FIG. 18): Linear regression analysis indicated that the slope defining the concentration-dependence of cAMP accumulation was not significantly different from zero in three independent experiments. In addition, the level of cAMP accumulation produced by 3.2 μM TIP(7–39) (0.91±0.04 pmol/well) was not significantly different (p=0.51) from the accumulation measured in the absence of ligand (0.95±0.04 pmol/well).

Effect of TIP(7–39) on Intracellular Calcium Concentration

Figure 19:
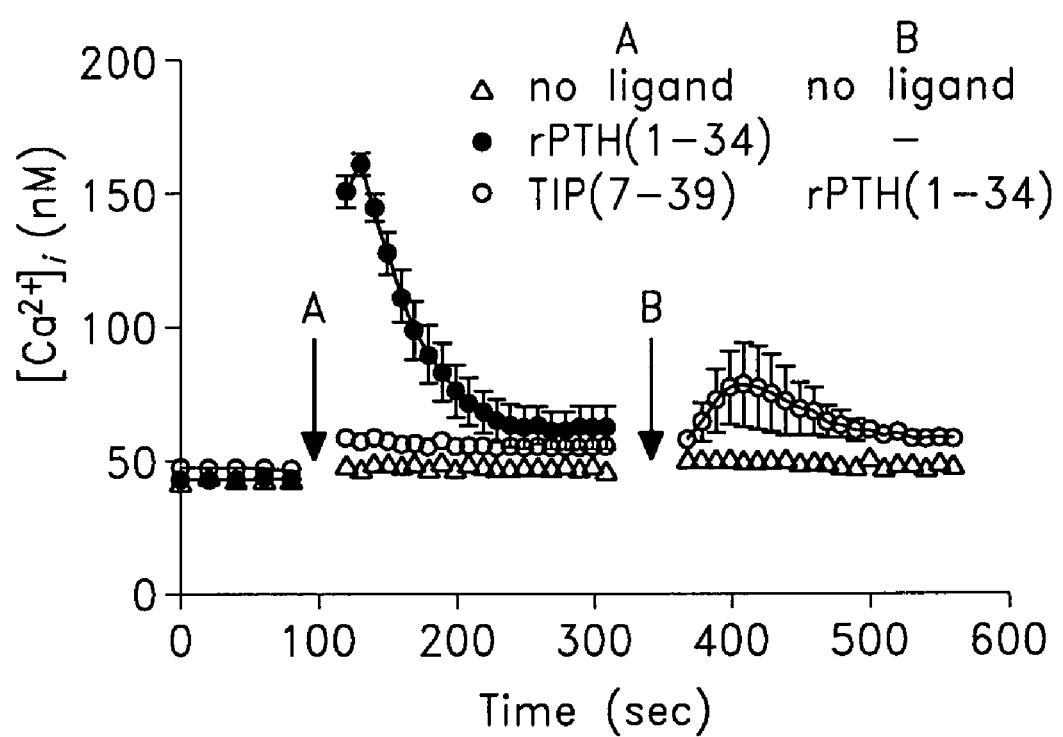
FIG. 19. Intracellular calcium concentration of HEK293 cells expressing the human PTH1 receptor in response to rPTH(1–34) and TIP(7–39). Cells were loaded with Fluo-4, the indicator excited at 485 nM and fluorescence measured at 530 nM as described in Examples. Data points represent the mean±range of measurements from two wells of cells. (Where error bars are not apparent they are smaller than the symbols). At time point A the following solutions were added to cells: △—10 μl buffer; ●—50 μl rPTH(1–34) (3 nM final concentration); ○—10 μl TIP(7–39) (1 μM final concentration). Subsequently at time B the following solutions were added: △—50 μl buffer; ○—50 μl rPTH(1–34) (3 nM final concentration). The experiment was performed twice with very similar results FIG. 20. Antagonism of PTH(1–34)-stimulated cAMP accumulation at the human PTH1 receptor by TIP(7–39). COS-7 cells were transfected with the PTH1 receptor and cAMP accumulation measured as described in Examples. Cells were pre-incubated with the antagonist for 30 min at 37° C. prior to addition of the agonist (rPTH(1–34)). A. The concentration-dependence of rPTH(1–34) for stimulation of adenylyl cyclase activity was measured in the absence of antagonist (●) and in presence of a range of concentrations of TIP(7–39) (○—240 nM, △—760 nM, □—2.4 μM). The $E_{max}$ for rPTH(1–34) was measured in parallel for assays of the TIP(7–39) effect, using 320 nM rPTH(1–34) in the absence of antagonist. This value was used to normalize the data presented in the figure. Basal cAMP accumulation in the absence of antagonist was 1.8±0.2 pmol/well and the $E_{max}$ for rPTH(1–34) was 6.2±0.7 pmol/well (n=6). TIP (7–39) did not affect accumulation of cAMP in the absence of agonist (values of 2.0±0.05, 2.2±0.05 and 2.5±0.7 pmol/well for 240 nM, 760 nM and 2.4 μM TIP(7–39) respectively). The antagonist did not affect the maximal rPTH (1–34)-stimulated level of cAMP accumulation (values of 101±10%, 104±14% and 114±18% of the maximal response to PTH(1–34) in the absence of antagonist for 240 nM, 760 nM and 2.4 μM TIP(7–39) respectively). Data points are the mean±range of duplicate measurements. Data are from a representative experiment that was performed three times. B. Schild plot of antagonism of PTH(1–34)-stimulated cAMP accumulation by TIP(7–39). Data points are the mean±s.e.m. of measurements from three independent experiments. Data from the different experiments were pooled for analysis by linear regression.

The PTH1 receptor has been demonstrated to couple to other second messenger pathways in addition to stimulation of cAMP accumulation. One of the best studied of these additional pathways is the elevation of intracellular calcium concentration ([Ca$^{2+}$]$_i$). We therefore tested whether TIP(7–39) effects [Ca$^{2+}$]$_i$, using Fluo-4-loaded HEK293 cells expressing the human PTH1 receptor. No change in [Ca$^{2+}$]$_i$ was observed when these cells were incubated with a high concentration of TIP(7–39) (1 μM), whereas 3 nM rPTH(1–34) produced a robust, rapid and transient increase in [Ca$_{2+}$]$_i$ (FIG. 19). TIP(7–39) (1 μM) antagonized the effect of rPTH(1–34) (3 nM)—the peak [Ca$^{2+}$]$_i$ increase was reduced by 79±1% and the rate of increase was reduced (FIG. 19).

Figure 20A:
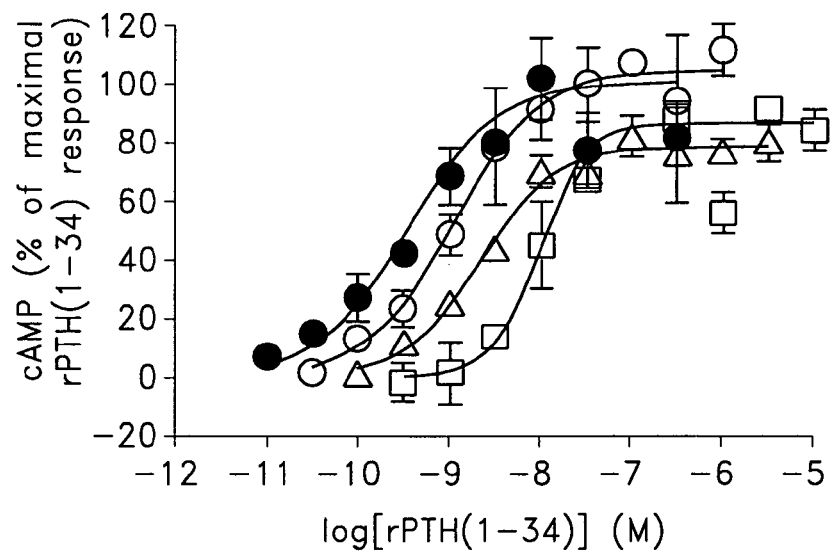
Figure 20B:
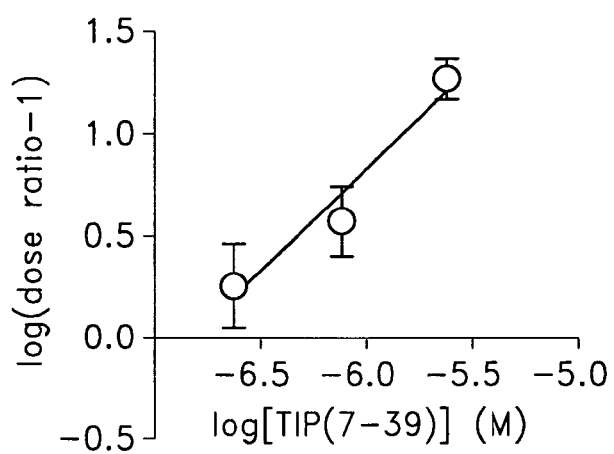

Measurement of Antagonist Potency of TIP(7–39) at Human and Rat PTH1 Receptors Expressed in COS-7 Cells Schild analysis of TIP(7–39) inhibition of rPTH(1–34)-stimulated cAMP accumulation was performed to examine the mechanism of action of the antagonist at the PTH1 receptor and to measure antagonist potency in a functional assay. TIP(7–39) produced a parallel rightward shift of the rPTH(1–34) concentration-dependence curve for stimulation of cAMP production at the human PTH1 receptor (FIG. 20). The antagonist did not significantly affect the $E_{max}$ for rPTH(1–34) and did not detectably activate cAMP accumulation in the absence of agonist (see legend to FIG. 20). The Schild slope was 0.99±0.24 (FIG. 20). These observations strongly suggest that TIP(7–39) acts as a competitive antagonist of rPTH(1–34)-stimulated cAMP accumulation at the human PTH1 receptor, at least over the range of antagonist concentrations tested. The $pK_B$ of TIP(7–39) at the human PTH1 receptor was 6.83 (150 nM). This value is 24-fold greater than the $IC_{50}$ of TIP(7–39) for inhibition of [$^{125}$I]rPTH(1–34) binding to the human PTH1 receptor. TIP(7–39) also antagonized PTHrP(1–34)-stimulated cAMP accumulation at the human PTH1 receptor, with a $pK_B$ of 6.94±0.09 (110 nM). The $pK_B$ of the antagonist was also measured for the rat PTH1 receptor expressed in COS-7 cells, using 3.2 μM TIP(7–39) and rPTH(1–34) as the agonist. The $pK_B$ value of 6.51±0.23 (310 nM) was not greatly different from that for the human PTH1 receptor.

Antagonist Potency in the Presence of Human Plasma

Figure 21:
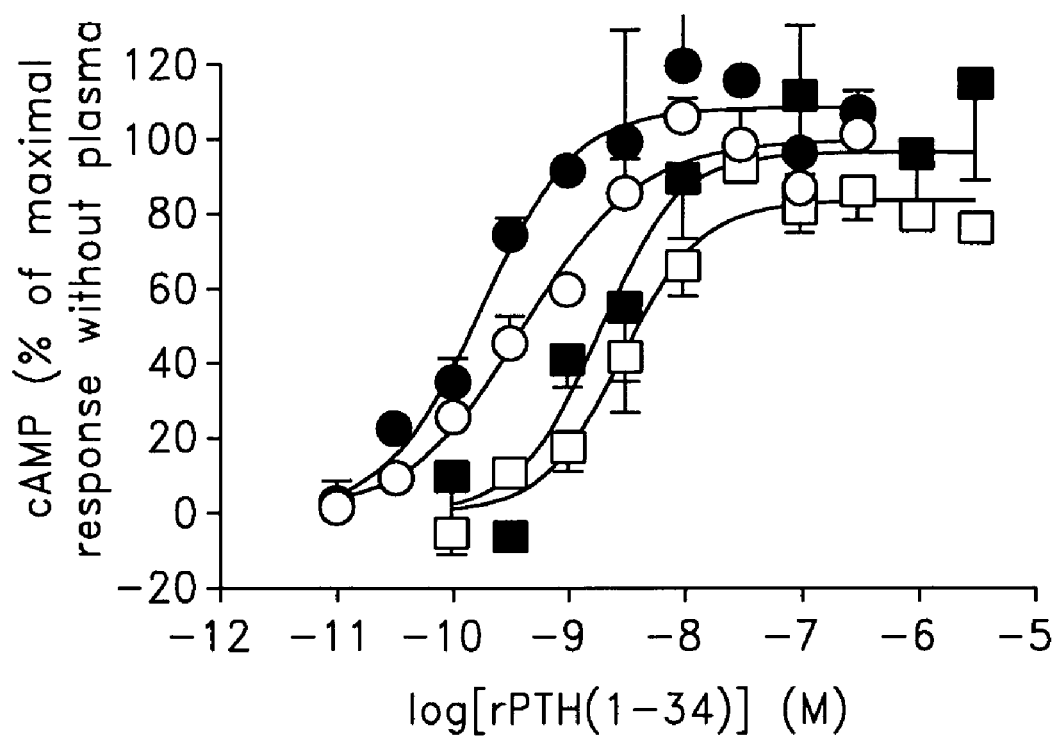
FIG. 21. Effect of human plasma on antagonism of PTH(1–34)-stimulated cAMP accumulation by TIP(7–39) at the human PTH1 receptor. The receptor was transiently expressed in COS-7 cells and cAMP accumulation measured as described in Examples. Plasma, antagonist and varying concentrations of agonist (rPTH(1–34)) were added to the cells in rapid succession and the cells incubated for 40 minutes at 37° C. The final concentrations of plasma and TIP(7–39) were 20% and 1 μM respectively. ○—PTH (1–34), ●—PTH(1–34)+plasma, □—PTH(1–34)+TIP39 (7–39), ■—PTH(1–34)+plasma+TIP(7–39). For assays measuring the effect of plasma and/or antagonist the maximal effect of PTH(1–34) without plasma or antagonist was measured in parallel using 320 nM PTH(1–34). This value was used to normalize the data presented in the figure. The fold-shift of $EC_{50}$ produced by TIP(7–39) was used to calculate the $pK_B$. In this experiment 1 μM TIP(7–39) produced a seven-fold shift of $EC_{50}$ in the absence of plasma and an eleven-fold shift in the presence of plasma. Data points are the mean±range of duplicate measurements. The experiment was performed twice with similar results.

One explanation that has been proposed for the lack of effect of PTH1 receptor antagonists in vivo is inactivation of the ligand as a result of ligand binding to plasma proteins. We investigated this possibility by measuring the antagonist effect at the human PTH1 receptor in the absence and presence of human plasma. The shift of rPTH(1–34) $EC_{50}$ produced by the antagonist was measured in the absence and presence of 20% human plasma. It is important to note that this experiment does not address the effects of serum proteases on the antagonist effect since the protease inhibitors bacitracin and AEBSF were included in the assay. Human plasma did not reduce the antagonist potency of TIP(7–39) (FIG. 21), [D-Tryp$^{12}$, Tyr$^{34}$]PTH(7–34) or PTHrP(7–34). Indeed, plasma increased antagonist potency between 2.3-fold and 3.5-fold. These experiments also demonstrate that TIP(7–39) displays a greater antagonist potency than either [D-Tryp$^{12}$, Tyr$^{34}$]PTH(7–34) or PTHrP(7–34), in both the absence and presence of plasma.

Binding of [$^{125}$I]TIP(7–39) to the Human PTH1 Receptor in HEK293 Cell Membranes We next examined whether binding of radiolabeled TIP (7–39) to the PTH1 receptor could be measured, which would enable a more detailed characterization of the ligand binding mechanism. bTIP39 contains a tyrosine residue at position 29 and a methionine residue at position 30, so [$^{125}$I]TIP39(7–39) was prepared using the mildly oxidizing lactose peroxidase method. Specific binding of this radioligand to the human PTH1 receptor was detected in membranes prepared from HEK293 cells expressing the receptor (using 300 nM TIP(7–39) or 300 nM TIP39 to define non-specific binding) whereas no specific binding was detected in HEK293 membranes prepared from non-transfected cells. The total binding:non-specific binding ratio for [$^{125}$I]TIP(7–39) was approximately 5:1, which is comparable with the signal-to-noise ratio of 6:1 obtained with [125I][Nle$^{8,18}$, Tyr$^{34}$]bPTH(3–34) (a commonly used radiolabeled antagonist/partial agonist for the PTH1 receptor). The affinity of [$^{125}$I]TIP(7–39) for the PTH1 receptor was measured in saturation experiments, using varying concentrations of the radioligand. The saturation data were fitted well by a single-site saturation isotherm (FIG. 22), a two-site model not providing a significant improvement to the fit (p values ranged from 0.75–0.95). The $K_D$ for [$^{125}$I]TIP39 (7–39) was 1.3±0.1 nM and the $B_{max}$ 1.3±0.1 pmol/mg (n=3). This $K_D$ is comparable with that for [Nle$^{8,18}$, Tyr$^{34}$] bPTH(3–34) (2.0 nM). The $B_{max}$ is slightly higher than that for [Nle$^{8,8}$, Tyr$^{34}$]bPTH(3–34) (0.7 pmol/mg). However this value was obtained from homologous displacement experiments, which may be less accurate than saturation experiments for measurement of $B_{max}$ if there is a difference between the binding affinities of the iodinated and non-iodinated ligands.

Measurement of Antagonist Binding Kinetics at the Human PTH1 Receptor in HEK293 Cell Membranes The association and dissociation rate constants for [$^{125}$I] TIP(7–39) binding to the PTH1 receptor were measured directly using data from the time courses of radioligand association and dissociation. The affinities of [D-Tryp$^{12}$, Tyr$^{34}$]PTH(7–34) and PTHrP(7–34) are probably too low to permit their use as radioligands in binding assays. Rate constants for these peptides were measured indirectly using a method in which association of a single concentration of a radioligand ([$^{125}$I]TIP(7–39)) is measured in the presence of a single concentration of the unlabeled test ligand. The time course data (FIG. 23) were fitted to Equation 4 as described in Examples below to obtain estimates of the association and dissociation rate constants of the unlabeled ligand.

Figure 22A:
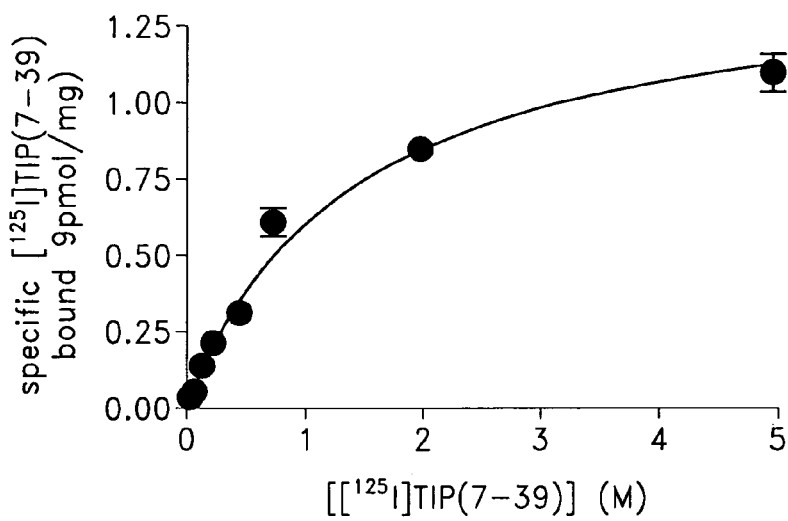
FIG. 22. Binding of [$^{125}$I]TIP(7–39) to the human PTH1 receptor. Radiolabeled TIP(7–39) was prepared and measurement of radioligand binding to the PTH1 receptor in HEK293 cell membranes performed as described in Examples. A. [$^{125}$I]TIP(7–39) saturation of the PTH1 receptor. Total binding data were analyzed using Equation 3. For presentation purposes the non-specific binding has been subtracted and specific binding values expressed as pmol radioligand bound per mg of membrane protein. Data points are mean±s.e.m. of triplicate determinations. The experiment was performed three times with similar results. In most cases the error bars are enclosed within the symbol. B. Dependence of the observed association rate constant ($k_{on\ (obs)}$) on [$^{125}$I]TIP(7–39) concentration. $k_{n(obs)}$ was obtained from analysis of association time course data. Linear regression analysis was performed on pooled data to obtain estimates of $k_{on}$ (provided by the gradient) and $k_{off}$ (provided by the y intercept). C. Dissociation time course. The line is the best fit of the data to a mono-exponential function. Non-specific binding in this experiment was 337 cpm (defined using 300 nM unlabeled TIP(7–39)). Data points are the mean±s.e.m. of triplicate measurements. The experiment was performed twice with similar results. In most cases the error bars are enclosed within the symbol.
Figure 22B:
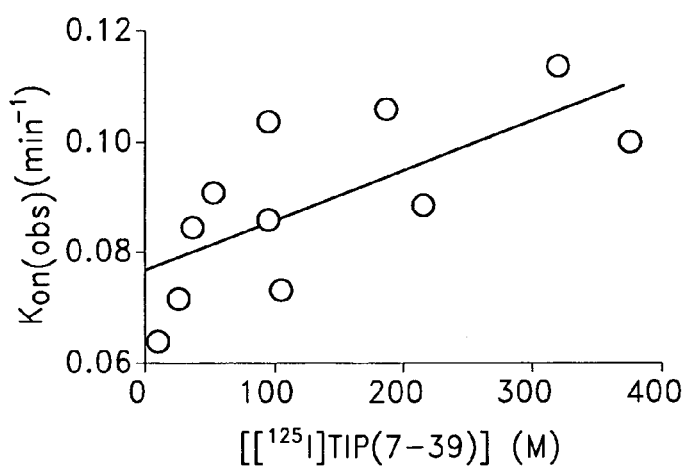
Figure 22C:
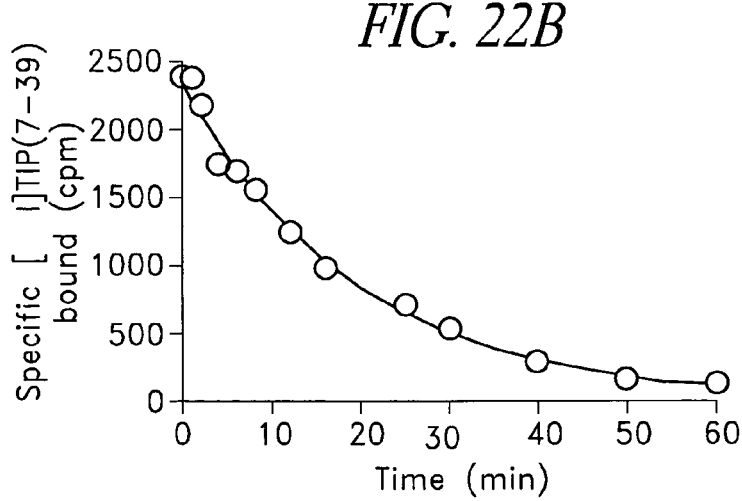

Association and dissociation of [$^{125}$I]TIP(7–39) binding to the PTH1 receptor was monophasic (FIG. 22) and the observed association rate constant appeared to be linearly dependent upon the concentration of radioligand (FIG. 22). These observations are consistent with a simple bi-molecular interaction between the receptor and radioligand. The kinetically-derived $K_D$ (0.57 nM) was in reasonable agreement with the $K_D$ measured directly in saturation experiments (1.3 nM, FIG. 22). The estimate of the dissociation rate constant from the plot of $k_{on(obs)}$ vs. concentration of radioligand (0.077 min$^{-1}$, from FIG. 22) was in good agreement with the directly measured value (0.051 min$^{-1}$, from FIG. 22).

Figure 23:
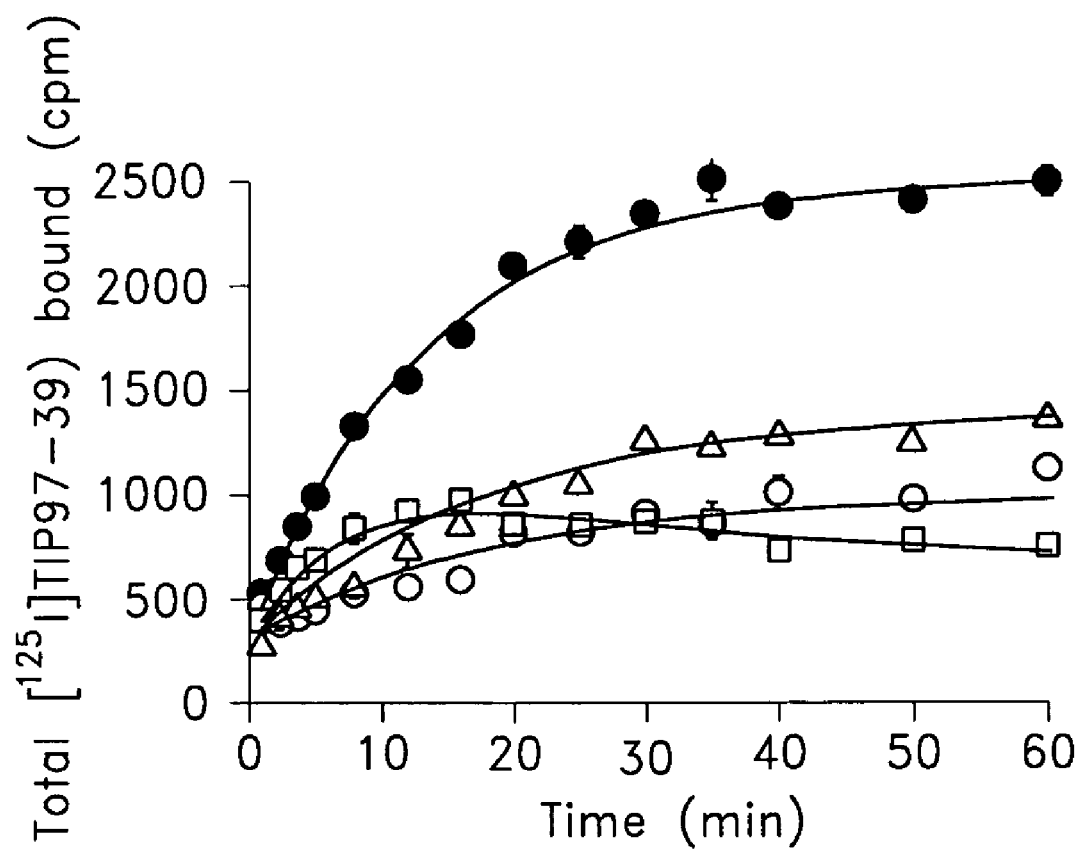
FIG. 23. Association of [$^{125}$I]TIP(7–39) to the human PTH1 receptor in the presence of a fixed concentration of unlabeled ligand. The time course of radioligand association with the PTH1 receptor in HEK293 cell membranes was measured as described in Examples, in the absence of unlabeled ligand (●) or in the presence of 60 nM [D-Tryp$^{12}$, Tyr$^{34}$]PTH(7–34) (○), 100 nM PTHrP(7–34) (Δ) or 3 nM [Nle$^{8,18}$, Tyr$^{34}$]PTH(3–34) (□). Association time course data in the presence of unlabeled ligand were fitted to Equation 4 to obtain estimates of $k_3$ and $k_4$, respectively the association and dissociation rate constants of the unlabeled ligand. In this experiment the following parameters were held constant in the analysis: $B_{max}$=31500 cpm, [L]=9.28× $10^{-11}$ M, bg=596 cpm, $k_1$=8.9×10$^7$ M$^{-1}$ min$^{-1}$, $k_2$=0.051 min$^{-1}$, [I] as given above. The curves are the best fits to the data. The slight over-shoot observed for [$^{125}$I]TIP(7–39) association in the presence of [Nle$^{8,18}$, Tyr$^{34}$]bPTH(3–34) is fitted well by Equation 4, arising from a lower value of $k_4$ than $k_2$ (Equation from Motulsky and Mahan, *Mol Pharmacol* 25: 1–9 (1984).) The data points are the mean±s.e.m. from triplicate determinations. Data are from a representative experiment. The experiments were performed twice (for [Nle$^{8,8}$, Tyr$^{34}$]PTH(3–34)) or three times (for the other two ligands) with very similar results. In most cases the error bars are enclosed within the symbol.

Association of [$^{125}$I]TIP(7–39) in the presence of the unlabeled antagonists (FIG. 23) was fitted well by a model that assumes competitive inhibition between the radioligand and unlabeled ligand. The model can account for the slight 'over-shoot' observed for the association of [$^{125}$I]TIP(7–39) in the presence of [Nle$^{8,18}$, Tyr$^{34}$]bPTH(3–34) (FIG. 23). Equation 4 was used to estimate the association and dissociation rate constants for the unlabeled ligands. The dissociation rate constant for both [D-Tryp$^{12}$, Tyr$^{34}$]PTH(7–34) and PTHrP(7–34) was much greater than the constant for [$^{125}$I]TIP(7–39). There was little difference between the values of the association rate constant for the three ligands. These findings indicate that the higher PTH1 receptor binding affinity of TIP(7–39) results from a considerably reduced rate of dissociation of the ligand from the receptor. The reliability of this indirect method for measuring the kinetic parameters was checked by comparing the kinetically-derived equilibrium dissociation constant with that measured in equilibrium binding assays. For all three unlabeled ligands tested the values obtained using the two methods were in good agreement. The $K_D$ of [Nle$^{8,18}$, Tyr$^{34}$]bPTH (3–34) for the PTH1 receptor (2.0 nM) has been reported previously. Further support for the reliability of the method is provided by a reasonable agreement between the dissociation rate constant for [Nle$^{8,18}$, Tyr$^{34}$]bPTH(3–34) estimated by Equation 4 (0.030±0.011 min$^{-1}$) and the value obtained by direct measurement of [$^{125}$I][Nle$^{8,18}$, Tyr$^{34}$] bPTH(3–34) dissociation (0.061±0.002 min$^{-1}$, n=2).

Reagents and Peptides

The following peptides were obtained from Bachem (Torrance, Calif.) or Peninsula Laboratories (Belmont, Calif.): [D-Tryp$^{12}$, Tyr$^{34}$]bPTH(7–34) amide, [Nle$^{8,18}$, D-Tryp$^{12}$, Tyr$^{34}$]bPTH(7–34) amide, PTHrP(7–34) amide, rPTH (1–34), [Nle$^{8,21}$, Tyr$^{34}$]rPTH(1–34) amide and [Nle$^{8,18}$, Tyr$^{34}$]bPTH(3–34) amide. The letters 'b' and 'r' designate the peptide sequence as bovine and rat, respectively. These peptides were dissolved in 10 mM acetic acid at a concentration of 1 mM, calculated using the peptide content and weight provided by the supplier. bTIP39 and bTIP(7–39) were purchased from Biomolecules Midwest (Waterloo, Ill.). bTIP(7–39) was quantified using the copper bicinchoninic acid method (Pierce, Rockford Ill.) with TIP39 as the standard. [$^{125}$I]cAMP was obtained from NEN (Boston, Mass.) and Na$^{125}$Iodine (2,000 Ci/mmol) was from ICN Biomedicals (Costa Mesa, Calif.). Lactose peroxidase was obtained from Sigma. Cell culture supplies were obtained from Life Technologies (Frederick, Md.), except for Dulbecco's Modified Eagle's Medium (DMEM) which was from Mediatech (Herndon, Va.). Fluo-4 acetoxymethyl ester and Pluronic F-127 were from Molecular Probes, Eugene, Oreg. Probenecid was from Sigma Preparation of Radioligands

[Nle$^{8,21}$, Tyr$^{34}$]rPTH(1–34) was prepared using chloramine T as catalyst followed by purification by HPLC, as previously described (Clark et al., Mol Endocrinol 12, 193–206, 1998). The di-iodinated form of the radioligand (4,000 Ci/mmol) was used in binding experiments. [$^{125}$I]TIP39 and [$^{125}$I]TIP(7–39) (2,000 Ci/mmol) were prepared using the lactose-peroxidase method described in Examples. TIP39 (5%g in 5 μl reaction buffer (0.1 M sodium acetate buffer pH 6.5)) was dispensed into a siliconized microfuge tube, followed by sequential addition of 0.5 mCi Na$^{125}$I, 5 μl of 20 μg/ml lactose peroxidase in reaction buffer, and 45 μl reaction buffer. After mixing, 10 μl of 0.001% H$_2$O$_2$ was added. After 20 minutes at room temperature the reaction was terminated by addition of 0.5 ml reaction buffer supplemented with 0.1% sodium azide. After a further five minutes, 0.5 ml reaction buffer supplemented with 1 M NaCl, 0.1% BSA and 1% potassium iodide was added. The radioligand was then de-salted using a C18 cartridge and purified by HPLC. The radioactive peak fractions corresponded with a single peak of UV absorbance.

Cell Culture of HEK293 Cells and Isolation of Cell Membranes

HEK293 cells stably expressing the human PTH1 or PTH2 receptor were grown as previously described (Usdin, Endocrinol 138, 831–838, 1997) P2 membrane preparations from HEK293 cells expressing the human PTH2 and PTH1 receptors were isolated as described in Examples. Membrane protein was quantified using the copper bicinchoninic acid method with BSA as the standard. Cell membranes were stored at −80° C. before use.

Cell Culture and Transient Expression in COS-7 Cells

COS-7 cells were grown as previously described in Clark et al. For cAMP accumulation assays COS-7 cells were transfected as previously described in Clark et al. except that transfections were performed in 10 cm tissue culture dishes using 10 μg of plasmid DNA. The cells were transferred following trypsinization to 96-well plates at a density of 50,000 cells/well the following day. Cells were used for assays of cAMP accumulation 3 days after transfection.

Radioligand Binding Assays

The centrifugation assay used for radioligand displacement assays (FIG. 17) is described in Examples. A similar assay design was used for the PTH1 and PTH2 receptor, in which radiolabeled agonist binding was displaced by the unlabeled ligands in the presence of 10 μM GTPγS. Briefly, cell membranes (45 μg), radioligand (50,000 cpm) and unlabeled ligand were incubated in a final volume of 1 ml assay buffer (20 mM HEPES, 100 mM NaCl, 1 mM EDTA, 3 mM MgSO$_4$ pH 7.5, supplemented with 0.3% non-fat dried milk powder, 100 μM (4-(2-aminoethyl))-benzenesulfonylflouride (AEBSF), 1 μg/ml bacitracin and 10 μM GTPγS) for two hours at 21° C. Membranes were collected at 18,000×g, the surface of the pellet gently washed and the radioactivity counted as described in Examples. For the PTH1 receptor, [$^{125}$I][Nle$^{8,21}$, Tyr$^{34}$]rPTH(1–34) was used as the radioligand at a final concentration of approximately 5 pM. [125I]TIP39 was used to label the PTH2 receptor at a concentration of 10 pM, assuming mono-iodination of TIP39 using the lactose peroxidase method. To prevent greater than 20% of the total radioligand added from binding to the membranes, 15–20 μg of membranes from transfected cells were used, made up to 45 μg with membranes from non-transfected cells.

Binding of [$^{125}$I]TIP(7–39) to HEK293 membranes expressing the PTH1 receptor (FIGS. 21 and 22) was performed using rapid filtration to separate bound and free radioligand as described in Examples, using the assay buffer described above. Incubations were carried out in 96-well polypropylene plates. The incubation mixture was transferred to a polyvinylidene fluoride filtration plate (MAHVN45, Millipore, Bedford, Mass.) and the membranes collected by rapid filtration using a Millipore Multiscreen vacuum manifold. In saturation experiments, varying concentrations of [$^{125}$I]TIP(7–39) were incubated in triplicate with 10 μg membranes in the absence or presence of 1 μM unlabeled TIP(7–39) (for measurement of total binding and non-specific binding, respectively) for 1 hour at 21° C. In radioligand association experiments, radioligand and buffer were brought to 21° C. by incubation in a water bath for 15 minutes. Similarly pre-warmed membranes were then added to the wells at various time points and the assay wells harvested simultaneously. Non-specific binding in these experiments was defined using 300 nM unlabeled TIP(7–39), incubated with membranes and radioligand for 1 minute and 60 minutes. In the experiment in FIG. 23 a second, unlabeled ligand was included in the assay incubation in order to estimate the association and dissociation rate constants of the unlabeled ligand (see below). In dissociation experiments radioligand and membranes were equilibrated for 60 minutes prior to addition of unlabeled TIP (7–39) (300 nM final concentration) at various time points. All time points were harvested simultaneously. (As a result the shorter time points of the time course were equilibrated with radioligand for between 1 and 2 hours.) Non-specific binding was defined using 300 nM unlabeled TIP(7–39), which was included in the equilibration phase of the assay.

Measurement of Cellular Levels of cAMP

Slightly different procedures were used depending on the experimental paradigm. For the experiment in FIG. 18, transfected COS-7 cells were treated for 40 min at 37° C. with 50 μl/well cAMP assay buffer (DMEM containing 25 mM HEPES supplemented with 0.1% bovine serum albumin, 30 μM Ro 20–1724 (RBI, Natick, Mass.), 100 μM (4-(2-aminoethyl))-benzenesulfonylflouride and 1 μg/ml bacitracin). This buffer was removed and replaced with 40 μl fresh buffer. Test agents were added in a volume of 10 µl and the cells incubated for an additional 40 min at 37° C. The assay was then terminated by the addition of 50 µl 0.1 N HCl, 0.1 mM CaCl$_2$. For measurement of PTH1 receptor antagonism by TIP(7–39) (FIG. 20) cells were washed with 100 µl DMEM then treated with 40 µl cAMP assay buffer containing varying concentrations of antagonist (or no antagonist for the control) for 30 minutes at 37° C. followed by addition of a range of concentrations of rPTH(1–34) in a volume of 10 µl. After a further 40 minutes at 37° C. the assay was terminated as described above. For measurement of the effect of human plasma on antagonist potency (FIG. 21) cells were treated for 40 minutes with 50 µl cAMP assay buffer. The buffer was removed and the following solutions added sequentially: 30 µl buffer containing plasma, 10 µl antagonist in buffer and 10 µl rPTH(1–34) in buffer. The cells were incubated at 37° C. for 40 minutes prior to assay termination. Human plasma was prepared by addition of EDTA to whole blood at a final concentration of 10 mM followed by centrifugation at 1,000×g for 10 minutes. The plasma supernatant was collected and stored in aliquots at −80° C. before use. cAMP was quantified using a RIA as previously described (Clark et al., supra).

Measurement of Intracellular Calcium Concentration

HEK293 cells stably expressing the PTH1 receptor were seeded in wells of a 96-well plate at 100,000 cells per well. The following day, medium was removed and the cells washed once with 0.1 ml Dulbecco's phosphate buffered saline containing 1 mM Ca$^{2+}$ and 1 mM Mg$^{2+}$ (DPBS). Cells were then loaded with 5 µM Fluo-4 acetoxymethyl ester, with 0.1% (w/v) Pluronic F-127 and 2.5 mM probenecid in DPBS for 1 hour at 37° C. Following two washes with DPBS supplemented with 0.1% BSA, cells were incubated in 0.1 ml of the same buffer for 30 min at 37° C. This buffer was then removed and 50 µl pre-warmed DPBS with BSA added. Baseline fluorescence was then measured for 80 sec at 37° C. in a Cytofluor 4,000 multiwell plate fluorimeter (PerSpective Biosystems, Framington, Mass.) (excitation wavelength 485±20 nM, emission wavelength 530±25 nM). Test agents were then added and fluorescence monitored as before. Fluorescence was measured in duplicate wells of cells for each experimental condition. Cytosolic free calcium concentration ($[Ca^{2+}]_i$) was calculated using the equation: $[Ca^{2+}]_i = K_D(F - F_{min})/(F_{max} - F)$ where $K_D$ is the ion dissociation constant (345 nM) for the indicator and F the fluorescence signal in arbitrary units. $F_{max}$ (maximum fluorescence at Ca$^{2+}$-saturation of the indicator) was determined by addition of 130 µM ionomycin and $F_{min}$ (background fluorescence) measured after addition of 20 mM EGTA.

Data Analysis

Concentration-dependence data for ligand-stimulated cAMP accumulation and inhibition of radioligand binding (FIGS. 17, 18, 20 and 21) was analyzed using the following four parameter-logistic equation using Prism 2.01 (GraphPad Software Inc., San Diego, Calif.):

$$y = \min + (\max - \min)/(1 + 10^{(Log\,K - X)n}) \quad \text{Equation 1}$$

where X is the logarithm of the ligand concentration and n is Hill slope. For cAMP accumulation data y is the amount of cAMP produced at a given peptide concentration, min is the cAMP level in the absence of ligand, max is the maximum level produced and K is the log EC$_{50}$. For inhibition of radioligand binding, y is the cpm bound at a given unlabeled ligand concentration, min is non-specific binding and max is total binding (the level of binding in the absence of unlabeled ligand) and K is the log IC$_{50}$.

The effect of TIP(7–39) on rPTH(1–34)-stimulated cAMP accumulation at the human PTH1 receptor was analyzed using Schild analysis (Arunlakshana and Schild, 1959) (FIG. 20), using the following equation:

$$\log(DR-1) = n \cdot \log[\text{antagonist}] + pA_2 \quad \text{Equation 2}$$

where DR is the dose-ratio (EC$_{50}$ in the presence of antagonist divided by EC$_{50}$ in the absence of antagonist), n is the gradient and pA$_2$ is a measure of the antagonist potency. The pA$_2$ was subsequently converted to a pK$_B$ value by fixing n at unity in the linear regression analysis.

[$^{125}$I]TIP(7–39) saturation of the PTH1 receptor was analyzed as follows: First, non-specific binding (measured in the presence of 1 µM TIP(7–39)) was estimated as a fraction of the free radioligand concentration by linear regression. The values of K$_D$ and B$_{max}$ were obtained by fitting total binding data (measured in the absence of unlabeled ligand) to the following equation using Prism 2.01:

$$\text{Total binding} = c \cdot [L] + \frac{B_{\max} \cdot [L]}{K_D + [L]} \quad \text{Equation 3}$$

where c is non-specific binding expressed as a fraction of the free radioligand concentration. c was fixed at the previously determined value from the analysis of non-specific binding values. The free radioligand concentration was calculated by subtracting either the non-specific binding value or the total binding value from the total radioligand concentration.

[$^{125}$I]TIP(7–39) association data (total binding) were fitted to a bi-exponential association equation to account for association to specific and non-specific sites (FIG. 23). This procedure was used because the value of non-specific binding measured after 60 minutes was slightly greater than the value measured after 1 minute. In the analysis the equilibrium level of non-specific binding was fixed at that measured at 60 minutes. The observed association rate constant for non-specific binding was high (>2 min$^{-1}$). The observed association rate of specific radioligand (L) binding ($k_{on(obs)}$) was fitted by linear regression to the equation $k_{on(obs)} = k_{off} + k_{on}[L]$ where $k_{on}$ and $k_{off}$ are the association and dissociation rate constants respectively. [$^{125}$I]TIP(7–39) dissociation data were fitted to a mono-exponential dissociation equation. A bi-exponential equation did not significantly improve the fit in all cases (p>0.7).

The association and dissociation rate constants of unlabeled ligands were determined using the method devised by Motulsky and Mahan, Mol Pharmacol 25, 1–9, 1984, in which association of a radiolabeled antagonist ([$^{125}$I]TIP(7–39)) is measured in the presence of a fixed concentration of the unlabeled ligand. The model assumes that the ligands bind in a competitive fashion according to simple bi-molecular reactions. The total amount of radioligand bound to the receptor ([RL]) as a function of time was fitted to the following equation using SigmaPlot 3.0 (Jandel Scientific, SPSS Inc., Chicago, Il):

$$[RL] = \frac{B_{\max} k_1 [L]}{K_F - K_S} \left[ \frac{k_4(K_F - K_S)}{K_F K_S} + \frac{(k_4 - K_F)}{K_F} \exp(-K_F t) - \frac{(k_4 - K_S)}{K_S} \exp(-K_S t) \right] + bg(1 - \exp(-K_{bg} t)) \quad \text{Equation 4}$$

where:

$$K_A = k_1[L] + k_2$$

$$K_B = k_3[I] + k_4$$

$$K_F = 0.5[(K_A + K_B + \sqrt{(K_A - K_B)^2 + 4k_1k_3[L][I]})]$$

$$K_S = 0.5[(K_A + K_B - \sqrt{(K_A - K_B)^2 + 4k_1k_3[L][I]})]$$

$k_1$ and $k_3$ are the association rate constants of the radioligand (L) and unlabeled ligand (I), respectively, $k_2$ and $k_4$ are the dissociation rate constants of the radioligand and unlabeled ligand, respectively, $B_{max}$ is the total concentration of receptors, bg is non-specific radioligand binding in cpm and $k_{bg}$ is the observed association rate constant for non-specific binding of radioligand. All parameters except $k_3$, $k_4$ and $k_{bg}$ were held constant in the analysis. $B_{max}$ was calculated using the equilibrium level of specific [$^{125}$I]TIP(7–39) binding (measured in parallel in each experiment), the concentration of radioligand and the kinetically-derived radioligand $K_D$, using the specific binding component of Equation 3.

Statistical comparison of multiple means was performed initially by single-factor analysis of variance followed by post-hoc analysis with the Newman-Keuls test. Statistical comparison of two means was performed using a two-tailed Student's t-test.

Example 12

Brain Administration of Tuberoinfundibular Peptide of 39 Residues Inhibits Growth Hormone Secretion Immunocytological localization of the PTH2 receptor suggested that the PTH2 receptor and TIP39 may play a role in the regulation of anterior pituitary hormone secretion. To test the hypothesis that TIP39, through the PTH2 receptor, may serve as a signal to the growth hormone (GH) neuroendocrine axis, we investigated the effect of centrally administered TIP39 on spontaneous GH secretion in conscious, freely behaving, adult rats. TIP39 was effective in blocking GH secretion for 3 hours after a single bolus injection. In contrast, TIP39 did not affect prolactin levels. These data suggest that TIP39 may be a potent and specific inhibitory regulator of GH secretion.

A GH peak detection program successfully identified peaks in the data plots where peaks were evident by eye. It detected a peak during the 3 hour experimental period in each individual vehicle-treated rat. In contrast, there were detectable peaks in only four out of the six TIP39-treated rats. Furthermore, all of the peaks in these six TIP39-treated rats were much smaller than those in the vehicle-treated rats. ICV administration of TIP39 resulted in significant suppression of GH secretion, in terms of the total area under the curve, peak area and peak amplitude, at a significance level of $p < 0.05$. TIP39 did not produce a statistically significant effect on the nadir values. Therefore the main effect seems to be a reduction in the size of the peaks, in some cases making them undetectable. There were no significant differences in prolactin levels measured in TIP39 treated versus control animals. The total areas under the curves were used as the measure. Median values of 5.2 for TIP39 vs. 6.6 ng/ml for vehicle were found.

Adult male Sprague-Dawley rats (Harlan, Indianapolis, Ind.) were housed individually in suspended stainless steel cages. The room was temperature-controlled at 18–21° C. and on a 12L:12D cycle with the lights on at 0700 h. Animals had free access to ground PMI Rodent chow #5012 (Richmond, Ind.) and tap water unless otherwise noted. Guide cannulae were implanted in a lateral ventricle and an angiotensin II drinking test was performed to verify the cannula placement one week after surgery, as previously described (5). Under methoxyflurane (Metafan®, Pittman-Moore, NJ) anesthesia a sialastic catheter was placed into the jugular vein, terminating at the junction of the anterior vena cava and the right atrium, tied in place, tunneled subcutaneously to the shoulder region, externalized through a small skin incision and sutured in the interscapular region. The catheter was filled with 5 IU/mL of heparin. Rats were injected subcutaneously with 0.3 ml saline containing 80 mg/mL of sulfamethoxazole and 16 mg/mL of Trimethoprim (ELKINS-SINN, Cherry Hill, N.J.) before the catheterization surgery and for 2 days after surgery. Care was taken to minimize the number of animals used and their suffering. All procedures were performed according to animal care protocols approved by the University of Georgia animal use and care committee.

On the day of the experiment the rats were weighed and the catheter was flushed with 0.1 ml of 5 IU/ml heparin two hours before the first sampling. Food and water were removed from the cages a half-hour before the first sampling. The catheter was connected through a length of polyethylene tubing to a 1 ml syringe that was outside the cage and filled with 0.3 ml of 5 IU/mL heparin. The syringe was replaced with a new one for blood collection. Rats were not handled during the sampling period.

TIP39 was synthesized by Anaspec Inc (San Jose, Calif.) and dissolved in vehicle (water) at a concentration of 10 mg/10 ml. Control animals were injected with water pH adjusted to match the peptide solution (approximately pH 5). Twelve rats were randomly assigned into two treatment groups, i.e., 10 mg of TIP39 injected (body weight 297±7 g; n=6) and 10 ml of vehicle injected (body weight 303±7 g; n=6). We failed to withdraw blood from two rats in the vehicle injected control group during the sampling period of 75 to 180 min due to a clotted catheter. Therefore, the final sample sizes were 6 and 4 for the TIP39 injected group and vehicle injected group, respectively. The first blood sample was taken at approximately 10:00 h followed by intracerebroventricular injection of 10 ml of vehicle or 10 mg of TIP39. The ICV injection procedure was previously described (5). Blood samples (0.15 ml) were then taken very 15 min up to 3 h. To avoid dilution errors related to dead space, 0.1 ml blood was removed prior to the collection of each sample, and then returned to the animal following removal of that sample.

Following centrifugation, the plasma was stored at −70° C., and the red blood cells were resuspended in physiological sterile saline and returned to the animal after the subsequent sample was removed, to prevent hemodynamic disturbance. Plasma GH and prolactin were measured in duplicate samples by radioimmunoassay. The GH data were analyzed using a peak detection program that fit a Gaussian curve and a baseline to the measured points. The fit parameters were the position (mean time), width (standard deviation), peak area (area under the Gaussian) and an additive base value. The program was written using standard non-linear fitting techniques available in the Mathematica (Wol fram Research, Inc., Champaign, Ill.) language. Total areas under experimental data curves were calculated using integration of third order (cubic) interpolation functions. Peak height was the maximum data point, not the height of the Gaussian. Total area under the curve, peak area, peak amplitude and nadir values were analyzed with a Mann-Whitney U test in Statview (Abacus Concepts, Inc., Palo Alto, Calif.). Results are reported as medians. The prolactin data were analyzed with area under the curve only, as there were no peaks. Again, a Mann-Whitney U test was performed to examine the difference between the area under the curve of the two treatment groups. A p-value of less than 0.05 was considered significant.

APPENDIX

A fragment of bovine genomic DNA sequence was aligned with a fragment of human genomic sequence. The upper line of sequence is bovine (SEQ ID NO: 107) and the lower line human (SEQ ID NO: 108). The nucleotide number 593 (arbitrary) corresponds to the first amino acid of protein-sequenced TIP39. The bovine genomic sequence was obtained by PCR using degenerate primers based on the amino acid sequence of TIP39.

```
                      ----------------------------------------------------------------------------------
            13501  gacggtccttccgccagtctctattttagccctctgacacaccccctgtgtccacctctctgtctgtctgtctctcccc 13580
                         .         13520          .         13540         .        13560          .       13580

----------------------------------------------------------------------------------
            13581  ctccctcgtctcaggtccagcttctggtcccaattagttggtggcggccaaggcagcggcaggtccccaccccggctc 13660
                         .         13600          .         13620         .        13640          .       13660

----------------------------------------------------------------------------------
            13661  ctcattaccgctggcggctcctaatgagcctggggaggggtgaccccgcgtcccggccccccggcctgcgtcactgcc 13740
                         .         13680          .         13700         .        13720          .       13740

----------------------------------------------------------------------------------
            13741  cggtgcggggctgcggaggcgatataaggggctgccaccatcgctgccccagcccactgcacggtaggggactgtgcg 13820
                         .         13760          .         13780         .        13800          .       13820

.
               1   ----------------------------------------------TTC-GCCCTAC--------------------- 10
                                                                 | |  |||||||
           13821  ggaagctgggggtggatgcatggtggggcccggggttctgggccggatgcagccctactgagccccttctggttctcc 13900
                         .         13840          .         13860         .        13880          .       13900

11   ---------------------------------------------------------------------CTCCTTG 17
                                                                                        | |
           13901  acaggtgatggagacccgccaggtgtccaggagccctcggggttcggctgctgctgctgctgctgctggtggtgc 13980
                         .         13920          .         13940         .        13960          .       13980

20                                                             .        40           .
              18   GC-GGGGCGTC----------------------------------------TTTCA-GTAAGTGGACATCCAAG-CCTCCCA 56
                   |  ||||||||                                         ||| ||| |||      ||| ||  ||||||
           13981  cctggggcgtccgcactgcctcgggagtcgccctgccccggtcgggtcctcaggtaggtgccagtcccagaactccca 14060
                         .         14000          .         14020         .        14040          .       14060

60
              57   GGGA---------------------------------------------------------------------- 60
                   ||||
           14061  gggaggggtgggaacttggagaagtgggaagagaaccaaagagaaagggacggaagatccagaaagcggaacagaagcc 14140
                         .         14080          .         14100         .        14120          .       14140

.              80
              61   --------------------------------------AGGGTGGGG-ACTCCGAGAGGT---------------- 81
                                                         ||||||||| |  ||  ||||
           14141  caaagagagggcgaccgagacccagcgagaagacagagactaggggtgggggaaggcgggaggagggtttggtggtagtg 14220
                         .         14160          .         14180         .        14200          .       14220

.       100        .        120
              82   ------------------------------GGAAAGAGACCCGAAAAGAATGGGAACAAAGACTCAGAAAAAAAGGG 129
                                                 |||||||||||  |  ||
           14221  gtggtgcgggaaatggacagaaaatcagcaagggaaagagacacagaa============================= 14268
                         .         14240          .         14260

.       140        .       160        .       180        .        200
             130   GGAAATAGAGACCCAGAGAGGAGGCCAGAGATAGGAGGTTGACAGGTAGGTAATCTGCAAAATAAAGAGATACAAAAGGA 209
                                                         ||||||                                   |
           14269  ==========================================agatag=====================================a 14275

.       220        .       240        .       260        .        280
             210   TTCTGAGAAAGGCTTTGAGAGACTTGAAAGGAGTCGAAGCAGGAACGAGTTTGTTCCTTGAGCAACGTTTATTGGGTCTG 289
                   | | ||||||||| |  |||||| || ||||||||||||  |||| ||||  |||  ||||||||||||||||||||||||
           14276  tcccgagaaaggcgtggagaggctcgaaaggagtcgttgcagaaacggattcattctttgagcaacgtttattgggttct 14355
                       14280         .       14300         .       14320         .       14340          .
```

```
              .        300          .        320          .        340          .
         290  GGGTGTGTGCCACGCGTGCGCC------------GAGCACTGGGGCGGGACAGGGGCATCAGACTCGGTCTCTGTAC-TC  356
              |||  ||||||           ||||  |||  |||||  |  |||||||||||||||||||||||  ||
       14356  tggt==========gtgcgcctggccatgcgctgagcgctgtgggcggacaagtgcatcagactcggtctcagtacctg  14424
                            14360         .         14380         .         14400         .         14420

.        360          .        380          .        400          .        420
         357  AGGAGGCTCGGAACTGGTGAACACTGAGCCGAAGACTCACACAGAGCAAGAGACAGGAGACAGAGACC------------  424
              ||||  |||  |  ||||||||  ||                                 |||||||||||||
       14425  gggagtttcgaacctggtgagcaga=================================gagacagagacccacacagagaac  14473
                         .         14440                                 .         14460         .

.        440          .        460          .
         425  -----------------------GAGCCCCTCCGCAT-CTGGTGCAGTCACAGGGCTTCGAGTTAGACCGCGGGGAGAA  479
                                   ||||  ||||  |    ||||  |||||  ||  ||||||||||||||||||||  |
       14474  gagagagacaggggggagccggaccgagccactccacggactgg=gcagtaacggggcttcgagttagaccgcggggagga  14552
                   14480         .         14500         .         14520         .         14540         .

.        480          .        500          .        520
         480  CAGGCGGCGGGCCGCG-G-GCCGAGACCCACGGTAACCGCCTCTTTCCATC---------------------------  528
              ||||||||||  |    |  |||  |  ||||  ||||   |||  ||||
       14553  caggcggcggcaagagcgagtctggacgcgcggtcaccgcgtctctccacagcctccgcccccaggacgggcctgggcg  14632
                         .         14560         .         14580         .         14600         .         14620         .

.        540          .        560          .        580          .        600
         529  --TCCCGGCAGACTCCGCACCCCCGGCGAGGCTCGGGCGGGTCCGGCCACCCCCCAGTCGCGGCGGAGCCTGGCGCTGGC  606
                ||||                                              ||||||  |  |||||  ||||||||||||
       14633  gatccc=========================================gccaccccccaggccgcggaggagcctggcgctggc  14673
                                                                         14640         .         14660         .

.        620          .        640          .        660          .        680
         607  GGACGACGCGGCCTTCCGGGAGCGCGCGCGGCTGCTGGCCGCCCTCGAGCGCCGCCACTGGCTGAACTCGTACATGCACA  686
              |||||||||||||||||||||||||| |||||| ||||||||||||||||||||||||||||||||||||||||||||
       14674  ggacgacgcggccttccgggagcgcgcgcggttgctggccgcccctcgagcgccgccactggctgaactcgtacatgcaca  14753
                         .         14680         .         14700         .         14720         .         14740         .

.        700          .        720          .        740          .        760
         687  AGCTGCTGGTGCTGGACGCGCCCTGAGCGC-CTGCCCG-CCCCACCTCAATAAAGACCGTGCTGTGC-CTCCCGACTGCG  763
              ||||||||||  |||| ||||||||||||| ||||||  |||||  || ||||||||||||  |||  |||| ||||||
       14754  agctgctggtgttggatgcgccctgagcgcgctgcccgtcccatcttaataaagaccatgccctgcgctccggactgcg  14833
                         .         14760         .         14780         .         14800         .         14820         .

.        780          .        800          .
         764  CCTCCTTCCT--ACG-CCT-CGTGTGCGTGTGGTGGTGGTGGTGTGTG----------------------------  810
              ||||   |||  |||  ||| |  |||||  |||  |  |  |  |  |
       14834  cctcgttcctgcgcgacctgcgtgtgcgttgggttggggcgcggggcttgaaatgggggtacaaaagagacacgactc  14913
                      14840         .         14860         .         14880         .         14900         .

.
         811  TGTGTCTAC--------------------------------------------------------------------  819
              ||||||  |
       14914  tgtgtcggccactctggcatctctctcctcagtccccactctattttctttcctcaattccgtttctctctgcctgtctt  14993
                         14920         .         14940         .         14960         .         14980         .

----------------------
       14994  tgtccaggaagctggcttcttt                                                          15015
                      15000         .
```

While particular embodiments of the invention have been described in detail, it will be apparent to those of ordinary skill in the art that these embodiments are exemplary, rather than limiting. The true scope of the invention is that defined within the attached claims and equivalents thereof. All references cited herein are hereby expressly incorporated by reference.

The invention claimed is:

1. An isolated or purified peptide comprising the sequence of SEQ ID NO: 1, wherein isolated is defined as separated from the remainder of the coexisting materials in the hypothalamus gland and purified is defined as permitting accurate amino acid sequence determination.

* * * * *

SEQUENCE LISTING

<160> NUMBER OF SEQ ID NOS: 112

<210> SEQ ID NO 1
<211> LENGTH: 39
<212> TYPE: PRT
<213> ORGANISM: Bos taurus

<400> SEQUENCE: 1

-continued

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His Lys
                20                  25                  30

Leu Leu Val Leu Asp Ala Pro
            35

<210> SEQ ID NO 2
<211> LENGTH: 38
<212> TYPE: PRT
<213> ORGANISM: Bos taurus

<400> SEQUENCE: 2

Leu Ala Leu Ala Asp Asp Ala Ala Phe Arg Glu Arg Ala Arg Leu Leu
1               5                   10                  15

Ala Ala Leu Glu Arg Arg His Trp Leu Asn Ser Tyr Met His Lys Leu
                20                  25                  30

Leu Val Leu Asp Ala Pro
            35

<210> SEQ ID NO 3
<211> LENGTH: 37
<212> TYPE: PRT
<213> ORGANISM: Bos taurus

<400> SEQUENCE: 3

Ala Leu Ala Asp Asp Ala Ala Phe Arg Glu Arg Ala Arg Leu Leu Ala
1               5                   10                  15

Ala Leu Glu Arg Arg His Trp Leu Asn Ser Tyr Met His Lys Leu Leu
                20                  25                  30

Val Leu Asp Ala Pro
        35

<210> SEQ ID NO 4
<211> LENGTH: 36
<212> TYPE: PRT
<213> ORGANISM: Bos taurus

<400> SEQUENCE: 4

Leu Ala Asp Asp Ala Ala Phe Arg Glu Arg Ala Arg Leu Leu Ala Ala
1               5                   10                  15

Leu Glu Arg Arg His Trp Leu Asn Ser Tyr Met His Lys Leu Leu Val
                20                  25                  30

Leu Asp Ala Pro
        35

<210> SEQ ID NO 5
<211> LENGTH: 35
<212> TYPE: PRT
<213> ORGANISM: Bos taurus

<400> SEQUENCE: 5

Ala Asp Asp Ala Ala Phe Arg Glu Arg Ala Arg Leu Leu Ala Ala Leu
1               5                   10                  15

Glu Arg Arg His Trp Leu Asn Ser Tyr Met His Lys Leu Leu Val Leu
                20                  25                  30

Asp Ala Pro
        35

<210> SEQ ID NO 6

```
<211> LENGTH: 34
<212> TYPE: PRT
<213> ORGANISM: Bos taurus

<400> SEQUENCE: 6

Asp Asp Ala Ala Phe Arg Glu Arg Ala Arg Leu Leu Ala Ala Leu Glu
 1               5                  10                  15

Arg Arg His Trp Leu Asn Ser Tyr Met His Lys Leu Leu Val Leu Asp
            20                  25                  30

Ala Pro

<210> SEQ ID NO 7
<211> LENGTH: 33
<212> TYPE: PRT
<213> ORGANISM: Bos taurus

<400> SEQUENCE: 7

Asp Ala Ala Phe Arg Glu Arg Ala Arg Leu Leu Ala Ala Leu Glu Arg
 1               5                  10                  15

Arg His Trp Leu Asn Ser Tyr Met His Lys Leu Leu Val Leu Asp Ala
            20                  25                  30

Pro

<210> SEQ ID NO 8
<211> LENGTH: 32
<212> TYPE: PRT
<213> ORGANISM: Bos taurus

<400> SEQUENCE: 8

Ala Ala Phe Arg Glu Arg Ala Arg Leu Leu Ala Ala Leu Glu Arg Arg
 1               5                  10                  15

His Trp Leu Asn Ser Tyr Met His Lys Leu Leu Val Leu Asp Ala Pro
            20                  25                  30

<210> SEQ ID NO 9
<211> LENGTH: 31
<212> TYPE: PRT
<213> ORGANISM: Bos taurus

<400> SEQUENCE: 9

Ala Phe Arg Glu Arg Ala Arg Leu Leu A-
la Ala Leu Glu Arg Arg His                5                  10                  1
 1       51015

Trp Leu Asn Ser Tyr Met His Lys Leu Leu Val Leu Asp Ala Pro
            202530

<210> SEQ ID NO 10
<211> LENGTH: 30
<212> TYPE: PRT
<213> ORGANISM: Bos taurus

<400> SEQUENCE: 10

Phe Arg Glu Arg Ala Arg Leu Leu Ala Ala Leu Glu Arg Arg His Trp
 1               5                  10                  15

Leu Asn Ser Tyr Met His Lys Leu Leu Val Leu Asp Ala Pro
            20                  25                  30

<210> SEQ ID NO 11
<211> LENGTH: 29
<212> TYPE: PRT
<213> ORGANISM: Bos taurus
```

-continued

```
<400> SEQUENCE: 11

Arg Glu Arg Ala Arg Leu Leu Ala Ala Leu Glu Arg Arg His Trp Leu
1               5                   10                  15

Asn Ser Tyr Met His Lys Leu Leu Val Leu Asp Ala Pro
            20                  25

<210> SEQ ID NO 12
<211> LENGTH: 28
<212> TYPE: PRT
<213> ORGANISM: Bos taurus

<400> SEQUENCE: 12

Glu Arg Ala Arg Leu Leu Ala Ala Leu Glu Arg Arg His Trp Leu Asn
1               5                   10                  15

Ser Tyr Met His Lys Leu Leu Val Leu Asp Ala Pro
            20                  25

<210> SEQ ID NO 13
<211> LENGTH: 27
<212> TYPE: PRT
<213> ORGANISM: Bos taurus

<400> SEQUENCE: 13

Arg Ala Arg Leu Leu Ala Ala Leu Glu Arg Arg His Trp Leu Asn Ser
1               5                   10                  15

Tyr Met His Lys Leu Leu Val Leu Asp Ala Pro
            20                  25

<210> SEQ ID NO 14
<211> LENGTH: 26
<212> TYPE: PRT
<213> ORGANISM: Bos taurus

<400> SEQUENCE: 14

Ala Arg Leu Leu Ala Ala Leu Glu Arg Arg His Trp Leu Asn Ser Tyr
1               5                   10                  15

Met His Lys Leu Leu Val Leu Asp Ala Pro
            20                  25

<210> SEQ ID NO 15
<211> LENGTH: 25
<212> TYPE: PRT
<213> ORGANISM: Bos taurus

<400> SEQUENCE: 15

Arg Leu Leu Ala Ala Leu Glu Arg Arg His Trp Leu Asn Ser Tyr Met
1               5                   10                  15

His Lys Leu Leu Val Leu Asp Ala Pro
            20                  25

<210> SEQ ID NO 16
<211> LENGTH: 24
<212> TYPE: PRT
<213> ORGANISM: Bos taurus

<400> SEQUENCE: 16

Leu Leu Ala Ala Leu Glu Arg Arg His Trp Leu Asn Ser Tyr Met His
1               5                   10                  15

Lys Leu Leu Val Leu Asp Ala Pro
            20
```

```
<210> SEQ ID NO 17
<211> LENGTH: 23
<212> TYPE: PRT
<213> ORGANISM: Bos taurus

<400> SEQUENCE: 17

Leu Ala Ala Leu Glu Arg Arg His Trp Leu Asn Ser Tyr Met His Lys
1               5                   10                  15

Leu Leu Val Leu Asp Ala Pro
            20

<210> SEQ ID NO 18
<211> LENGTH: 22
<212> TYPE: PRT
<213> ORGANISM: Bos taurus

<400> SEQUENCE: 18

Ala Ala Leu Glu Arg Arg His Trp Leu Asn Ser Tyr Met His Lys Leu
1               5                   10                  15

Leu Val Leu Asp Ala Pro
            20

<210> SEQ ID NO 19
<211> LENGTH: 21
<212> TYPE: PRT
<213> ORGANISM: Bos taurus

<400> SEQUENCE: 19

Ala Leu Glu Arg Arg His Trp Leu Asn Ser Tyr Met His Lys Leu Leu
1               5                   10                  15

Val Leu Asp Ala Pro
            20

<210> SEQ ID NO 20
<211> LENGTH: 20
<212> TYPE: PRT
<213> ORGANISM: Bos taurus

<400> SEQUENCE: 20

Leu Glu Arg Arg His Trp Leu Asn Ser Tyr Met His Lys Leu Leu Val
1               5                   10                  15

Leu Asp Ala Pro
            20

<210> SEQ ID NO 21
<211> LENGTH: 19
<212> TYPE: PRT
<213> ORGANISM: Bos taurus

<400> SEQUENCE: 21

Glu Arg Arg His Trp Leu Asn Ser Tyr Met His Lys Leu Leu Val Leu
1               5                   10                  15

Asp Ala Pro

<210> SEQ ID NO 22
<211> LENGTH: 18
<212> TYPE: PRT
<213> ORGANISM: Bos taurus

<400> SEQUENCE: 22

Arg Arg His Trp Leu Asn Ser Tyr Met His Lys Leu Leu Val Leu Asp
1               5                   10                  15
```

Ala Pro

<210> SEQ ID NO 23
<211> LENGTH: 17
<212> TYPE: PRT
<213> ORGANISM: Bos taurus

<400> SEQUENCE: 23

Arg His Trp Leu Asn Ser Tyr Met His Lys Leu Leu Val Leu Asp Ala
 1               5                  10                  15
Pro

<210> SEQ ID NO 24
<211> LENGTH: 16
<212> TYPE: PRT
<213> ORGANISM: Bos taurus

<400> SEQUENCE: 24

His Trp Leu Asn Ser Tyr Met His Lys Leu Leu Val Leu Asp Ala Pro
 1               5                  10                  15

<210> SEQ ID NO 25
<211> LENGTH: 15
<212> TYPE: PRT
<213> ORGANISM: Bos taurus

<400> SEQUENCE: 25

Trp Leu Asn Ser Tyr Met His Lys Leu Leu Val Leu Asp Ala Pro
 1               5                  10                  15

<210> SEQ ID NO 26
<211> LENGTH: 14
<212> TYPE: PRT
<213> ORGANISM: Bos taurus

<400> SEQUENCE: 26

Leu Asn Ser Tyr Met His Lys Leu Leu Val Leu Asp Ala Pro
 1               5                  10

<210> SEQ ID NO 27
<211> LENGTH: 13
<212> TYPE: PRT
<213> ORGANISM: Bos taurus

<400> SEQUENCE: 27

Asn Ser Tyr Met His Lys Leu Leu Val Leu Asp Ala Pro
 1               5                  10

<210> SEQ ID NO 28
<211> LENGTH: 12
<212> TYPE: PRT
<213> ORGANISM: Bos taurus

<400> SEQUENCE: 28

Ser Tyr Met His Lys Leu Leu Val Leu Asp Ala Pro
 1               5                  10

<210> SEQ ID NO 29
<211> LENGTH: 11
<212> TYPE: PRT
<213> ORGANISM: Bos taurus

<400> SEQUENCE: 29

Tyr Met His Lys Leu Leu Val Leu Asp Ala Pro 1               5                    10

<210> SEQ ID NO 30
<211> LENGTH: 10
<212> TYPE: PRT
<213> ORGANISM: Bos taurus

<400> SEQUENCE: 30

Met His Lys Leu Leu Val Leu Asp Ala Pro
 1               5                    10

<210> SEQ ID NO 31
<211> LENGTH: 9
<212> TYPE: PRT
<213> ORGANISM: Bos taurus

<400> SEQUENCE: 31

His Lys Leu Leu Val Leu Asp Ala Pro
 1               5

<210> SEQ ID NO 32
<211> LENGTH: 8
<212> TYPE: PRT
<213> ORGANISM: Bos taurus

<400> SEQUENCE: 32

Lys Leu Leu Val Leu Asp Ala Pro
 1               5

<210> SEQ ID NO 33
<211> LENGTH: 7
<212> TYPE: PRT
<213> ORGANISM: Bos taurus

<400> SEQUENCE: 33

Leu Leu Val Leu Asp Ala Pro
 1               5

<210> SEQ ID NO 34
<211> LENGTH: 6
<212> TYPE: PRT
<213> ORGANISM: Bos taurus

<400> SEQUENCE: 34

Leu Val Leu Asp Ala Pro
 1               5

<210> SEQ ID NO 35
<211> LENGTH: 5
<212> TYPE: PRT
<213> ORGANISM: Bos taurus

<400> SEQUENCE: 35

Val Leu Asp Ala Pro
 1               5

<210> SEQ ID NO 36
<211> LENGTH: 4
<212> TYPE: PRT
<213> ORGANISM: Bos taurus

<400> SEQUENCE: 36

Leu Asp Ala Pro
 1

<210> SEQ ID NO 37
<211> LENGTH: 3
<212> TYPE: PRT
<213> ORGANISM: Bos taurus

<400> SEQUENCE: 37

Asp Ala Pro
1

<210> SEQ ID NO 38
<211> LENGTH: 38
<212> TYPE: PRT
<213> ORGANISM: Bos taurus

<400> SEQUENCE: 38

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His Lys
            20                  25                  30

Leu Leu Val Leu Asp Ala
        35

<210> SEQ ID NO 39
<211> LENGTH: 37
<212> TYPE: PRT
<213> ORGANISM: Bos taurus

<400> SEQUENCE: 39

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His Lys
            20                  25                  30

Leu Leu Val Leu Asp
        35

<210> SEQ ID NO 40
<211> LENGTH: 36
<212> TYPE: PRT
<213> ORGANISM: Bos taurus

<400> SEQUENCE: 40

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His Lys
            20                  25                  30

Leu Leu Val Leu
        35

<210> SEQ ID NO 41
<211> LENGTH: 35
<212> TYPE: PRT
<213> ORGANISM: Bos taurus

<400> SEQUENCE: 41

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His Lys
            20                  25                  30

Leu Leu Val
        35

<210> SEQ ID NO 42
<211> LENGTH: 34
<212> TYPE: PRT
<213> ORGANISM: Bos taurus

<400> SEQUENCE: 42

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His Lys
            20                  25                  30

Leu Leu

<210> SEQ ID NO 43
<211> LENGTH: 33
<212> TYPE: PRT
<213> ORGANISM: Bos taurus

<400> SEQUENCE: 43

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His Lys
            20                  25                  30

Leu

<210> SEQ ID NO 44
<211> LENGTH: 32
<212> TYPE: PRT
<213> ORGANISM: Bos taurus

<400> SEQUENCE: 44

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His Lys
            20                  25                  30

<210> SEQ ID NO 45
<211> LENGTH: 31
<212> TYPE: PRT
<213> ORGANISM: Bos taurus

<400> SEQUENCE: 45

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met His
            20                  25                  30

<210> SEQ ID NO 46
<211> LENGTH: 30
<212> TYPE: PRT
<213> ORGANISM: Bos taurus

<400> SEQUENCE: 46

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr Met
            20                  25                  30

<210> SEQ ID NO 47
<211> LENGTH: 29
<212> TYPE: PRT
<213> ORGANISM: Bos taurus

-continued

<400> SEQUENCE: 47

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser Tyr
            20                  25

<210> SEQ ID NO 48
<211> LENGTH: 28
<212> TYPE: PRT
<213> ORGANISM: Bos taurus

<400> SEQUENCE: 48

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn Ser
            20                  25

<210> SEQ ID NO 49
<211> LENGTH: 27
<212> TYPE: PRT
<213> ORGANISM: Bos taurus

<400> SEQUENCE: 49

Ser Leu Ala Leu Ala Asp Asp Ala Ala Phe Arg Glu Arg Ala Arg Leu
1               5                   10                  15

Leu Ala Ala Leu Glu Arg Arg His Trp Leu Asn
            20                  25

<210> SEQ ID NO 50
<211> LENGTH: 26
<212> TYPE: PRT
<213> ORGANISM: Bos taurus

<400> SEQUENCE: 50

Ser Leu Ala Leu Ala Asp Asp Ala Ala Phe Arg Glu Arg Ala Arg Leu
1               5                   10                  15

Leu Ala Ala Leu Glu Arg Arg His Trp Leu
            20                  25

<210> SEQ ID NO 51
<211> LENGTH: 25
<212> TYPE: PRT
<213> ORGANISM: Bos taurus

<400> SEQUENCE: 51

Ser Leu Ala Leu Ala Asp Asp Ala Ala Phe Arg Glu Arg Ala Arg Leu
1               5                   10                  15

Leu Ala Ala Leu Glu Arg Arg His Trp
            20                  25

<210> SEQ ID NO 52
<211> LENGTH: 24
<212> TYPE: PRT
<213> ORGANISM: Bos taurus

<400> SEQUENCE: 52

Ser Leu Ala Leu Ala Asp Asp Ala Ala Phe Arg Glu Arg Ala Arg Leu
1               5                   10                  15

Leu Ala Ala Leu Glu Arg Arg His
            20

```
<210> SEQ ID NO 53
<211> LENGTH: 23
<212> TYPE: PRT
<213> ORGANISM: Bos taurus

<400> SEQUENCE: 53

Ser Leu Ala Leu Ala Asp Asp Ala Ala Phe Arg Glu Arg Ala Arg Leu
 1               5                  10                  15

Leu Ala Ala Leu Glu Arg Arg
            20

<210> SEQ ID NO 54
<211> LENGTH: 22
<212> TYPE: PRT
<213> ORGANISM: Bos taurus

<400> SEQUENCE: 54

Ser Leu Ala Leu Ala Asp Asp Ala Ala Phe Arg Glu Arg Ala Arg Leu
 1               5                  10                  15

Leu Ala Ala Leu Glu Arg
            20

<210> SEQ ID NO 55
<211> LENGTH: 21
<212> TYPE: PRT
<213> ORGANISM: Bos taurus

<400> SEQUENCE: 55

Ser Leu Ala Leu Ala Asp Asp Ala Ala Phe Arg Glu Arg Ala Arg Leu
 1               5                  10                  15

Leu Ala Ala Leu Glu
            20

<210> SEQ ID NO 56
<211> LENGTH: 20
<212> TYPE: PRT
<213> ORGANISM: Bos taurus

<400> SEQUENCE: 56

Ser Leu Ala Leu Ala Asp Asp Ala Ala Phe Arg Glu Arg Ala Arg Leu
 1               5                  10                  15

Leu Ala Ala Leu
            20

<210> SEQ ID NO 57
<211> LENGTH: 19
<212> TYPE: PRT
<213> ORGANISM: Bos taurus

<400> SEQUENCE: 57

Ser Leu Ala Leu Ala Asp Asp Ala Ala Phe Arg Glu Arg Ala Arg Leu
 1               5                  10                  15

Leu Ala Ala

<210> SEQ ID NO 58
<211> LENGTH: 18
<212> TYPE: PRT
<213> ORGANISM: Bos taurus

<400> SEQUENCE: 58

Ser Leu Ala Leu Ala Asp Asp Ala Ala Phe Arg Glu Arg Ala Arg Leu
 1               5                  10                  15
```

Leu Ala

<210> SEQ ID NO 59
<211> LENGTH: 17
<212> TYPE: PRT
<213> ORGANISM: Bos taurus

<400> SEQUENCE: 59

Ser Leu Ala Leu Ala Asp Asp Ala Ala Phe Arg Glu Arg Ala Arg Leu
1               5                   10                  15
Leu

<210> SEQ ID NO 60
<211> LENGTH: 16
<212> TYPE: PRT
<213> ORGANISM: Bos taurus

<400> SEQUENCE: 60

Ser Leu Ala Leu Ala Asp Asp Ala Ala Phe Arg Glu Arg Ala Arg Leu
1               5                   10                  15

<210> SEQ ID NO 61
<211> LENGTH: 15
<212> TYPE: PRT
<213> ORGANISM: Bos taurus

<400> SEQUENCE: 61

Ser Leu Ala Leu Ala Asp Asp Ala Ala Phe Arg Glu Arg Ala Arg
1               5                   10                  15

<210> SEQ ID NO 62
<211> LENGTH: 14
<212> TYPE: PRT
<213> ORGANISM: Bos taurus

<400> SEQUENCE: 62

Ser Leu Ala Leu Ala Asp Asp Ala Ala Phe Arg Glu Arg Ala
1               5                   10

<210> SEQ ID NO 63
<211> LENGTH: 13
<212> TYPE: PRT
<213> ORGANISM: Bos taurus

<400> SEQUENCE: 63

Ser Leu Ala Leu Ala Asp Asp Ala Ala Phe Arg Glu Arg
1               5                   10

<210> SEQ ID NO 64
<211> LENGTH: 12
<212> TYPE: PRT
<213> ORGANISM: Bos taurus

<400> SEQUENCE: 64

Ser Leu Ala Leu Ala Asp Asp Ala Ala Phe Arg Glu
1               5                   10

<210> SEQ ID NO 65
<211> LENGTH: 11
<212> TYPE: PRT
<213> ORGANISM: Bos taurus

<400> SEQUENCE: 65

Ser Leu Ala Leu Ala Asp Asp Ala Ala Phe Arg
1               5                   10

<210> SEQ ID NO 66
<211> LENGTH: 10
<212> TYPE: PRT
<213> ORGANISM: Bos taurus

<400> SEQUENCE: 66

Ser Leu Ala Leu Ala Asp Asp Ala Ala Phe
1               5                   10

<210> SEQ ID NO 67
<211> LENGTH: 9
<212> TYPE: PRT
<213> ORGANISM: Bos taurus

<400> SEQUENCE: 67

Ser Leu Ala Leu Ala Asp Asp Ala Ala
1               5

<210> SEQ ID NO 68
<211> LENGTH: 8
<212> TYPE: PRT
<213> ORGANISM: Bos taurus

<400> SEQUENCE: 68

Ser Leu Ala Leu Ala Asp Asp Ala
1               5

<210> SEQ ID NO 69
<211> LENGTH: 7
<212> TYPE: PRT
<213> ORGANISM: Bos taurus

<400> SEQUENCE: 69

Ser Leu Ala Leu Ala Asp Asp
1               5

<210> SEQ ID NO 70
<211> LENGTH: 6
<212> TYPE: PRT
<213> ORGANISM: Bos taurus

<400> SEQUENCE: 70

Ser Leu Ala Leu Ala Asp
1               5

<210> SEQ ID NO 71
<211> LENGTH: 5
<212> TYPE: PRT
<213> ORGANISM: Bos taurus

<400> SEQUENCE: 71

Ser Leu Ala Leu Ala
1               5

<210> SEQ ID NO 72
<211> LENGTH: 4
<212> TYPE: PRT
<213> ORGANISM: Bos taurus

<400> SEQUENCE: 72

Ser Leu Ala Leu
1

<210> SEQ ID NO 73
<211> LENGTH: 3
<212> TYPE: PRT
<213> ORGANISM: Bos taurus

<400> SEQUENCE: 73

Ser Leu Ala
 1

<210> SEQ ID NO 74
<211> LENGTH: 35
<212> TYPE: PRT
<213> ORGANISM: Bos taurus

<400> SEQUENCE: 74

Ala Asp Asp Ala Ala Phe Arg Glu Arg Ala Arg Leu Leu Ala Ala Leu
 1               5                  10                  15

Glu Arg Arg His Trp Leu Asn Ser Tyr Met His Lys Leu Leu Val Leu
             20                  25                  30

Asp Ala Pro
 35

<210> SEQ ID NO 75
<211> LENGTH: 34
<212> TYPE: PRT
<213> ORGANISM: Bos taurus

<400> SEQUENCE: 75

Asp Asp Ala Ala Phe Arg Glu Arg Ala Arg Leu Leu Ala Ala Leu Glu
 1               5                  10                  15

Arg Arg His Trp Leu Asn Ser Tyr Met His Lys Leu Leu Val Leu Asp
             20                  25                  30

Ala Pro

<210> SEQ ID NO 76
<211> LENGTH: 33
<212> TYPE: PRT
<213> ORGANISM: Bos taurus

<400> SEQUENCE: 76

Asp Ala Ala Phe Arg Glu Arg Ala Arg Leu Leu Ala Ala Leu Glu Arg
 1               5                  10                  15

Arg His Trp Leu Asn Ser Tyr Met His Lys Leu Leu Val Leu Asp Ala
             20                  25                  30

Pro

<210> SEQ ID NO 77
<211> LENGTH: 32
<212> TYPE: PRT
<213> ORGANISM: Bos taurus

<400> SEQUENCE: 77

Ala Ala Phe Arg Glu Arg Ala Arg Leu Leu Ala Ala Leu Glu Arg Arg
 1               5                  10                  15

His Trp Leu Asn Ser Tyr Met His Lys Leu Leu Val Leu Asp Ala Pro
             20                  25                  30

<210> SEQ ID NO 78
<211> LENGTH: 31
<212> TYPE: PRT

```
<213> ORGANISM: Bos taurus

<400> SEQUENCE: 78

Ala Phe Arg Glu Arg Ala Arg Leu Leu Ala Ala Leu Glu Arg Arg His
 1               5                  10                  15

Trp Leu Asn Ser Tyr Met His Lys Leu Leu Val Leu Asp Ala Pro
             20                  25                  30

<210> SEQ ID NO 79
<211> LENGTH: 30
<212> TYPE: PRT
<213> ORGANISM: Bos taurus

<400> SEQUENCE: 79

Phe Arg Glu Arg Ala Arg Leu Leu Ala Ala Leu Glu Arg Arg His Trp
 1               5                  10                  15

Leu Asn Ser Tyr Met His Lys Leu Leu Val Leu Asp Ala Pro
             20                  20                  30

<210> SEQ ID NO 80
<211> LENGTH: 29
<212> TYPE: PRT
<213> ORGANISM: Bos taurus

<400> SEQUENCE: 80

Arg Glu Arg Ala Arg Leu Leu Ala Ala Leu Glu Arg Arg His Trp Leu
 1               5                  10                  15

Asn Ser Tyr Met His Lys Leu Leu Val Leu Asp Ala Pro
             20                  25

<210> SEQ ID NO 81
<211> LENGTH: 28
<212> TYPE: PRT
<213> ORGANISM: Bos taurus

<400> SEQUENCE: 81

Glu Arg Ala Arg Leu Leu Ala Ala Leu Glu Arg Arg His Trp Leu Asn
 1               5                  10                  15

Ser Tyr Met His Lys Leu Leu Val Leu Asp Ala Pro
20              25

<210> SEQ ID NO 82
<211> LENGTH: 27
<212> TYPE: PRT
<213> ORGANISM: Bos taurus

<400> SEQUENCE: 82

Arg Ala Arg Leu Leu Ala Ala Leu Glu Arg Arg His Trp Leu Asn Ser
 1               5                  10                  15

Tyr Met His Lys Leu Leu Val Leu Asp Ala Pro
20              25

<210> SEQ ID NO 83
<211> LENGTH: 26
<212> TYPE: PRT
<213> ORGANISM: Bos taurus

<400> SEQUENCE: 83

Ala Arg Leu Leu Ala Ala Leu Glu Arg Arg His Trp Leu Asn Ser Tyr
 1               5                  10                  15

Met His Lys Leu Leu Val Leu Asp Ala Pro
20              25
```

```
<210> SEQ ID NO 84
<211> LENGTH: 25
<212> TYPE: PRT
<213> ORGANISM: Bos taurus

<400> SEQUENCE: 84

Arg Leu Leu Ala Ala Leu Glu Arg Arg His Trp Leu Asn Ser Tyr Met
 1               5                  10                  15

His Lys Leu Leu Val Leu Asp Ala Pro
         20                  25

<210> SEQ ID NO 85
<211> LENGTH: 24
<212> TYPE: PRT
<213> ORGANISM: Bos taurus

<400> SEQUENCE: 85

Leu Leu Ala Ala Leu Glu Arg Arg His Trp Leu Asn Ser Tyr Met His
 1               5                  10                  15

Lys Leu Leu Val Leu Asp Ala Pro
            20

<210> SEQ ID NO 86
<211> LENGTH: 23
<212> TYPE: PRT
<213> ORGANISM: Bos taurus

<400> SEQUENCE: 86

Leu Ala Ala Leu Glu Arg Arg His Trp Leu Asn Ser Tyr Met His Lys
 1               5                  10                  15

Leu Leu Val Leu Asp Ala Pro
 20

<210> SEQ ID NO 87
<211> LENGTH: 22
<212> TYPE: PRT
<213> ORGANISM: Bos taurus

<400> SEQUENCE: 87

Ala Ala Leu Glu Arg Arg His Trp Leu Asn Ser Tyr Met His Lys Leu
 1               5                  10                  15

Leu Val Leu Asp Ala Pro
 20

<210> SEQ ID NO 88
<211> LENGTH: 21
<212> TYPE: PRT
<213> ORGANISM: Bos taurus

<400> SEQUENCE: 88

Ala Leu Glu Arg Arg His Trp Leu Asn Ser Tyr Met His Lys Leu Leu
 1               5                  10                  15

Val Leu Asp Ala Pro
 20

<210> SEQ ID NO 89
<211> LENGTH: 20
<212> TYPE: PRT
<213> ORGANISM: Bos taurus

<400> SEQUENCE: 89
```

```
Leu Glu Arg Arg His Trp Leu Asn Ser Tyr Met His Lys Leu Leu Val
 1               5                  10                  15

Leu Asp Ala Pro
             20
```

<210> SEQ ID NO 90
<211> LENGTH: 19
<212> TYPE: PRT
<213> ORGANISM: Bos taurus

<400> SEQUENCE: 90

```
Glu Arg Arg His Trp Leu Asn Ser Tyr Met His Lys Leu Leu Val Leu
 1               5                  10                  15

Asp Ala Pro
```

<210> SEQ ID NO 91
<211> LENGTH: 18
<212> TYPE: PRT
<213> ORGANISM: Bos taurus

<400> SEQUENCE: 91

```
Arg Arg His Trp Leu Asn Ser Tyr Met His Lys Leu Leu Val Leu Asp
 1               5                  10                  15

Ala Pro
```

<210> SEQ ID NO 92
<211> LENGTH: 17
<212> TYPE: PRT
<213> ORGANISM: Bos taurus

<400> SEQUENCE: 92

```
Arg His Trp Leu Asn Ser Tyr Met His Lys Leu Leu Val Leu Asp Ala
 1               5                  10                  15

Pro
```

<210> SEQ ID NO 93
<211> LENGTH: 16
<212> TYPE: PRT
<213> ORGANISM: Bos taurus

<400> SEQUENCE: 93

```
His Trp Leu Asn Ser Tyr Met His Lys Leu Leu Val Leu Asp Ala Pro
 1               5                  10                  15
```

<210> SEQ ID NO 94
<211> LENGTH: 15
<212> TYPE: PRT
<213> ORGANISM: Bos taurus

<400> SEQUENCE: 94

```
Trp Leu Asn Ser Tyr Met His Lys Leu Leu Val Leu Asp Ala Pro
 1               5                  10                  15
```

<210> SEQ ID NO 95
<211> LENGTH: 14
<212> TYPE: PRT
<213> ORGANISM: Bos taurus

<400> SEQUENCE: 95

```
Leu Asn Ser Tyr Met His Lys Leu Leu Val Leu Asp Ala Pro
 1               5                  10
```

```
<210> SEQ ID NO 96
<211> LENGTH: 13
<212> TYPE: PRT
<213> ORGANISM: Bos taurus

<400> SEQUENCE: 96

Asn Ser Tyr Met His Lys Leu Leu Val Leu Asp Ala Pro
 1               5                  10

<210> SEQ ID NO 97
<211> LENGTH: 12
<212> TYPE: PRT
<213> ORGANISM: Bos taurus

<400> SEQUENCE: 97

Ser Tyr Met His Lys Leu Leu Val Leu Asp Ala Pro
 1               5                  10

<210> SEQ ID NO 98
<211> LENGTH: 11
<212> TYPE: PRT
<213> ORGANISM: Bos taurus

<400> SEQUENCE: 98

Tyr Met His Lys Leu Leu Val Leu Asp Ala Pro
 1               5                  10

<210> SEQ ID NO 99
<211> LENGTH: 10
<212> TYPE: PRT
<213> ORGANISM: Bos taurus

<400> SEQUENCE: 99

Met His Lys Leu Leu Val Leu Asp Ala Pro
 1               5                  10

<210> SEQ ID NO 100
<211> LENGTH: 9
<212> TYPE: PRT
<213> ORGANISM: Bos taurus

<400> SEQUENCE: 100

His Lys Leu Leu Val Leu Asp Ala Pro
 1               5

<210> SEQ ID NO 101
<211> LENGTH: 8
<212> TYPE: PRT
<213> ORGANISM: Bos taurus

<400> SEQUENCE: 101

Lys Leu Leu Val Leu Asp Ala Pro
 1               5

<210> SEQ ID NO 102
<211> LENGTH: 7
<212> TYPE: PRT
<213> ORGANISM: Bos taurus

<400> SEQUENCE: 102

Leu Leu Val Leu Asp Ala Pro
 1               5

<210> SEQ ID NO 103
<211> LENGTH: 6
```

<210> SEQ ID NO 103
<211> LENGTH: 5
<212> TYPE: PRT
<213> ORGANISM: Bos taurus

<400> SEQUENCE: 103

Leu Val Leu Asp Ala Pro
 1               5

<210> SEQ ID NO 104
<211> LENGTH: 5
<212> TYPE: PRT
<213> ORGANISM: Bos taurus

<400> SEQUENCE: 104

Val Leu Asp Ala Pro
 1           5

<210> SEQ ID NO 105
<211> LENGTH: 4
<212> TYPE: PRT
<213> ORGANISM: Bos taurus

<400> SEQUENCE: 105

Leu Asp Ala Pro
 1

<210> SEQ ID NO 106
<211> LENGTH: 4
<212> TYPE: PRT
<213> ORGANISM: Bos taurus

<400> SEQUENCE: 106

Leu Asp Ala Pro
 1

<210> SEQ ID NO 107
<211> LENGTH: 819
<212> TYPE: DNA
<213> ORGANISM: Bos taurus

<400> SEQUENCE: 107

```
ttcgccctac ctccttggcg gggcgtcttt cagtaagtgg acatccaagc ctcccaggga      60
agggtgggga ctccgagagg tggaaagaga cccgaaaaga atgggaacaa agactcagaa     120
aaaaaggggg gaaatagaga cccagagagg aggccagaga taggaggttg acaggtaggt     180
aatctgcaaa ataaagagat acaaaaggat tctgagaaag gctttgagag acttgaaagg     240
agtcgaagca ggaacgagtt tgttccttga gcaacgttta ttgggtctgg ggtgtgtgcc     300
acgcgtgcgc cgagcactgg ggcgggacag gggcatcaga ctcggtctct gtactcagga     360
ggctcggaac tggtgaacac tgagccgaag actcacacag agcaagagac aggagacaga     420
gaccgagccc ctccgcatct ggtgcagtca cagggcttcg agttagaccg cggggagaac     480
aggcggcggg ccgcgggccg agacccacgg taaccgcctc tttccatctc ccggcagact     540
ccgcaccccc ggcgaggctc gggcgggtcc ggccacccc cagtcgcggc ggagcctggc     600
gctggcggac gacgcggcct tccgggagcg cgcgcggctg ctggccgccc tcgagcgccg     660
ccactggctg aactcgtaca tgcacaagct gctggtgctg acgcgccct gagcgcctgc     720
ccgccccacc tcaataaaga ccgtgctgtg cctcccgact gcgcctcctt cctacgcctc     780
gtgtgcgtgt ggtggtggtg gtggtgtgtg tgtgtctac                           819
```

<210> SEQ ID NO 108

<211> LENGTH: 1515
<212> TYPE: DNA
<213> ORGANISM: Homo sapien

<400> SEQUENCE: 108

```
gacggtcctt ccgccagtct ctattttag ccctctgaca caccccctgt gtccacctct      60
ctgtctgtct gtctctcccc ctccctcgtc tcaggtccag cttctggtcc caattagttg     120
gtggcggcca aggcagcggc aggtccccca ccccggctc ctcattaccg ctggcggctc     180
ctaatgagcc tggggagggg gtgaccccgc gtccccggcc cccggcctg cgtcactgcc     240
cggtgcgggg gctgcggagg cgatataagg gggctgccac catcgctgcc ccagcccact     300
gcacggtagg ggactgtgcg ggaagctggg ggtggatgca tggtggggcc cggggttctg     360
ggccgggatg cagccctact gagccccttt ctggttctcc acaggtgatg gagacccgcc     420
aggtgtccag gagccctcgg gttcggctgc tgctgctgct gctgctgctg ctggtggtgc     480
cctgggcgt ccgcactgcc tcgggagtcg ccctgccccc gtcgggtc ctcaggtagg       540
tgccagtccc agaactccca gggaggggtg ggaacttgga gaagtgggaa gagaaccaaa     600
gagaaagggg acggaagatc cagaaagcgg aacagaagcc caaagagagg gcgaccgaga     660
cccagcgaga agacagagac tagggggtggg ggaaggcggg aggagggttt ggtggtagtg     720
gtggtgcggg aaatggacag aaaatcagca agggaaagag acacagaaag atagatcccg     780
agaaaggcgt ggagaggctc gaaaggagtc gttgcagaaa cggattcatt ctttgagcaa     840
cgttttattgg gttcttggtg tgcgcctggc catgcgctga cgctgtggg cggacaagtg      900
catcagactc ggtctcagta cctggggagt ttcgaacctg gtgagcagag agacagagac     960
ccacacagag aacgagagag acaggggggag ccggaccgag ccactccacg gactgggcag    1020
taacgggggct tcgagttaga ccgcggggag gacaggcggc ggcaagagcg agtctggacg    1080
cgcggtcacc cgtctctcc acagcctccg ccccccagga cgggcctggg cggatcccgc     1140
caccccagg ccgcggagga gcctggcgct ggcggacgac gcggccttcc gggagcgcgc     1200
gcggttgctg gccgccctcg agcgccgcca ctggctgaac tcgtacatgc acaagctgct    1260
ggtgttggat gcgccctgag cgcgctgccc gtccccatct taataaagac catgccctgc    1320
gctccggact gcgcctcgtt cctgcgcgac ctgcgtgtgc gttgggttgg gggcgcgggg    1380
cttgaaatgg ggggtacaaa agagacacga ctctgtgtcg gccactctgg catctctctc    1440
ctcagtcccc actctatttt ctttcctcaa ttccgtttct ctctgcctgt ctttgtccag    1500
gaagctggct tcttt                                                    1515
```

<210> SEQ ID NO 109
<211> LENGTH: 546
<212> TYPE: PRT
<213> ORGANISM: Rattus norvegicus
<220> FEATURE:
<221> NAME/KEY: VARIANT
<222> LOCATION: (1)...(546)
<223> OTHER INFORMATION: Xaa = Any Amino Acid

<400> SEQUENCE: 109

```
Met Pro Trp Leu Glu Ala Leu Pro Tyr Ile Cys Gly Trp Leu Ile Leu
 1               5                  10                  15

Arg Ser Cys Leu Leu Val Gly Ala Gln Leu Asp Ser Asp Gly Thr Ile
            20                  25                  30

Thr Ile Glu Glu Gln Ile Val Leu Val Met Lys Ala Lys Met Gln Cys
        35                  40                  45
```

-continued

```
Glu Leu Asn Ile Thr Ala Gln Phe Gln Glu Gly Glu Gly Asn Cys Phe
 50                  55                  60
Pro Glu Trp Asp Gly Leu Ile Cys Trp Pro Arg Gly Thr Ala Gly Lys
 65                  70                  75                  80
Thr Ser Ala Met Pro Cys Pro Ser Tyr Val Tyr Asp Phe Asn His Lys
                 85                  90                  95
Gly Val Ala Phe Arg His Cys Thr Pro Asn Gly Thr Trp Asp Phe Ile
                100                 105                 110
His Gly Ser Asn Lys Thr Trp Ala Asn Tyr Ser Asp Cys Phe Leu Gln
                115                 120                 125
Pro Asp Ile Asn Ile Gly Lys Gln Glu Phe Phe Glu Asn Leu Tyr Ile
130                 135                 140
Leu Tyr Thr Val Gly Tyr Ser Ile Ser Phe Gly Ser Leu Ala Val Ala
145                 150                 155                 160
Ile Leu Ile Ile Gly Tyr Phe Arg Arg Leu His Cys Thr Arg Asn Tyr
                165                 170                 175
Ile His Leu His Leu Phe Val Ser Phe Met Leu Arg Ala Xaa Ser Ile
                180                 185                 190
Phe Val Lys Asp Arg Val Ala Gln Ala His Leu Gly Val Glu Ala Leu
                195                 200                 205
Gln Ser Leu Val Met Gln Gly Asp Leu Gln Asn Phe Ile Gly Gly Pro
210                 215                 220
Ser Val Asp Lys Ser Gln Tyr Val Gly Cys Lys Ile Ala Val Val Met
225                 230                 235                 240
Phe Ile Tyr Phe Leu Ala Thr Asn Tyr Tyr Trp Ile Leu Val Glu Gly
                245                 250                 255
Leu Tyr Leu His Asn Leu Ile Phe Val Ser Phe Phe Ser Asp Thr Lys
                260                 265                 270
Tyr Leu Trp Gly Phe Ile Leu Ile Gly Trp Gly Phe Pro Ala Val Phe
                275                 280                 285
Val Val Ala Trp Ala Val Ala Arg Ala Thr Leu Ala Asp Thr Arg Cys
                290                 295                 300
Trp Glu Leu Ser Ala Gly Asp Arg Trp Ile Tyr Xaa Xaa Pro Ile Leu
305                 310                 315                 320
Ala Ala Ile Gly Leu Asn Phe Ile Leu Phe Leu Asn Thr Val Arg Val
                325                 330                 335
Leu Ala Thr Lys Ile Trp Glu Thr Asn Ala Val Gly His Asp Met Arg
                340                 345                 350
Lys Gln Tyr Arg Lys Leu Ala Lys Ser Thr Leu Val Leu Val Leu Val
                355                 360                 365
Phe Gly Val His Tyr Ile Val Phe Ile Cys Gln Pro His Ser Phe Ser
                370                 375                 380
Gly Leu Trp Trp Glu Ile Arg Met His Cys Glu Leu Phe Phe Asn Ser
385                 390                 395                 400
Phe Gln Gly Phe Phe Val Ser Ile Val Tyr Cys Tyr Cys Asn Gly Glu
                405                 410                 415
Val Gln Ala Glu Val Lys Lys Thr Trp Thr Arg Trp Asn Leu Ser Ile
                420                 425                 430
Asp Trp Lys Lys Ala Pro Pro Cys Gly Gly His Arg Tyr Gly Ser Val
                435                 440                 445
Leu Thr Thr Val Thr His Ser Thr Ser Gln Ser Gln Met Gly Pro
450                 455                 460
Ser Thr Arg Leu Val Leu Ile Ser Ser Lys Pro Ala Lys Thr Ala Cys
```

```
                465                 470                 475                 480
Arg Gln Ile Asp Ser His Val Thr Leu Pro Gly Tyr Val Trp Ser Ser
                    485                 490                 495

Ser Glu Gln Asp Cys Gln Pro Gln Ser Thr Pro Glu Thr Lys Lys
                500                 505                 510

Gly His Gly Arg Gln Glu Asp Ser Pro Val Gly Glu Ser Ser Arg
            515                 520                 525

Pro Val Ala Phe Thr Ile Asp Thr Glu Gly Cys Lys Gly Glu Ser His
    530                 535                 540

Pro Ile
545

<210> SEQ ID NO 110
<211> LENGTH: 550
<212> TYPE: PRT
<213> ORGANISM: Homo sapiens

<400> SEQUENCE: 110

Met Ala Gly Leu Gly Ala Ser Leu His Val Trp Gly Trp Leu Met Leu
 1               5                  10                  15

Gly Ser Cys Leu Leu Ala Arg Ala Gln Leu Asp Ser Asp Gly Thr Ile
                20                  25                  30

Thr Ile Glu Glu Gln Ile Val Leu Val Leu Lys Ala Lys Val Gln Cys
            35                  40                  45

Glu Leu Asn Ile Thr Ala Gln Leu Gln Glu Gly Glu Gly Asn Cys Phe
        50                  55                  60

Pro Glu Trp Asp Gly Leu Ile Cys Trp Pro Arg Gly Thr Val Gly Lys
65                  70                  75                  80

Ile Ser Ala Val Pro Cys Pro Pro Tyr Ile Tyr Asp Phe Asn His Lys
                85                  90                  95

Gly Val Ala Phe Arg His Cys Asn Pro Asn Gly Thr Trp Asp Phe Met
                100                 105                 110

His Ser Leu Asn Lys Thr Trp Ala Asn Tyr Ser Asp Cys Leu Arg Phe
            115                 120                 125

Leu Gln Pro Asp Ile Ser Ile Gly Lys Gln Glu Phe Phe Glu Arg Leu
        130                 135                 140

Tyr Val Met Tyr Thr Val Gly Tyr Ser Ile Ser Phe Gly Ser Leu Ala
145                 150                 155                 160

Val Ala Ile Leu Ile Ile Gly Tyr Phe Arg Arg Leu His Cys Thr Arg
                165                 170                 175

Asn Tyr Ile His Met His Leu Phe Val Ser Phe Met Leu Arg Ala Thr
                180                 185                 190

Ser Asp Phe Val Lys Asp Arg Val Val His Ala His Ile Gly Val Lys
        195                 200                 205

Glu Leu Glu Leu Ser Leu Ile Met Gln Asp Asp Pro Gln Asn Ser Ile
    210                 215                 220

Glu Ala Thr Ser Val Asp Lys Ser Gln Tyr Ile Gly Cys Lys Ile Ala
225                 230                 235                 240

Val Val Met Phe Ile Tyr Phe Leu Ala Thr Asn Tyr Trp Ile Leu Val
                245                 250                 255

Glu Gly Leu Tyr Leu His Asn Leu Ile Phe Val Ala Phe Phe Ser Asp
                260                 265                 270

Thr Lys Tyr Leu Trp Gly Phe Ile Leu Ile Gly Trp Gly Phe Pro Ala
            275                 280                 285
```

```
Ala Phe Val Ala Ala Trp Ala Val Arg Ala Thr Leu Ala Asp Ala
    290                 295                 300

Arg Cys Trp Glu Leu Ser Ala Gly Asp Ile Lys Trp Ile Tyr Gln Ala
305                 310                 315                 320

Pro Ile Leu Ala Ala Ile Gly Leu Asn Phe Ile Leu Phe Leu Asn Thr
                325                 330                 335

Val Arg Val Leu Ala Thr Lys Ile Trp Glu Thr Asn Ala Val Gly His
            340                 345                 350

Asp Thr Arg Lys Gln Tyr Arg Lys Leu Ala Lys Ser Thr Leu Val Leu
        355                 360                 365

Val Leu Val Phe Gly Val His Tyr Ile Val Phe Val Cys Leu Pro His
    370                 375                 380

Ser Phe Thr Gly Leu Gly Trp Glu Ile Arg Met His Cys Glu Leu Phe
385                 390                 395                 400

Phe Asn Ser Phe Gln Gly Phe Phe Val Ser Ile Ile Tyr Cys Tyr Cys
                405                 410                 415

Asn Gly Glu Val Gln Ala Glu Val Lys Lys Met Trp Ser Arg Trp Asn
            420                 425                 430

Leu Ser Val Asp Trp Lys Arg Thr Pro Pro Cys Gly Ser Arg Arg Cys
        435                 440                 445

Gly Ser Val Leu Thr Thr Val Thr His Ser Thr Ser Ser Gln Ser Gln
450                 455                 460

Val Ala Ala Ser Thr Arg Met Val Leu Ile Ser Gly Lys Ala Ala Lys
465                 470                 475                 480

Ile Ala Ser Arg Gln Pro Asp Ser His Ile Thr Leu Pro Gly Tyr Val
                485                 490                 495

Trp Ser Asn Ser Glu Gln Asp Cys Leu Pro His Ser Phe His Glu Glu
            500                 505                 510

Thr Lys Glu Asp Ser Gly Arg Gln Gly Asp Ile Leu Met Glu Lys
        515                 520                 525

Pro Ser Arg Pro Met Glu Ser Asn Pro Asp Thr Glu Gly Cys Gln Gly
    530                 535                 540

Glu Thr Glu Asp Val Leu
545                 550

<210> SEQ ID NO 111
<211> LENGTH: 40
<212> TYPE: PRT
<213> ORGANISM: Bos Taurus

<400> SEQUENCE: 111

Ala Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp Val His
            20                  25                  30

Asn Phe Val Ala Leu Gly Ala Ser
        35                  40

<210> SEQ ID NO 112
<211> LENGTH: 39
<212> TYPE: PRT
<213> ORGANISM: Homo sapiens

<400> SEQUENCE: 112

Ala Val Ser Glu His Gln Leu Leu His Asp Lys Gly Lys Ser Ile Gln
1               5                   10                  15
```

-continued

```
Asp Leu Arg Arg Arg Phe Phe Leu His His Leu Ile Ala Glu Ile His
            20                  25              30

Thr Ala Glu Ile Arg Ala Thr
            35
```